(12) United States Patent
Palmatier et al.

(10) Patent No.: US 8,317,866 B2
(45) Date of Patent: Nov. 27, 2012

(54) SYSTEM AND METHODS FOR A LATERALLY EXPANDING IMPLANT

(75) Inventors: Stan Palmatier, Olive Branch, MS (US); Michael Hugo, Homestead, FL (US); Anthony J. Melkent, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 386 days.

(21) Appl. No.: 12/792,366

(22) Filed: Jun. 2, 2010

(65) Prior Publication Data

US 2011/0301711 A1 Dec. 8, 2011

(51) Int. Cl.
*A61F 2/44* (2006.01)
(52) U.S. Cl. .................. 623/17.11; 623/23.47
(58) Field of Classification Search .................. 606/279; 623/17.11, 17.15, 17.16, 23.47
See application file for complete search history.

(56) References Cited

U.S. PATENT DOCUMENTS

| 2005/0113917 A1* | 5/2005 | Chae et al. ................. 623/17.11 |
| 2010/0292796 A1* | 11/2010 | Greenhalgh et al. ....... 623/17.11 |

* cited by examiner

*Primary Examiner* — Kevin T Truong
*Assistant Examiner* — Larry E. Waggle, Jr.

(57) ABSTRACT

An implant for a spinal column and a method for inserting the same into a patient is disclosed. The implant includes an elongated body positionable in a spinal disc space. The body comprises a first body member and a second body member that each include at least one wedge extending into an interior cavity. A front bracket is connected with a leading portion of the first and second body members and a rear bracket connected with a trailing portion of said first and second body members. The brackets allow the first and second body members to move between an expanded state and an unexpanded state. An expansion component is positioned within the interior cavity when the implant is in an expanded state and the implant is then positioned in an unexpanded state. The expansion component includes at least one inverted wedge in engagement with the wedge of the first and second body members. The inverted wedge is operable to cause the first and second body members to expand way from one another to the expanded state. A bone graft member is then inserted into the interior cavity defined by the first and second body members.

20 Claims, 55 Drawing Sheets

SYSTEM AND METHODS FOR A LATERALLY EXPANDING IMPLANT

BACKGROUND

The present invention relates generally to interbody fusion and more particularly, to methods and systems for inserting an implant between adjacent vertebra that is operable to be inserted in an unexpanded state and then laterally expand thereby increasing the footprint of the implant between the respective adjacent vertebral members.

Several techniques and systems have been developed for correcting and stabilizing the spine and for facilitating fusion at various levels of the spine. The anatomy from Kambin's Triangle, Cauda Equina, vascular structures, and other areas not mentioned make it difficult to get a large implant in the disc space between adjacent vertebral members. A large graft opening in implants is desired to facilitate spinal fusion and current implants do not provide a large enough graft opening. When an implant is placed into a disc space the channel or path that the implant took to enter the disc space makes it easy from the implant to migrate back out the same path. In addition, precise Lordosis is difficult, if not impossible, to achieve using current implants.

Further, correction of deformities in the sagittal plane is difficult to achieve with one implant. Surface area from the implant to the endplate is so small that the implants subside too much and tend to want to break through the endplates. Unilateral fixation is not always an option because of stability issues of a narrow implant. As a result, additional improvements in spinal fusion are needed.

SUMMARY

According to one aspect an implant for a spinal column is disclosed that includes an elongated body configured to be positioned in a spinal disc space. The body comprises a first body member and a second body member. In one form, the first and second body members include a generally convexly curved upper surface and a generally convexly curved lower surface. The first and second body members each include at least one wedge extending into an interior cavity defined by the first and second body members. In one representative form, the first body member is longer than the second body member such that the first body member sits deeper into the spinal disc space so that a leading end of the first body member sits on an anterior margin of the vertebral endplate.

In one form, a front bracket is connected with a leading portion of the first and second body members. A rear bracket can also be connected with a trailing portion of the first and second body members. However, a single bracket could also be used that is positioned somewhere between the leading and trailing end portions of the first and second body members. The brackets are operable to allow the first and second body members to move between an expanded state and an unexpanded state. An expansion component is sized and configured to be positioned within the interior cavity defined by the first and second body members when in the unexpanded state. The expansion component includes at least one inverted wedge in engagement with at least one wedge of the first and second body members. The inverted wedge is operable to cause the first and second body members to expand away from one another to the expanded state by application of force on the wedge of the first and second body members as the expansion component is retracted out of the first and second body members.

In one illustrative form, a front end of the first body member tapers inwardly from a sidewall of the first body member at a predetermined angle and a second front end of the second body member tapers outwardly from a second sidewall of the second body member at the same predetermined angle toward the first body member. In one form, the upper and lower surfaces of one or both of the first and second body members have a predetermined coronal plane cross-section convexity radius. The predetermined coronal plane cross-section convexity radius can fall in a range between approximately 70-250 millimeters depending on the requirements of a given patient. In another form, the generally convexly curved upper and lower surfaces of one or both of the first and second body members has a predetermined sagittal plane convexity radius. In one aspect of the present invention, the predetermined sagittal plane convexity radius falls in a range between approximately 10-200 millimeters.

In yet another form, the upper and lower surfaces of the first and second body members are configured to define a lordotic angle in a sagittal plane when installed in the spinal disc space in an oblique orientation. Further, the upper and lower surfaces of the first and second body members can also be configured to define a coronal convexity when installed in the spinal disc space in an oblique orientation.

A bone graft member is configured to be inserted into the interior cavity defined by the first and second body members when positioned in the expanded state after the expansion component has been removed from the first and second body members. The upper and lower surfaces of the bone graft member can have a predetermined coronal plane cross-section convexity radius and a predetermined sagittal plane convexity radius. Further, in other forms the upper and lower surfaces of the first and second body members and an upper and lower surface of the bone graft member can be configured to define a lordotic angle in a sagittal plane when installed in the spinal disc space in an oblique orientation. In addition, the upper and lower surfaces of the first and second body members and an upper and lower surface of the bone graft member can be configured to have a coronal convexity when installed in the spinal disc space in an oblique orientation.

Another aspect discloses a method of implanting an implant between adjacent vertebral members. In this form, a switching stick is connected to a connector at a trailing end of the implant. The implant may then be expanded to an expanded state. An expansion component is then connected to a shaft of an instrument. The expansion component is then positioned on the switching stick such that the expansion component is capable of travelling along or on the switching stick. The expansion component is then inserted into passages defined by an interior space of the implant such that at least one wedge of the implant is in alignment with at least one inverted wedge of the expansion component.

The implant is then positioned in an unexpanded state encapsulating at least a portion of the expansion component within an interior space defined by the implant. The implant is then inserted between adjacent vertebral members with the instrument from an oblique approach. The implant includes a first body member and a second body member and the first body member has a length greater than the second body member such that the first body member sits deeper into a disc space between the adjacent vertebral members. The shaft of the instrument is then retracted thereby causing the at least one inverted wedge of the expansion component to exert a lateral force on the at least one wedge of the implant causing the implant to laterally expand until reaching an expanded state.

After the implant is expanded, the instrument and expansion component are taken off of the switching stick. A bone graft member is then connected with a second instrument on the switching stick. The bone graft member is then inserted into the passages defined by the interior space of the implant. In one aspect, the upper and lower bone engaging surfaces of the first and second body members and the bone graft member have a coronal cross-section convexity having a predetermined radius. In one form, the predetermined radius is in the range of approximately 70-250 millimeters. In addition, in another form the upper and lower bone engaging surfaces of the first and second body members and the bone graft member have a sagittal convexity having a predetermined radius. The predetermined radius is in the range of approximately 10-200 millimeters.

Related features, aspects, embodiments, objects and advantages of the present invention will be apparent from the following description.

DESCRIPTION OF THE ILLUSTRATED EMBODIMENTS

Figure 1:
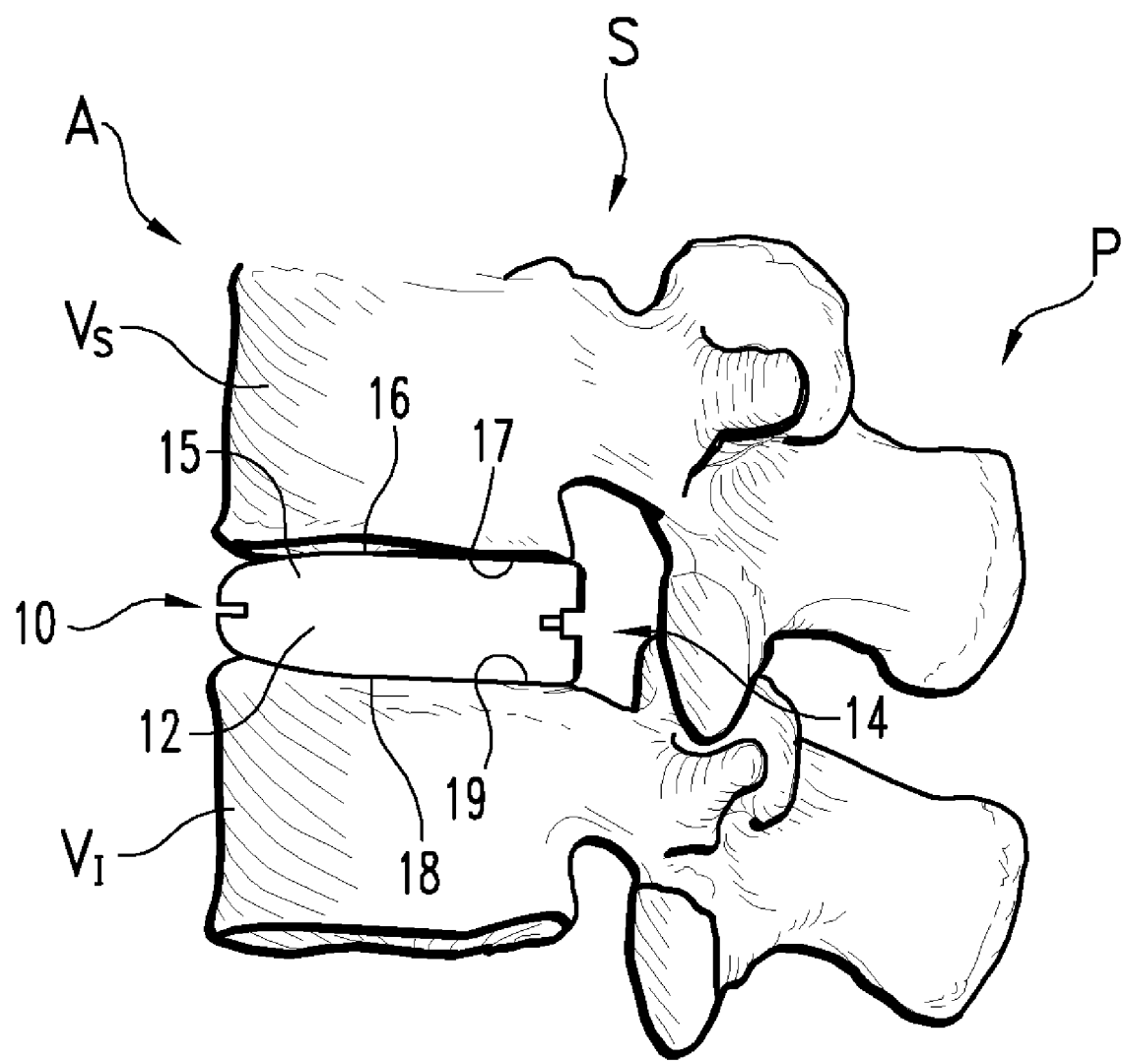
FIG. 1 is a lateral view of adjacent vertebral members having an implant inserted in an intervertebral disc space between the respective vertebral members.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Methods, techniques, instrumentation and implants are provided to restore and/or maintain a collapsed spinal disc space at a desired disc space height and orientation. The instruments and implants may be used in techniques employing minimally invasive instruments and technology to access the disc space. Access to the collapsed disc space can be uni-portal, bi-portal, or multi-portal, but is preferentially uni-portal. The instruments and implants may also be employed in open surgical procedures in which skin and tissue is dissected and retracted to access the collapsed spinal disc space. The methods, techniques, instruments and implants may also be employed in any surgical approach to the spine, including lateral, antero-lateral, postero-lateral, oblique, posterior, and anterior approaches. Preferentially, the methods, techniques, instruments and implants are employed using a posterior approach to the spine. Also, the surgical methods, techniques, instruments and implants may find application at all vertebral segments of the spine, including the lumbar, thoracic and cervical spinal regions.

FIG. 1 illustrates a lateral view of one embodiment of an implant 10 positioned within a patient's spine S. For reference, this application indicates the anterior and posterior portion of a patient's body using the reference letters "A" and "P," respectively. However, the implant 10 and methods, techniques, and instruments are not limited to any particular configuration or insertion approach with respect to the anterior or posterior portions of the patient. To maintain the least invasive approach, preferentially the implant 10 is inserted through a posterior approach.

As seen in FIG. 1, the implant 10 comprises an elongate body 12 sized to fit within the intervertebral space 14 between adjacent vertebral members $V_S$, $V_I$. In this form, the body 12 is shaped to conform to the intervertebral space 14 between the adjacent vertebral members $V_S$, $V_I$. The body 12 includes a superior surface 16, an inferior surface 18, and at least a pair of surrounding sidewalls 15. The superior surface 16 contacts the lower surface or endplate 17 of the superior vertebral member $V_S$ and the inferior surface 18 contacts the upper surface or endplate 19 of the inferior vertebral member $V_I$. As set forth in greater detail below, the implant 10 includes one or more inner chambers or cavities that may receive bone growth material and/or bone grafts that grow through the inferior and posterior surfaces 16, 18 to fuse with the vertebral members $V_S$, $V_I$.

Figure 2:
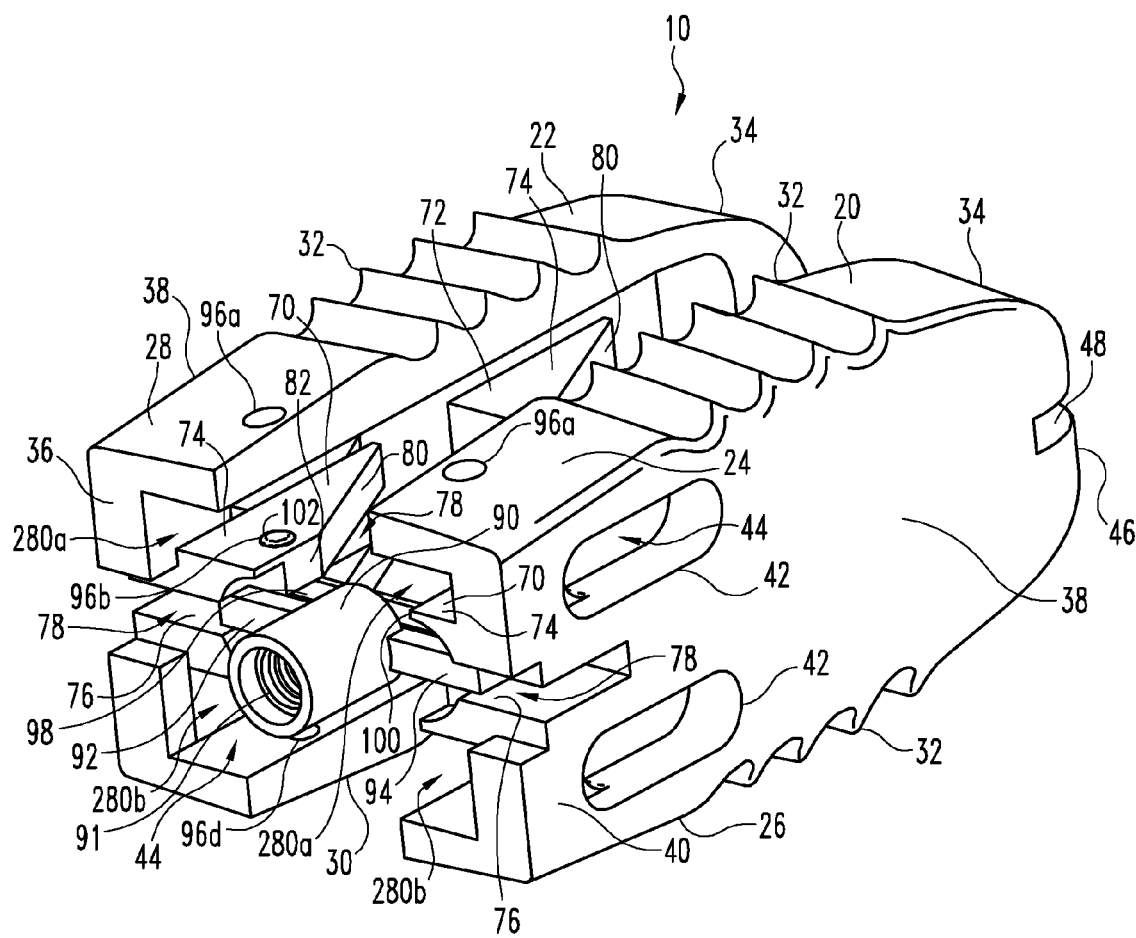
FIG. 2 is a perspective rear view of a representative implant.
Figure 3:
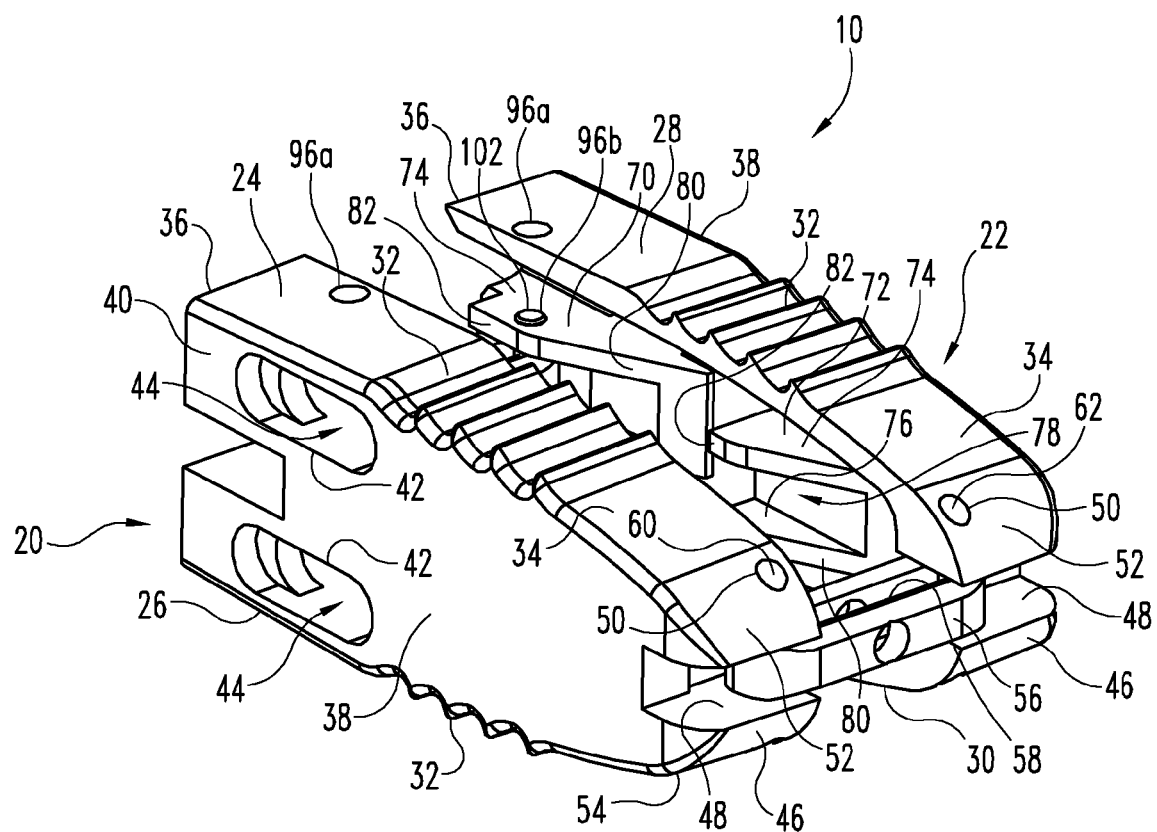
FIG. 3 is a perspective front view of the implant illustrated in FIG. 2.
Figure 4:
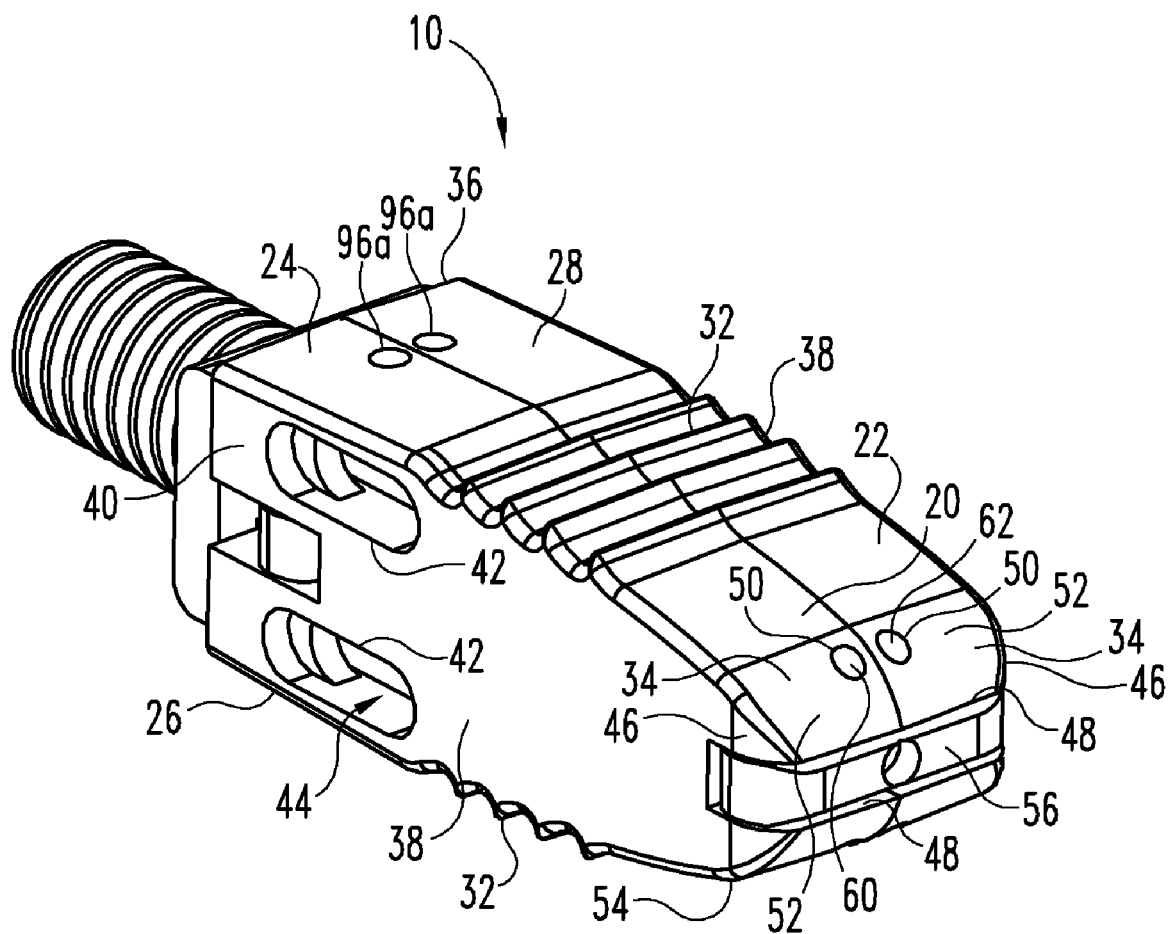
FIG. 4 is a perspective front view of the implant illustrated in FIG. 2 in an unexpanded state encapsulating a portion of an expansion component.

Further details regarding one embodiment of the implant 10 are shown in FIGS. 2-5. The implant 10 includes an elongate body 12 that is comprised of a first body member or half 20 and a second body member or half 22. The first and second body members 20, 22 are operable to be positioned in an expanded state as illustrated in FIGS. 2 and 3 as well as a compressed or unexpanded state as illustrated in FIG. 4. In particular, the first and second body members 20, 22 are inserted between the vertebral members $V_S$, $V_I$ in the unexpanded state as illustrated in FIG. 4 and then expanded to the expanded state illustrated in FIGS. 2 and 3. In one form, the first and second body members 20, 22 of the implant 10 are formed having a convex shape.

As a result of the implant 10 being able to expand after being inserted between the vertebral members $V_S$, $V_I$, extreme manipulation of the patient's anatomy is not required for a large implant. The implant 10 enters the disc space 14 at a set width and then expands to a larger width. By being inserted at a reduced width, it reduces the amount of neural retraction. In the expanded state, the increase in width provides several benefits such as creating a wider more stable footprint, allows for a larger graft area, and allows for a larger surface area for the implant 10 to contact the endplates 17, 19 of the vertebral members $V_S$, $V_I$. In addition, in the expanded state the implant 10 is inhibited from migrating out of the channel that the implant 10 was originally inserted through. Also, the heights of the first and second body members 20, 22 can be changed or adjusted so that more precise Lordosis and corrections in the sagittal plane can be achieved. Further, unilateral fixation of the vertebral members $V_S$, $V_I$ is more likely due to a larger more stable footprint achieved with a single implant.

The first body member 20 includes an upper bone engaging surface 24 and an opposite lower bone engaging surface 26 and the second body member 22 likewise includes an upper bone engaging surface 28 and an opposite lower bone engaging surface 30. The upper and lower bone engaging surfaces 24, 26, 28, 30 each have a generally convex shape to fit the concave shape of the endplates 17, 19 of the respective adjacent vertebral members $V_S$, $V_I$. At least a portion of the upper bone engaging surfaces 24, 28 and lower bone engaging surfaces 26, 30 can be provided with a plurality of bone engagement members 32. The bone engagement members 32 can comprise grooves, recesses, ridges, serrations, knurlings, spikes, roughened surfaces, or smooth surfaces for engaging the endplates 17, 19 of the adjacent vertebral members $V_S$, $V_I$. As illustrated, the bone engagement members 32 project outwardly to engage bone tissue of the endplates 17, 19 of the adjacent vertebral members $V_S$, $V_I$.

The first and second body members 20, 22 include a leading end portion 34 that is rounded or tapered so that the body 12 distracts the adjacent vertebral members $V_S$, $V_I$ as the body 12 is inserted in a collapsed disc space 14. In addition, the first and second body members 20, 22 include a proximal end wall 36, and sidewalls 38 extending between the proximal end walls 36 and the leading end portion 34. In one form, the sidewalls 38 are sized to have a height corresponding to a desired disc space height between the adjacent vertebral members $V_S$, $V_I$.

In one form, an end portion 40 of each body member 20, 22 includes one or more slots 42 that extend into an interior space 44 defined by each respective body member 20, 22. The slots 42 permit the introduction of bone growth material into the interior space 44 of the body members 20, 22 once installed between the respective adjacent vertebral members $V_S$, $V_I$. In addition, the slots 42 can be used by other surgical instruments to engage the body members 20, 22, if needed. Further, a front portion 46 of each respective body member 20, 22 includes a central generally rectangular shaped recess or notch 48 that extends inwardly a predetermined distance into each respective body member 20, 22.

The front portion 46 of each respective body member 20, 22 also includes an aperture or bore 50 that runs through an upper portion 52 of each body member 20, 22 to the recess 48 and then on through a lower portion 54 of each body member 20, 22. See FIGS. 3-5. As illustrated in FIGS. 3 and 4, a generally rectangular shaped front bracket 56 is movably positioned in the recesses 48 that extend between each body member 20, 22. The front bracket 56 includes at least one slot 58 (see FIG. 3) that runs along a lateral or horizontal plane of the front bracket 56. A first pin 60 is positioned in the aperture 50 of the first body member 20 and a second pin 62 is positioned in the aperture 50 of the second body member 22. The first and second pins 60, 62 are positioned in the apertures 50 such that they extend through the slot 58 in the bracket 56. In one form, the first and second pins 60, 62 are press fit into the apertures 50 so that the pins 60, 62 are fixedly secured in the apertures 50. The pins 60, 62 are sized to travel in the slot 58 of the front bracket 56 thereby allowing the first and second body members 20, 22 to move between the expanded state illustrated in FIG. 3 and the contracted state illustrated in FIG. 4.

Figure 5:
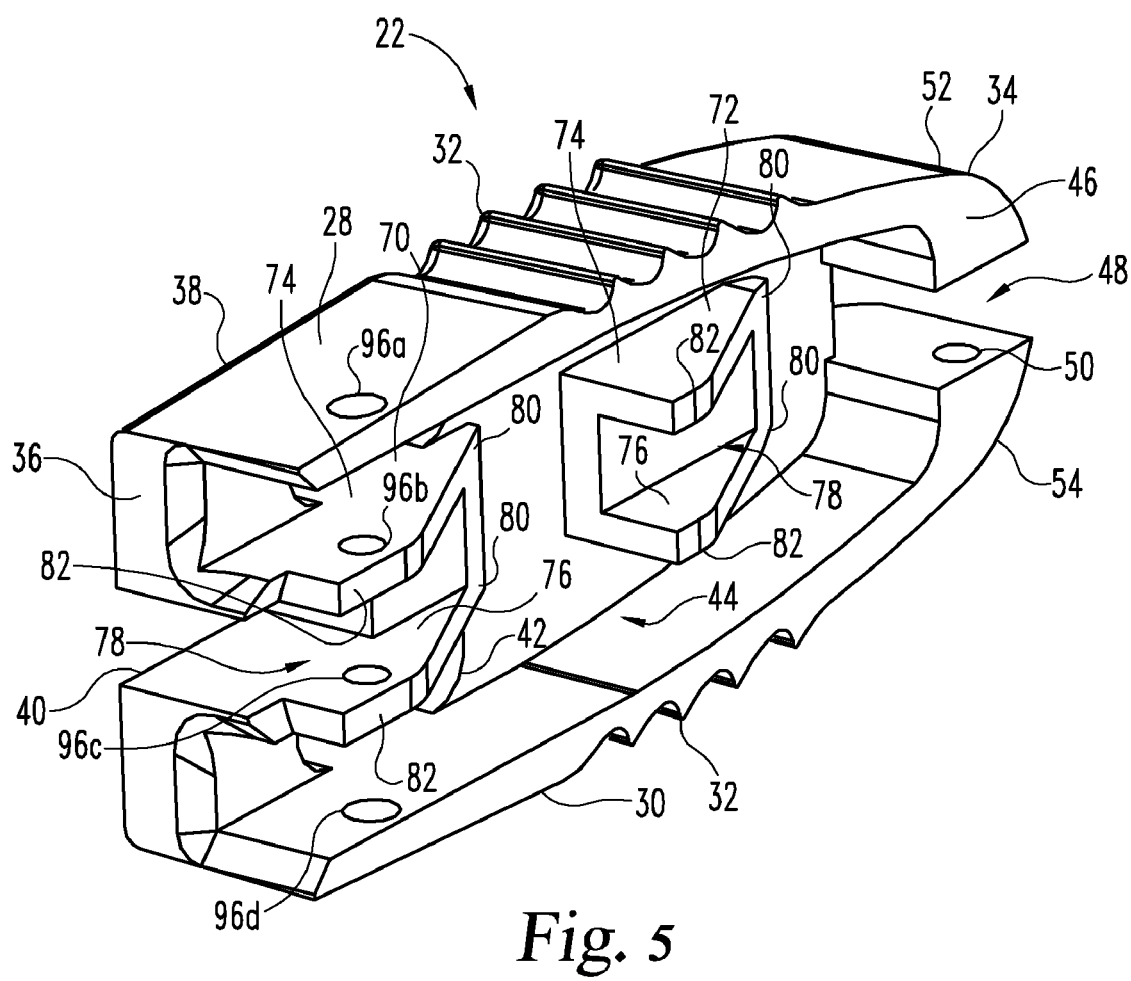
FIG. 5 is a perspective rear view of a body member of the implant illustrated in FIG. 2.

Referring collectively to FIGS. 2, 3 and 5, each respective body member 20, 22 includes a first or rear wedge member 70 and a second or front wedge member 72. As depicted, each wedge member 70, 72 protrudes inwardly from an internal surface of each respective sidewall 38 a predetermined distance into the interior space 44 defined by the first and second body members 20, 22. In this form, each wedge member 70, 72 includes an upper angular shelf 74 and a lower angular shelf 76 separated by a channel 78. The shelves 74, 76 have a front portion 80 that is located proximate an internal surface of each sidewall 38 that extends outwardly to a rear portion 82 that is located a predetermined distance away from the sidewall 38. As such, the front portion 80 of the shelves 74, 76 taper outwardly toward the rear portions 82 of the shelves 74, 76.

Referring to FIGS. 2 and 5, the implant 10 also includes a rear bracket 90 that includes first and second arms 92, 94 that are positioned between the channels or passages 78 defined by the rear wedge members 70 of the first and second body members 70, 72. As further illustrated, the upper surface 28 of each body member 20, 22, the rear portions 82 of the shelves 74, 76 of the wedge members 74, and the lower surface 30 of each body member 20, 22 each include an aperture or bore 96a-d running through them that is aligned along the same vertical axis. In addition, the first arm 92 of the rear bracket 90 includes a first slot 98 and the second arm 94 of the rear bracket 90 includes a second slot 100. To movably secure the rear bracket 90 in the channels 78 of the wedges 70 of the first and second body members 20, 22, first and second pins 102 are inserted through apertures 96b, 96c of the wedges 70 of each respective body member 20, 22 as well as the slots 98, 100 of the first and second arms 92, 94. In one form, apertures 96a, 96d have a larger diameter than apertures 96b, 96c so that the pins 102 can easily slide through apertures 96a, 96d. In another form, the pins 102 are sized to be press or friction fit into apertures 96b, 96c to secure the rear bracket 90 to the first and second body members 20, 22.

Referring to FIGS. 2-4, as previously set forth the implant 10 is operable to freely transition between an expanded and unexpanded state. In other words, the implant 10 is operable to laterally expand to the expanded state after being properly positioned between respective adjacent vertebral members $V_S$, $V_I$. The first and second body members 20, 22 are operable to translate laterally on the front and rear brackets 56, 90. This is accomplished because the body members 20, 22 are capable of sliding in the slots 58, 98, 100 of the front and rear brackets 56, 90. The pins 60, 62, 102 secure the body members 20, 22 in the slots 58, 98, 100 of the front and rear brackets 56, 90 and allow the body members 20, 22 to move laterally between the expanded and unexpanded state by travelling within the slots 58, 98, 100 of the front and rear brackets 56, 90.

Figure 6:
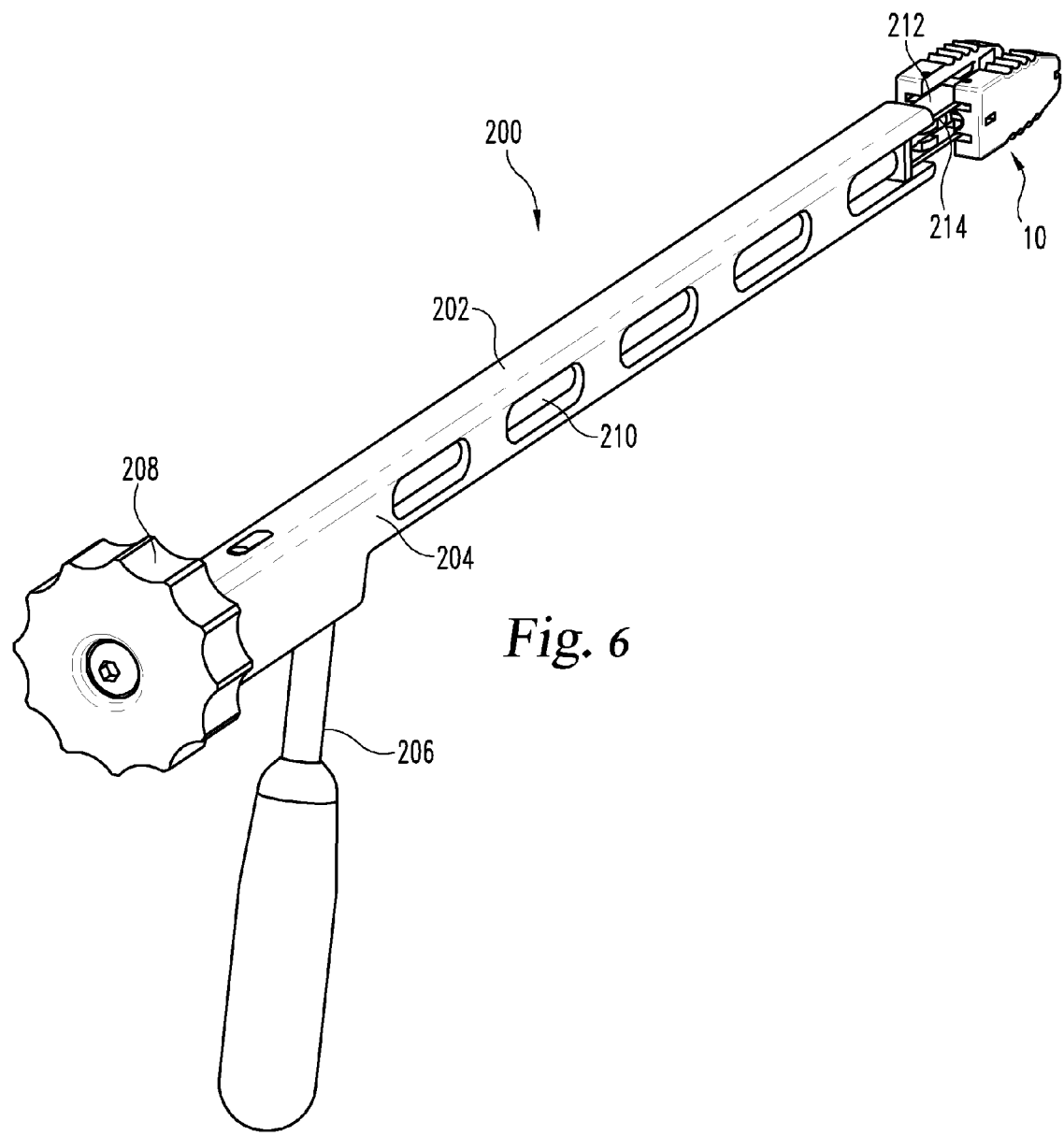
FIG. 6 is a perspective view of a spinal implant system including an instrument, expansion component, and implant illustrated in an expanded state for reception of the expansion element.

Referring to FIG. 6, a spinal implant system 200 is illustrated that includes an instrument 202 connected with the implant 10 illustrated in FIGS. 2-5. The instrument 202 includes a body 204, a handle 206, a dial or knob 208, and a hollow inner cylindrical sleeve or shaft 210. The system 200 also includes an expansion component 212 that is connected with the cylindrical shaft 210. Although not clearly illustrated in FIG. 6, the system 200 also includes a switching tube or stick 214 that is removably connected with the rear bracket 90 of the implant 10. In the illustrated form, the rear bracket 90 includes an internally threaded connector 91 (see FIG. 2) for connecting the switching stick or guide 214 to the implant 10. In one form, as the dial 208 is rotated it causes the inner shaft 210 to retract into the body 204 of the instrument 202 thereby also retracting the expansion component 212 into the body 204 of instrument 202.

Figure 7:
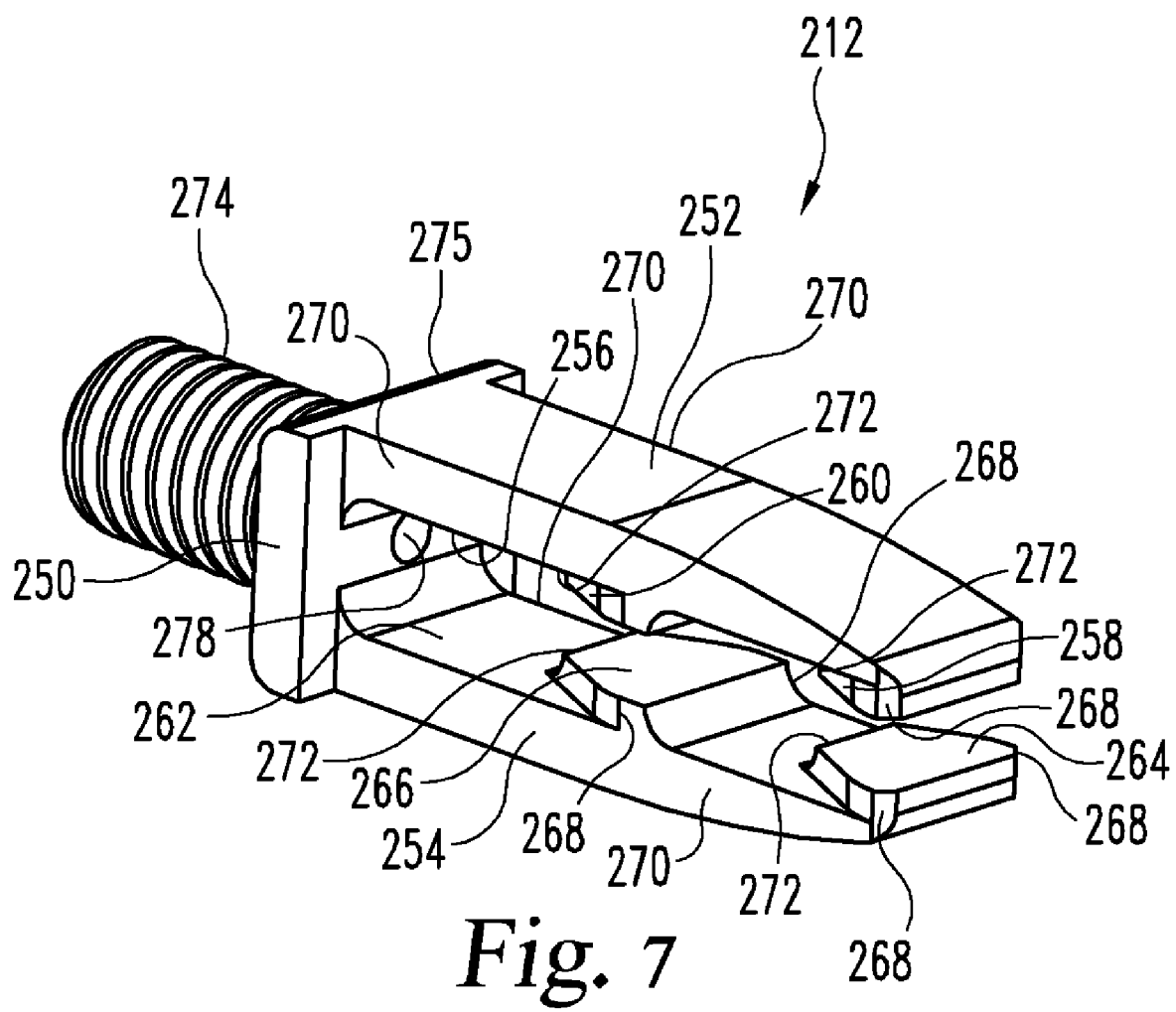
FIG. 7 is a perspective view of a representative expansion component.

Referring to FIG. 7, a perspective view of an illustrative expansion component 212 is depicted. The expansion component 212 includes a base plate 250 that has an upper expansion member 252 and a lower expansion member 254 extending away from the base plate 250. A lower surface 256 of the upper expansion member 252 includes a front inverted wedge member 258 spaced apart from a rear inverted wedge member 260. An upper surface 262 of the lower expansion member 254 includes a front inverted wedge member 264 spaced apart from a rear inverted wedge member 266. The inverted wedge members 258, 260, 264, 266 include a front portion 268 that begins at opposing respective sidewalls 270 of the upper and lower expansion members 252, 254 and tapers inwardly toward a rear portion 272. As will be discussed in greater detail below, the inverted wedge members 258, 260, 264, 266 are used to expand the implant 10 from an unexpanded state to an expanded state once inserted between adjacent vertebral members $V_S$, $V_I$.

The expansion component 212 also includes a hollow threaded connector 274 connected with and end 275 of the base plate 250. As illustrated, the base plate 250 of the expansion component 212 includes an aperture or bore 278 leading into the hollow interior of the hollow threaded connector 274. The aperture 278 is sized such that the switching stick 214 can be inserted through the aperture 278 and into and through the hollow threaded connector 274. In one form, the hollow threaded post 274 is used to connect the expansion component 212 to the inner shaft 210 of the instrument 202. As will be discussed in greater detail below, the inner shaft 210 comprises a hollow tube that is sized and configured to receive the switching stick 214. It should be appreciated that the expansion component 212 could be connected with the inner shaft 210 of the instrument 202 using other known interconnection methods and techniques (e.g.—press fit or friction fit) or could be made as an integral part of the instrument 202. In another form, the base plate 250 and upper and lower expansion members 252, 254 are sized and configured to be received within the body 204 of the instrument 202. As such, as the dial 208 is rotated the inner shaft 210 begins to retract the expansion component 212 which in turn, causes the implant 10 to expand. In addition, in this form as the expansion component 212 retracts it begins to move into the instrument body 204 as illustrated in FIG. 6.

Referring back to FIGS. 2 and 6, prior to insertion into the patient the implant 10 is placed in an expanded state so that the expansion component 212 can be inserted into the implant 10. The upper and lower expansion members 252, 254 of the expansion component 212 are sized and configured to be inserted into the implant 10. In particular, the upper and lower expansion members 252, 254 are inserted into passages 280 defined by the implant 10. A first set of upper passages 280a in the implant 10 are defined by the upper bone engaging surfaces 24, 28 of the first and second body members 20, 22 and the upper shelves 74 of the rear and front wedge members 70, 72. A second set of lower passages 280b are defined in the implant 10 by the lower bone engaging surfaces 26, 30 of the first and second body members 20, 22 and the lower shelves 76 of the rear and front wedge members 70, 72. The upper and lower expansion members 252, 254 are sized and configured to be inserted in the upper and lower passages 280a, 280b of the implant 10. See FIG. 6.

Figure 8:
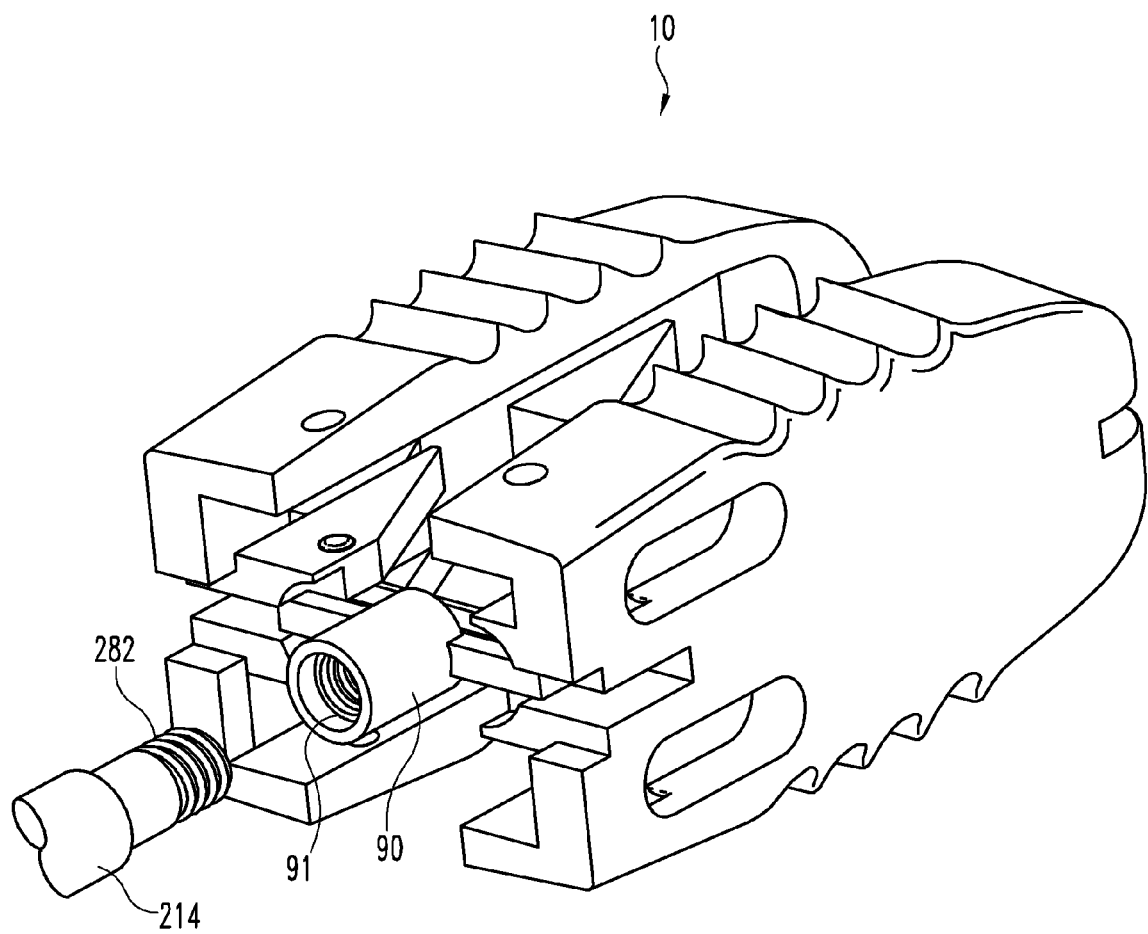
FIG. 8 is a perspective rear view of an implant and a portion of a switching stick.
Figure 9:
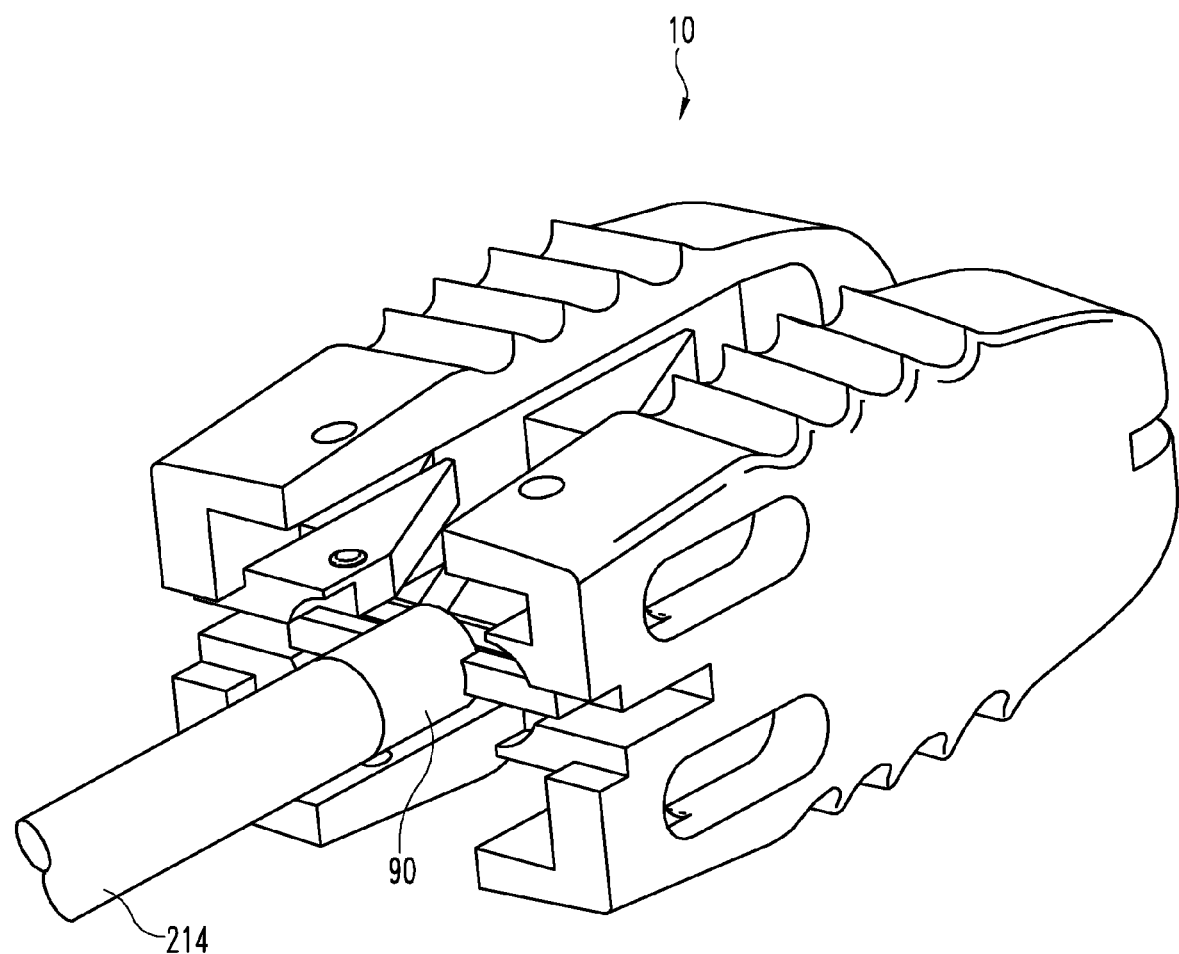
FIG. 9 is a perspective rear view of the switching stick connected to the implant.
Figure 10:
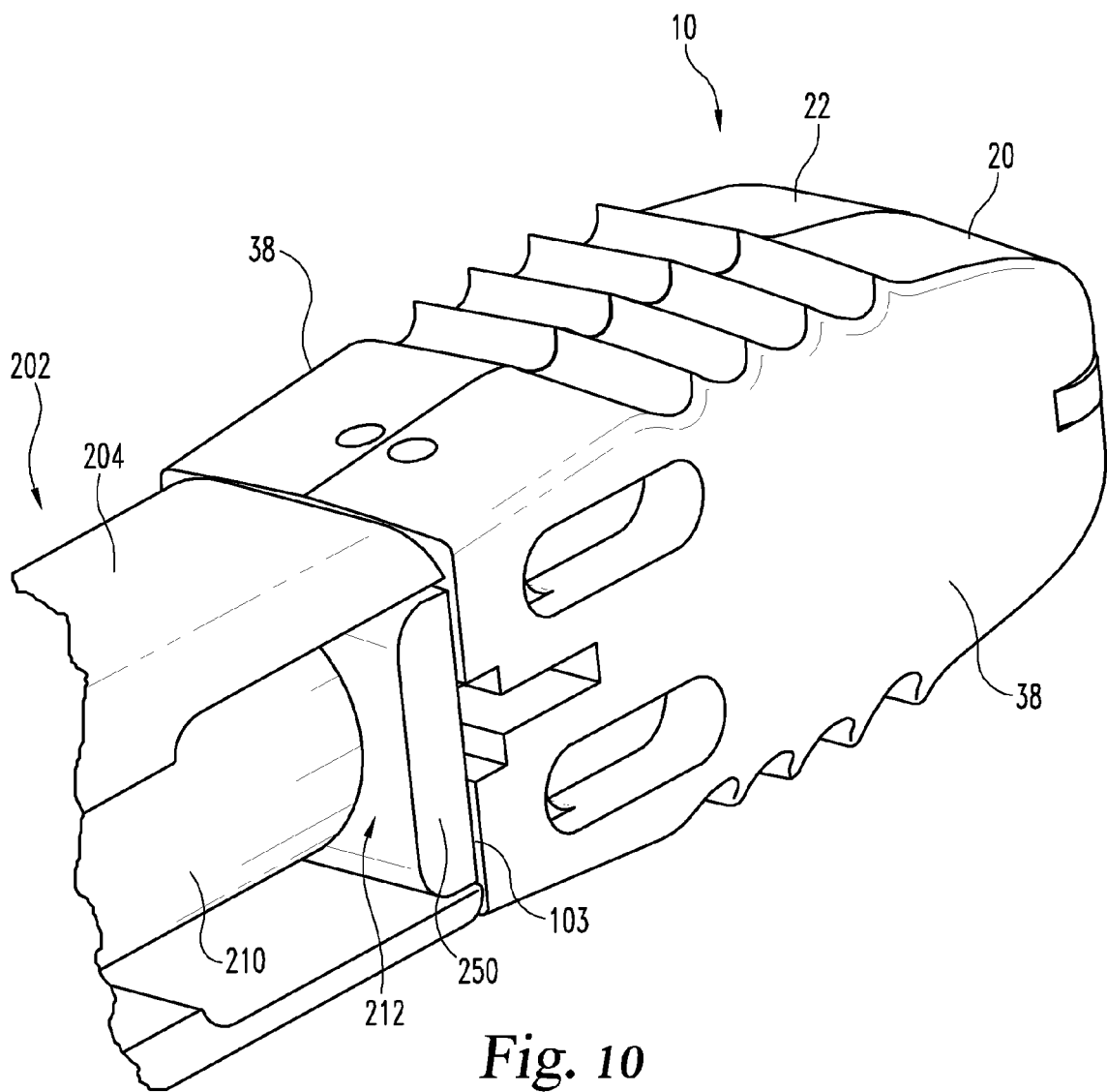
FIG. 10 is a perspective rear view of a portion of the instrument connected with the implant.
Figure 11:
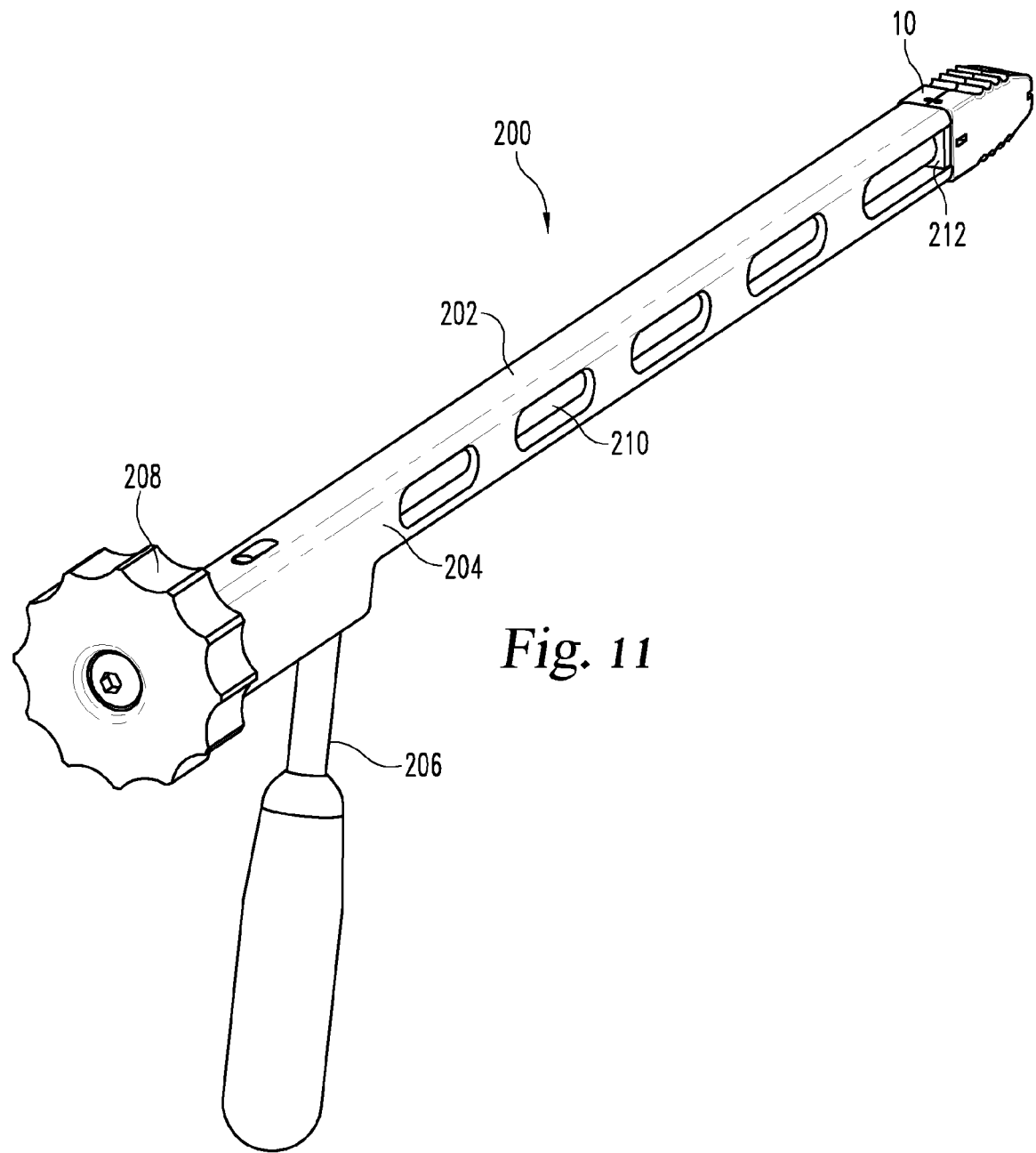
FIG. 11 is a perspective view of a spinal implant system including the instrument, expansion component, and implant illustrated in an expanded state encapsulating the expansion component.

Referring to FIGS. 8-9, a method of using the spinal implant system 200 disclosed herein will be discussed in greater detail. In this form, the switching stick 214 includes a threaded end 282 that is connected to an internally threaded connector 91 of the rear bracket 90. However, it should also be appreciated that other methods of connecting the switching stick 214 to the rear bracket of the implant 10 are contemplated. As illustrated in FIGS. 8-9, at some point either before or after the switching stick 214 is connected with the rear bracket 90, the implant 10 is placed in an expanded state. As illustrated in FIGS. 6 and 10, the expansion component 212 is then inserted into the passages 280a, 280b of the implant 10 until an end 103 of the implant 10 engages the rear plate 250 of the expansion component 212. As further illustrated in FIG. 10, at this point the implant 10 is placed in an unexpanded or collapsed state by pressing the sides 38 of the first and second body members 20, 22 together. Referring to FIG. 11, at this point the implant 10 is ready to be inserted into the patient between the adjacent vertebral members $V_S$, $V_I$.

Figure 12:
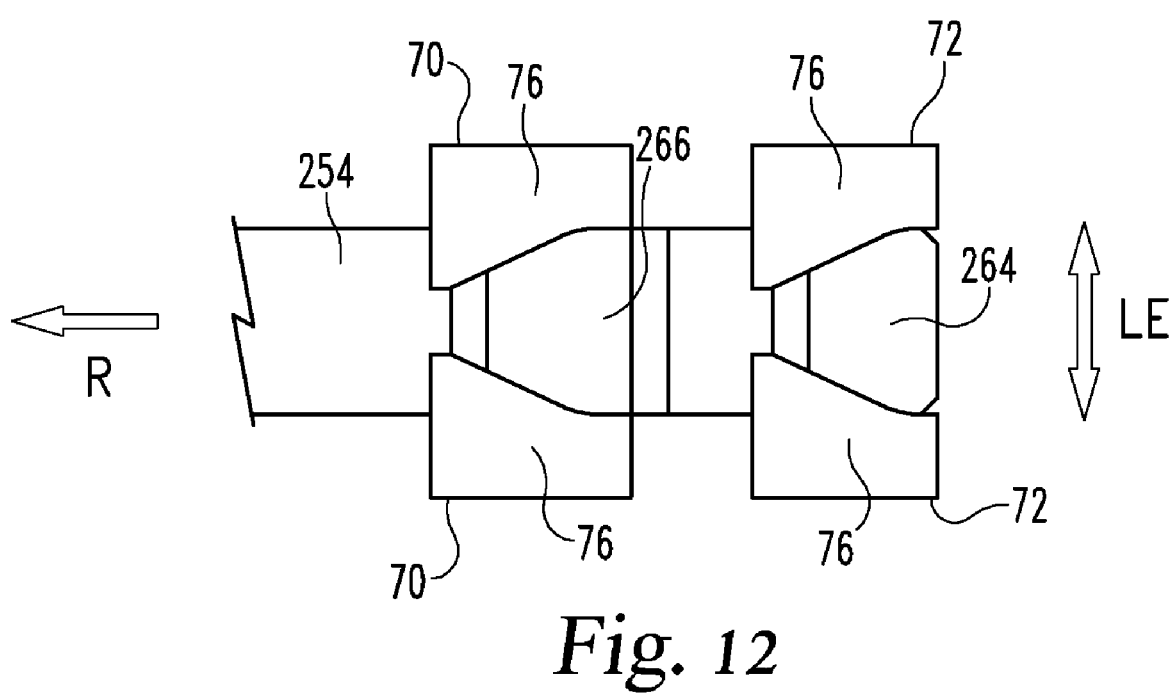
FIG. 12 is a top view of a portion of the implant and expansion component.

Referring to FIG. 12, a cross-sectional view of a portion of the implant 10 and the expansion component 212 in the assembled and unexpanded position is illustrated to gain an understanding of how the expansion component 212 expands the implant 10. In particular, a portion of the lower expansion member 254 is illustrated engaged with the lower shelves 76 of the rear and front wedges 70, 72 of the implant 10. As previously set forth, as the expansion component 212 is retracted by the instrument 202 in the direction indicated at R in FIG. 12, the inverted wedges 264, 266 of the expansion component 212 exert an outward or lateral force on the lower shelves 76 of the rear and front wedges 70, 72 of the implant 10. This force causes the implant 10 to expand laterally as indicated at LE in FIG. 12. Although not illustrated in FIG. 12, it should be appreciated that the inverted wedge members 258, 260 of the upper expansion member 252 engage the upper angular shelves 74 of the rear and front wedge members 70, 72 in a similar manner thereby also providing a laterally expanding force to the implant 10. As such, the inverted wedge members 258, 260, 264, 266 of the expansion component 212 and the rear and front wedge members 70, 72 of the implant 10 cooperate with one another to expand the implant laterally once placed between adjacent vertebral members $V_S$, $V_I$.

Figure 13A:
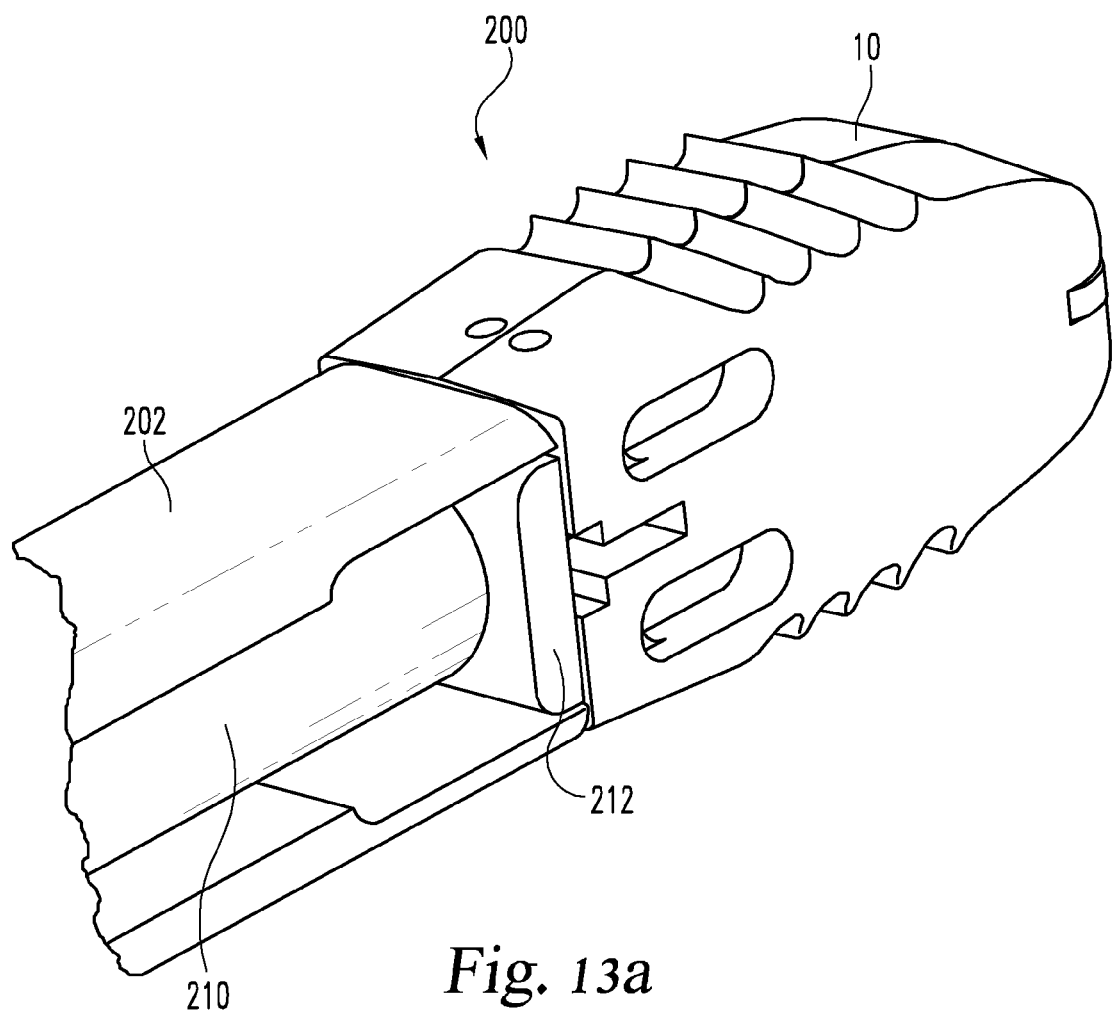
FIGS. 13a-f illustrate a portion of the instrument inserting and withdrawing the expansion component from the implant.
Figure 13B:
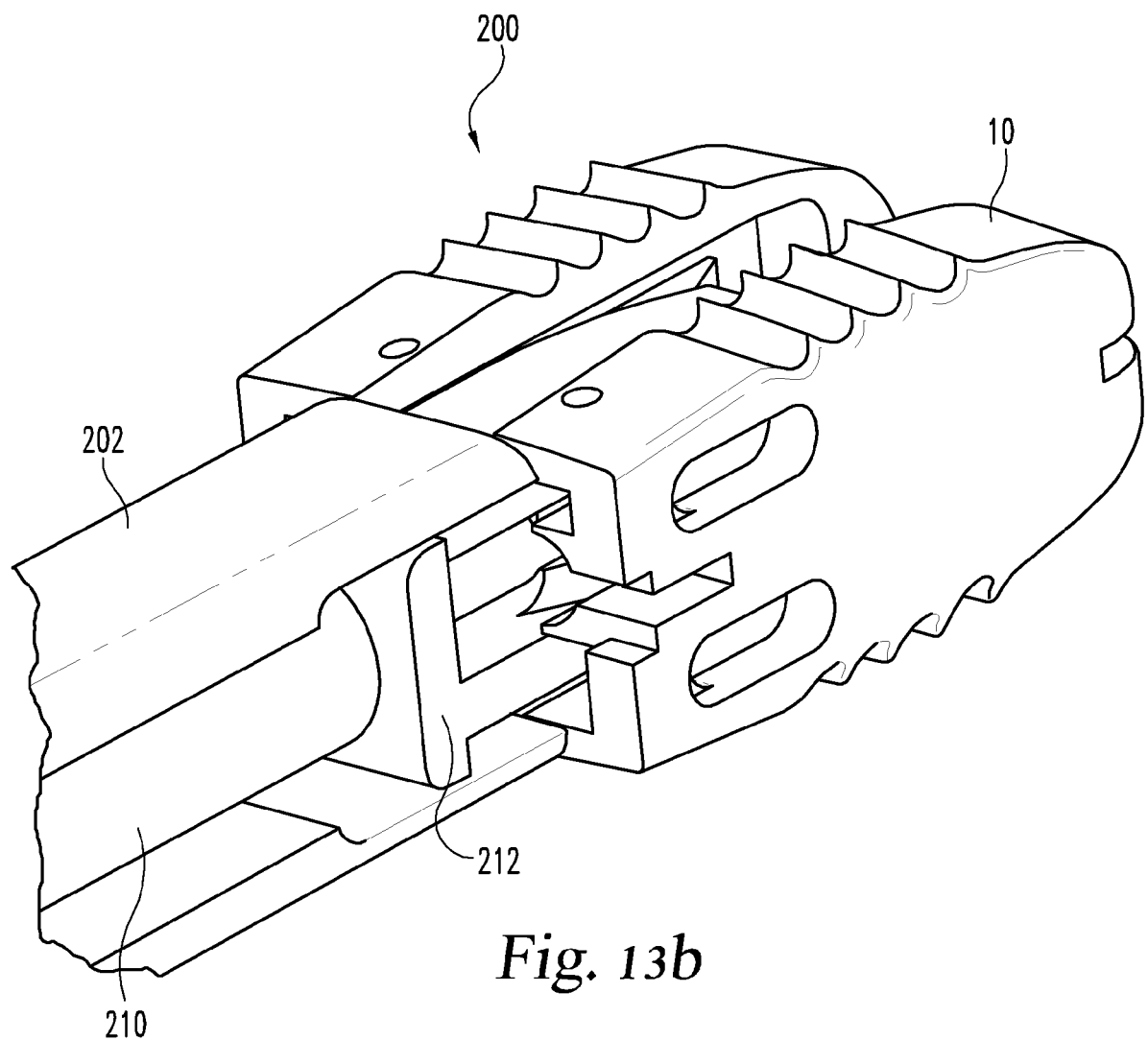
Figure 13C:
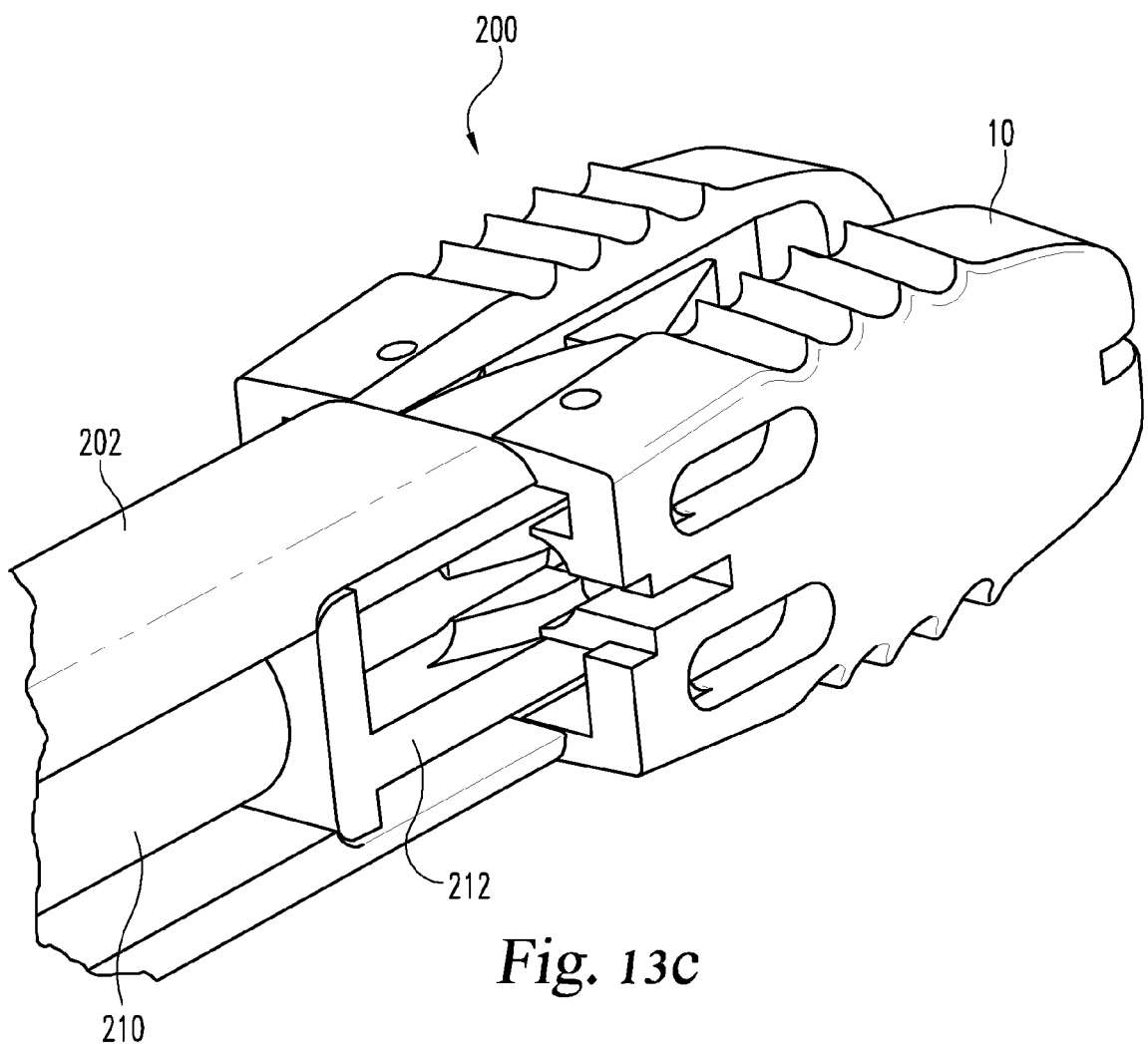
Figure 13D:
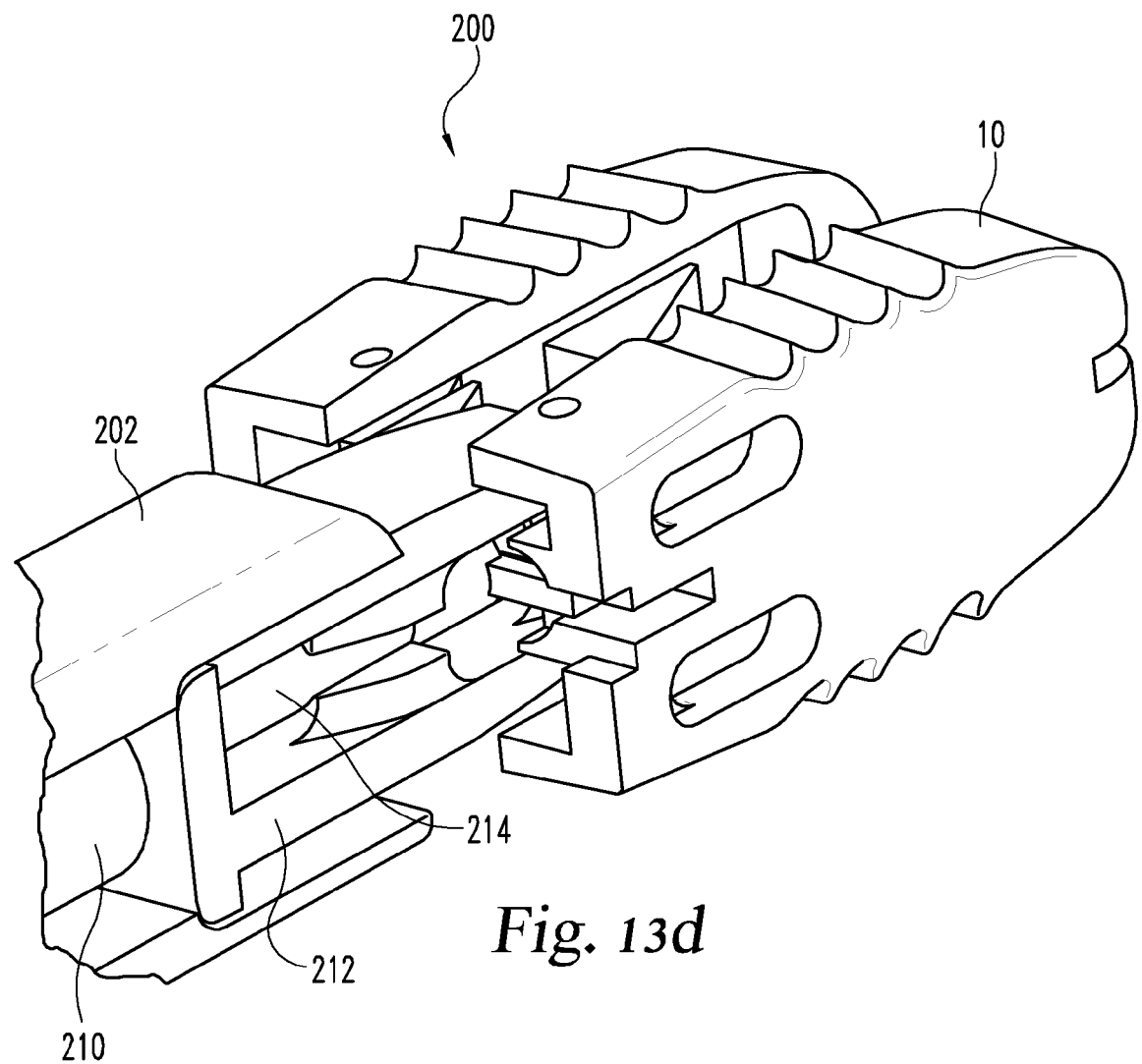
Figure 13E:
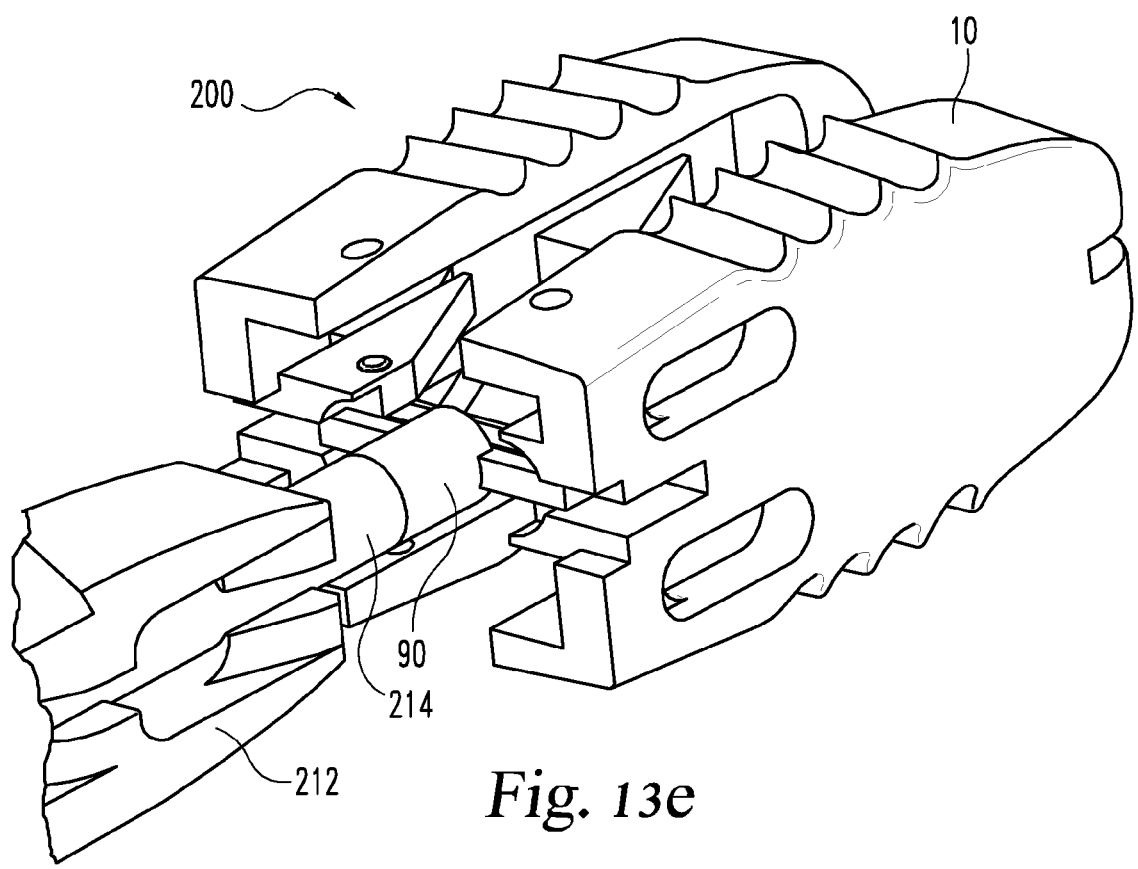
Figure 13F:
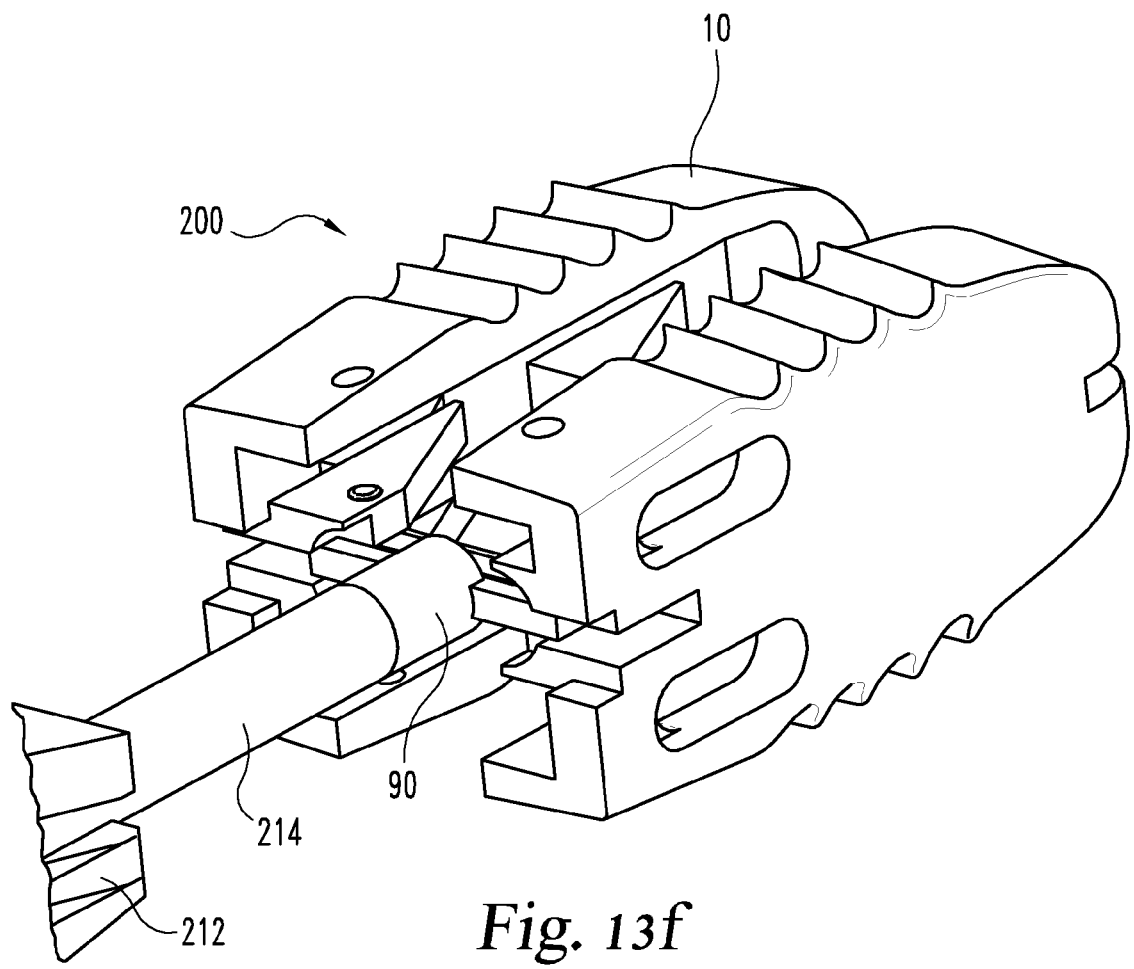

Referring to FIGS. 13a-13f, a more detailed illustration of the implant 10 expanding during implantation into a patient is set forth. In FIG. 13a the implant 10 has been inserted between adjacent vertebral members $V_S$, $V_I$ as described with respect to FIG. 1. As previously set forth, the implant 10 is inserted in the retracted or unexpanded state. Once the implant 10 is placed in the desired location between adjacent vertebral members $V_S$, $V_I$, the dial 208 of the instrument 202 is rotated thereby causing the inner shaft 210 to start pulling the expansion component 212 out of the implant 10. As illustrated in FIGS. 13b-13f, as the expansion component 212 is removed or drawn out of the implant 10, the implant 10 expands laterally until the expansion component 212 is removed from the implant 10. At this point, the instrument 202 can be removed from the patient and the implant 10 will remain in the expanded state between adjacent vertebral members $V_S$, $V_I$. As illustrated in FIG. 13f, the switching stick 214 is still connected with the rear bracket 90. The expansion member 202 travels on the switching stick 214 as the switching stick 214 is inserted into the aperture 278 and through the hollow connector 274 of the expansion member 212 and into the hollow inner shaft 210 of the instrument 202. The switching stick 214 is shown here as a rigid shaft, but it could also be constructed of other designs such as a flexible wire or cable.

Figure 14A:
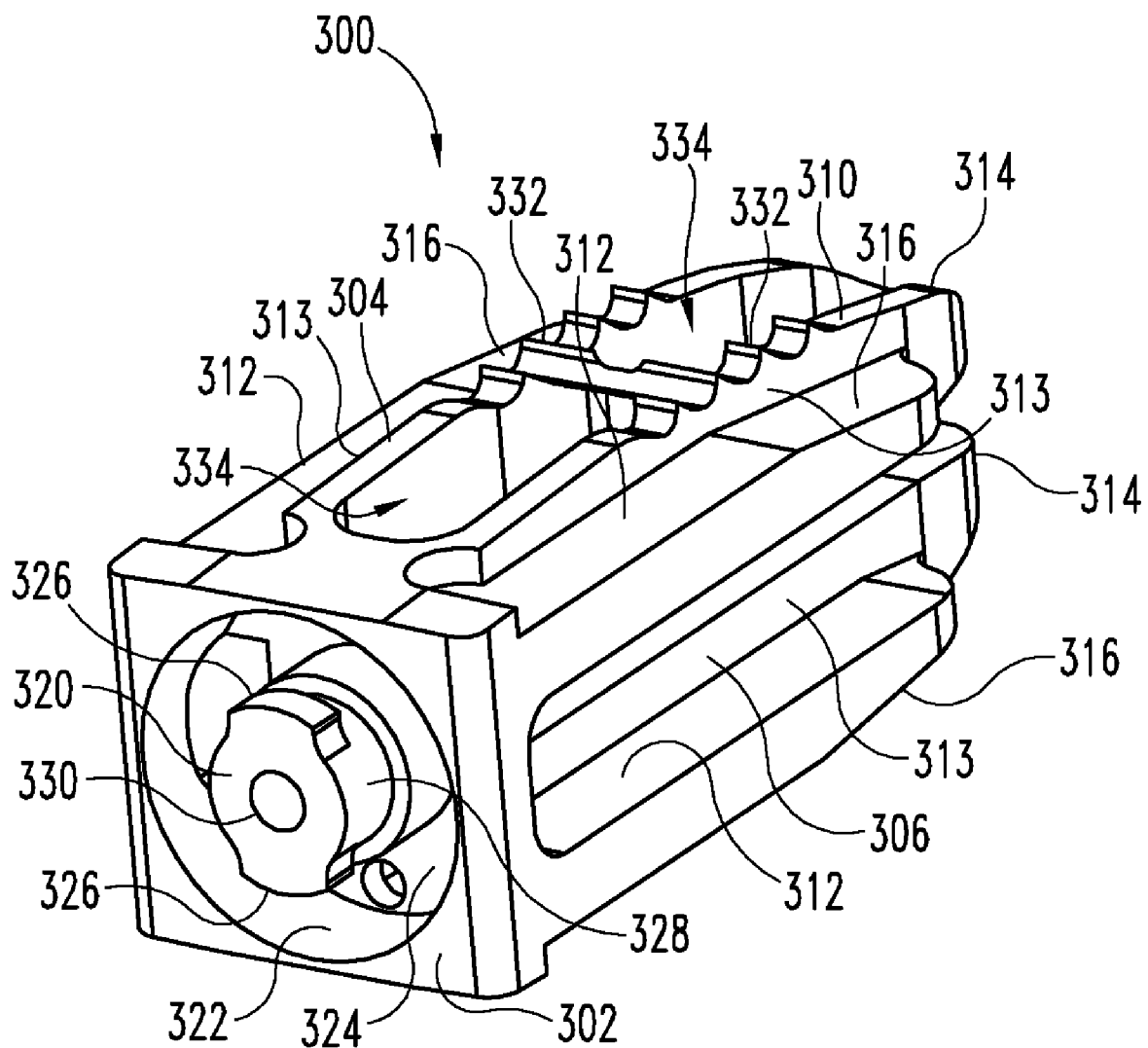
FIGS. 14a-b illustrate perspective views of a representative bone graft member.
Figure 14B:
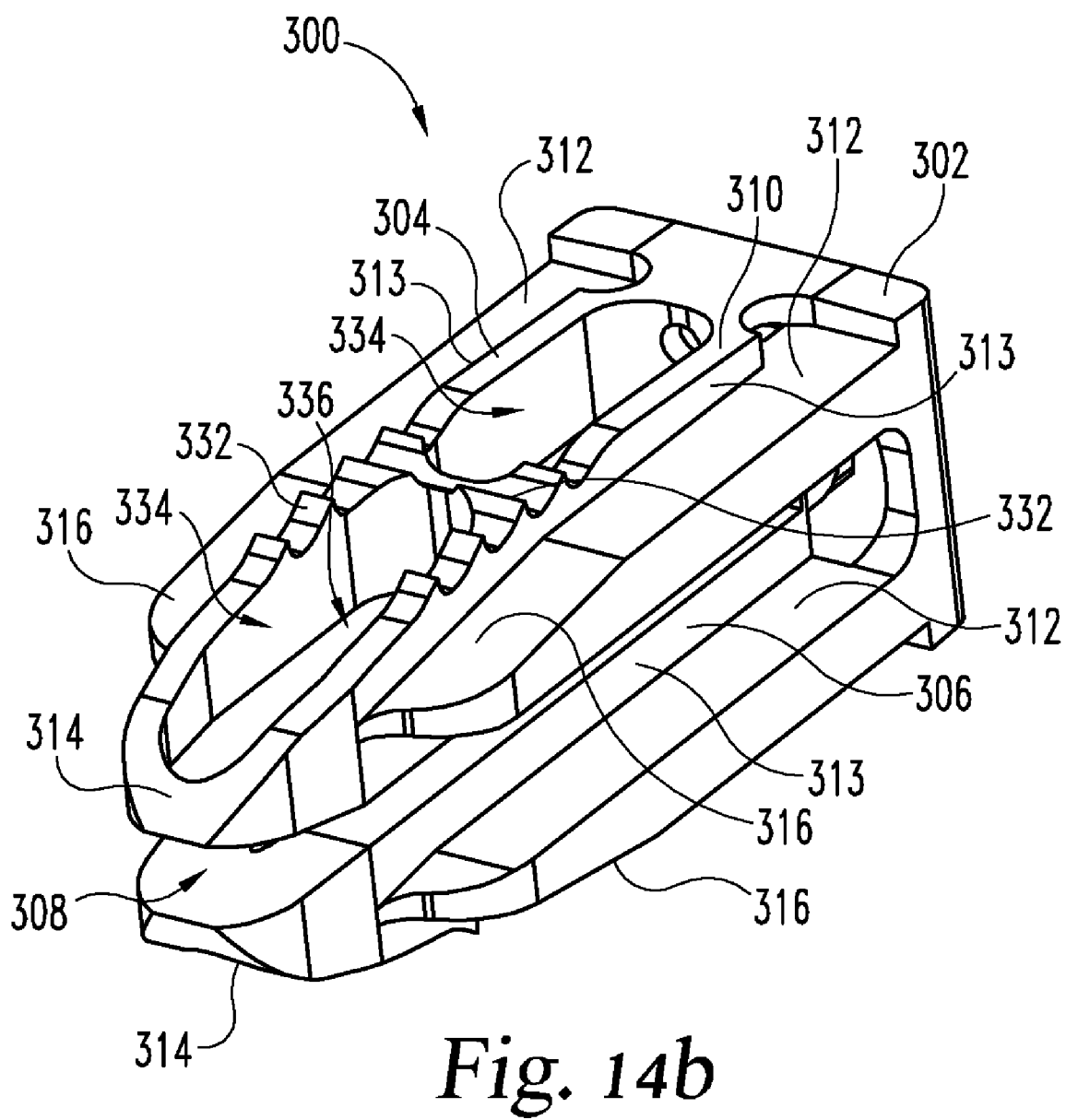

Referring to FIGS. 14a and 14b, a bone graft member or component 300 is illustrated that is configured to be inserted between the void or space created between the body members 20, 22 of the implant 10 when positioned in the expanded state. The bone graft member 300 includes a back or rear base plate 302 and an upper extension member 304 and a lower extension member 306 extending horizontally away from the rear base plate 302. The upper and lower extension members 304, 306 are separated by a channel or passageway 308. The upper and lower extension members 304, 306 include a bone engaging portion 310 that is configured to engage the endplates 17, 19 of the adjacent vertebral members $V_S$, $V_I$. In addition, a pair of retaining lips or ridges 312 extend outwardly from at least a portion of each side surface 313 of the bone engaging portion 310. In one form, the retaining lips 312 extend from the rear plate 302 to approximately a distal end 314 of each respective extension member 304, 306. In addition, the retaining lips 312 also include a sloped end 316 located toward the distal end 314 to facilitate insertion into the implant 10. Although the bone graft member 300 is referred to as a separate element herein, it should be appreciated that once inserted into the implant 10, the bone graft member 300 becomes part of the implant 10.

The rear plate 302 of the bone graft member 300 also includes a connector 320 that is positioned in a recess 322 in the rear plate 302. The connector 320 extends outwardly from a mounting portion 324 and has a generally circular shape with a hollow interior. In this form, the connector 320 includes a pair of detents 326 extending outwardly from a cylindrical central portion 328 of the connector 320. As described in detail below, a central portion of the connector 320 includes an aperture 330 passing into the hollow interior of the connector 320 that is sized and configured to receive the switching stick 214. The bone graft member 300 is configured to slide down the switching stick 214 when being implanted in the implant 10. When assembled on the implant 10, the hollow interior of the connector 320 is adapted to receive the internally threaded connector 91 of the rear bracket 90. The upper and lower expansion members 304, 306 also include bone engaging members 332. The bone engagement members 332 can comprise grooves, recesses, ridges, serrations, knurlings, spikes, roughened surfaces, or smooth surfaces for engaging the endplates of the adjacent vertebrae. In addition, the upper and lower expansion members 304, 306 also include a plurality of elongated passages 334, having a generally oval shape in this form, that expose an interior cavity 336 defined by the bone graft member 300. The elongated passages 334 are sized and configured to receive bone grafts for assisting in the fusion process.

Figure 15A:
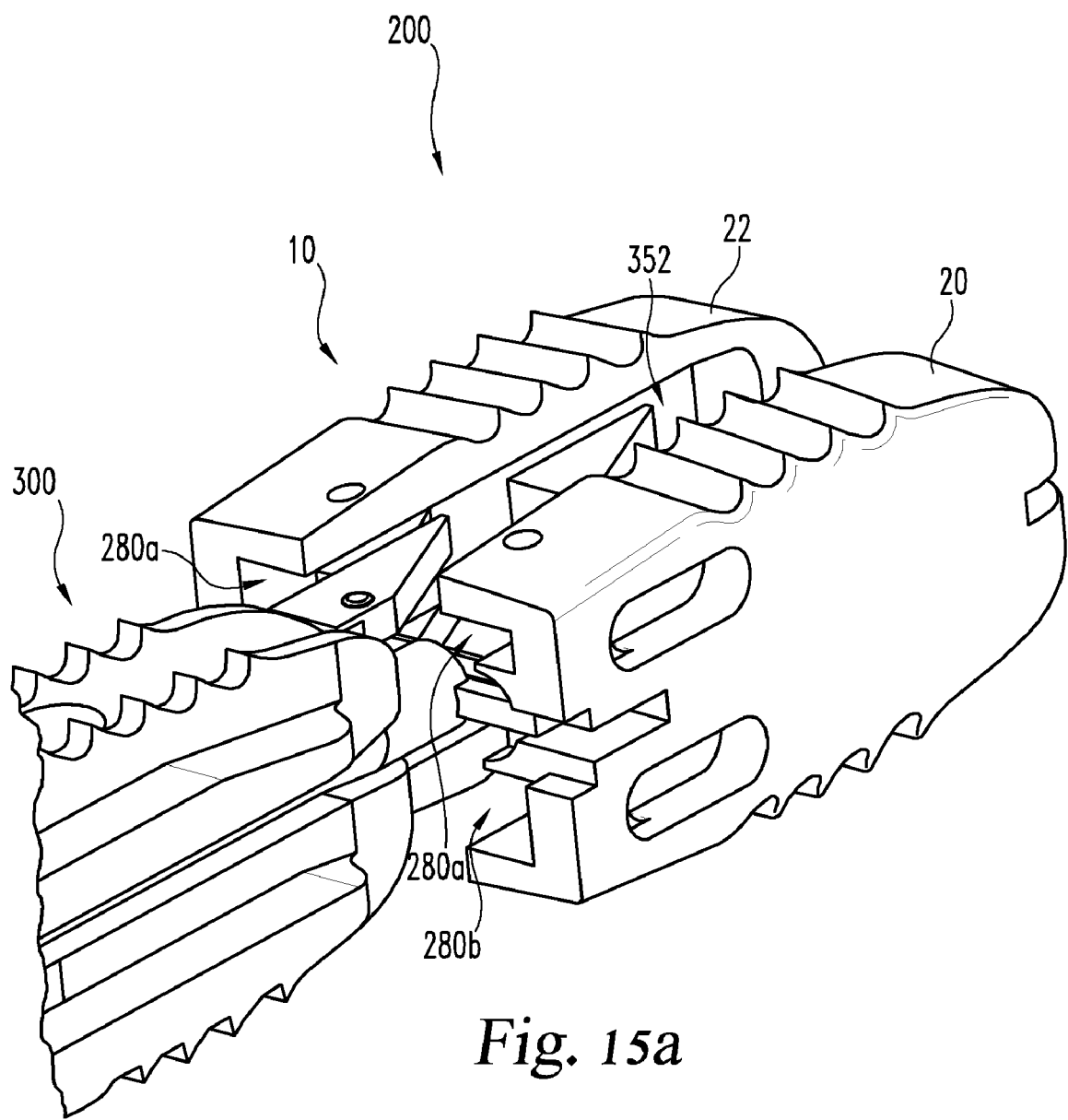
FIGS. 15 a-f illustrate perspective views of the bone graft member being inserted into the implant with a second instrument.
Figure 15B:
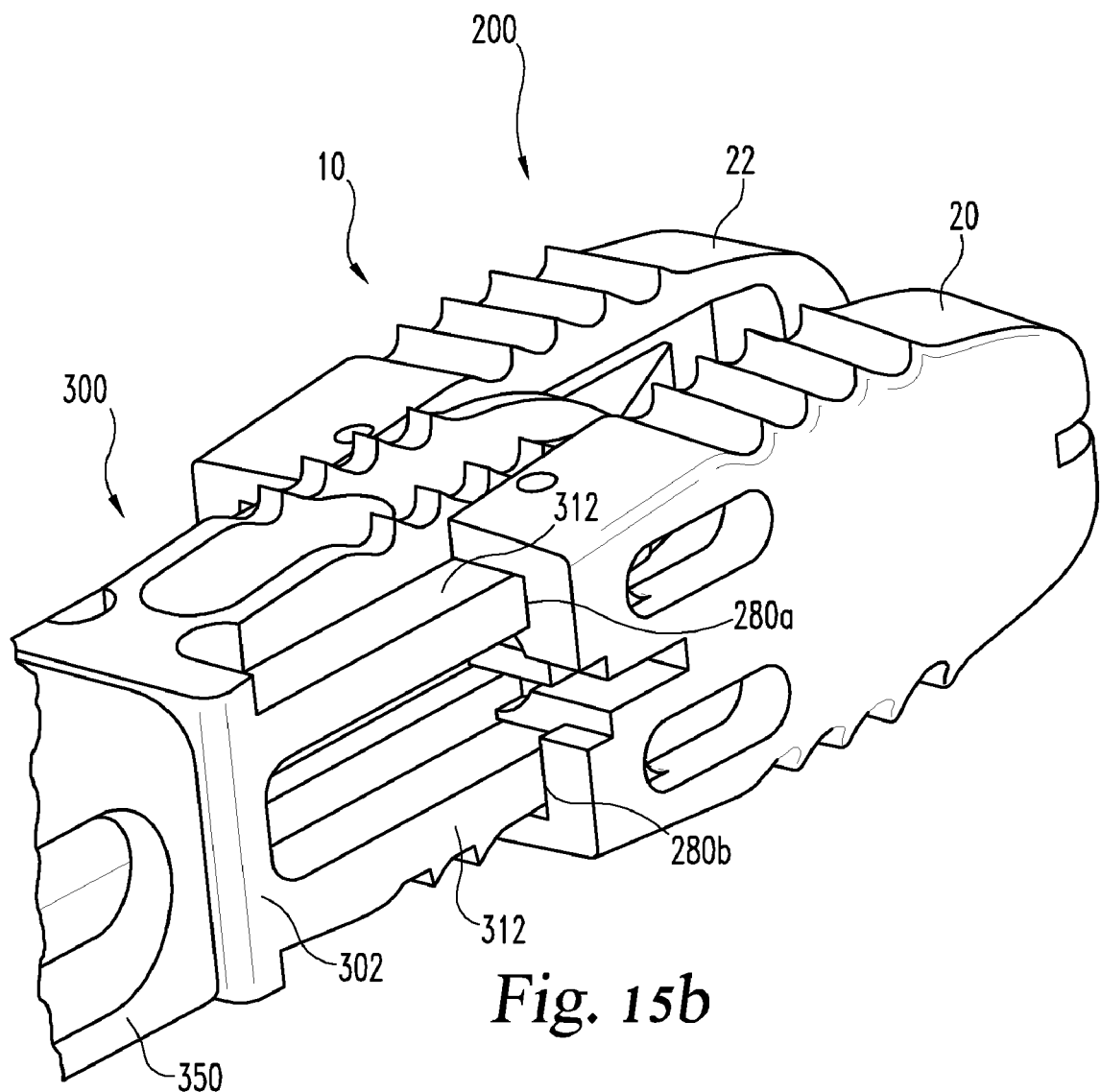
Figure 15C:
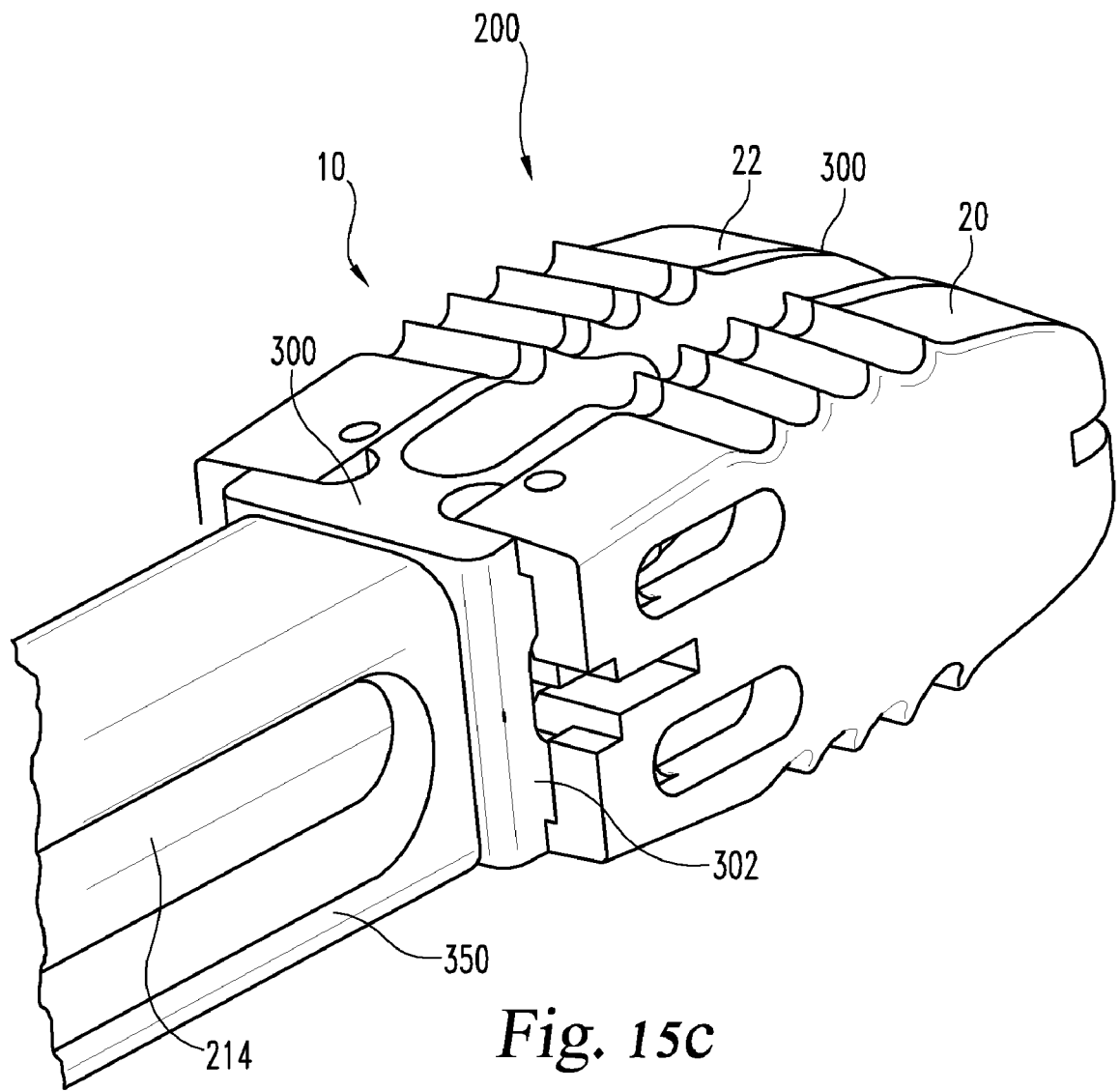

Referring to FIGS. 15a-15f, the insertion of the bone graft member 300 into the implant 10 after the implant 10 has been inserted between the adjacent vertebral members $V_S$, $V_I$ will be discussed in further detail. As illustrated in FIGS. 15a-15c, in this form the bone graft member 300 is connected with a second instrument 350. The second instrument 350 includes a hollow interior to receive the switching stick 214. As previously set forth, the connector 320 of the bone graft member 300 includes an aperture 330 that allows the switching stick 214 to pass through the bone graft member 300 such that it can slide down the switching stick 214 towards the implant 10. In the expanded state, the implant 10 defines a gap or void 352 (see FIG. 15a) between the respective body members 20, 22. The bone graft member 300 is sized and configured to fit in the gap 352 thereby securely locking the implant 10 in the expanded state.

As illustrated in FIGS. 15a-15c, each respective body member 20, 22 defines internal upper and lower passages 280a, 280b. In this form, the passages 280a, 280b have a generally half-rectangular shape that are sized and configured to receive the lips 312 of the bone graft member 300. It should be appreciated that passages 280a, 280b could be formed in other configurations as well. As the bone graft member 300 is slid down the switching stick 214, the lips 312 of the bone graft member 300 come into alignment with the passages 280a, 280b. The lips 312 secure the bone graft member 300 in the implant 10. Once the second instrument 350 pushes the rear plate 302 of the bone graft member 300 against the proximal end 36 of the implant 10, the bone graft member 300 is securely positioned within the implant 10. In one form, the bone graft member 300 is press fit into the implant 10 and in other forms, detents or locking members may be employed to secure the bone graft member 300 within the implant 10. As further illustrated, once inserted the upper and lower bone engaging portions 310 align with the bone engaging surfaces 24, 26 of the implant 10.

Figure 15D:
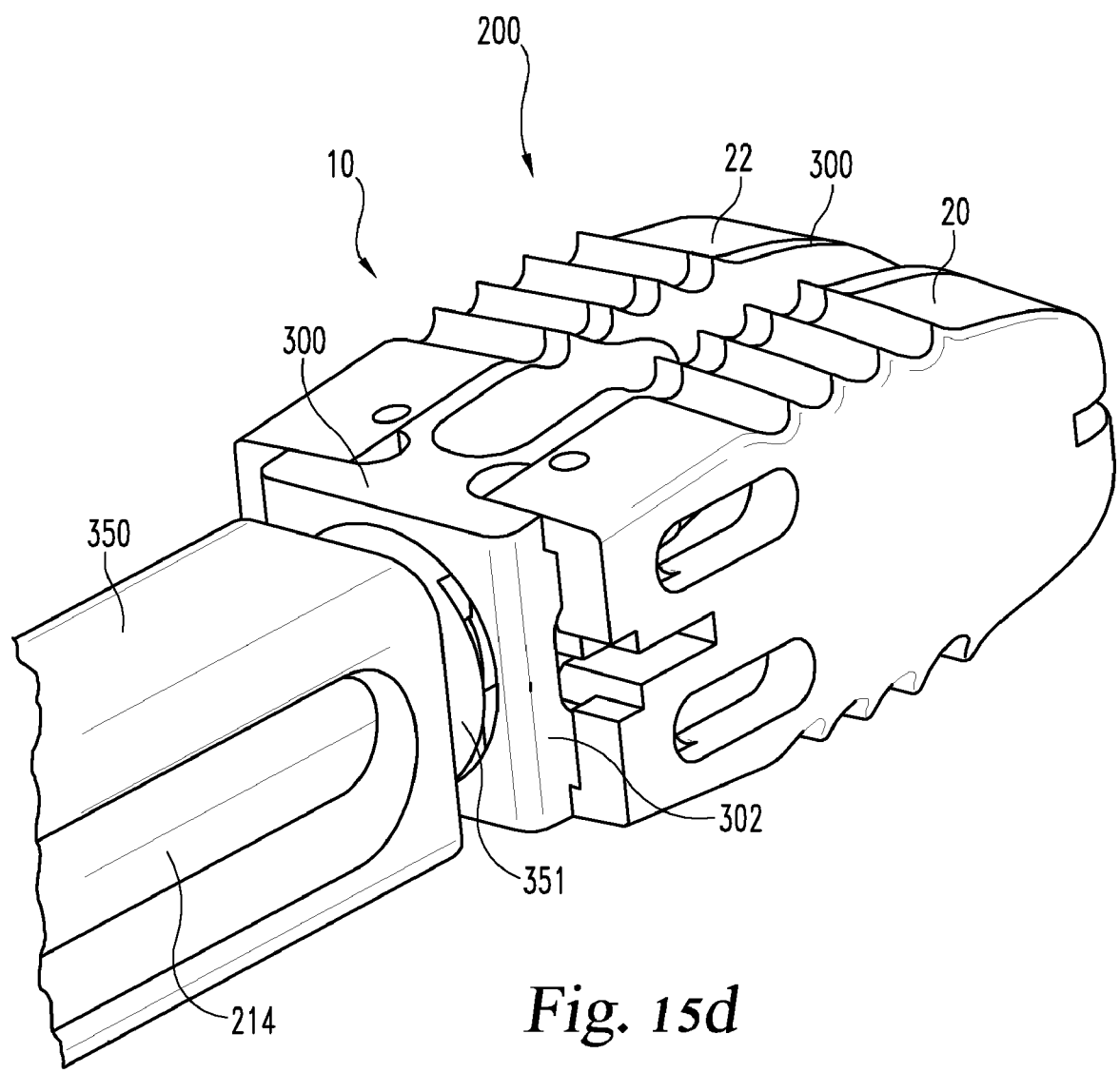
Figure 15E:
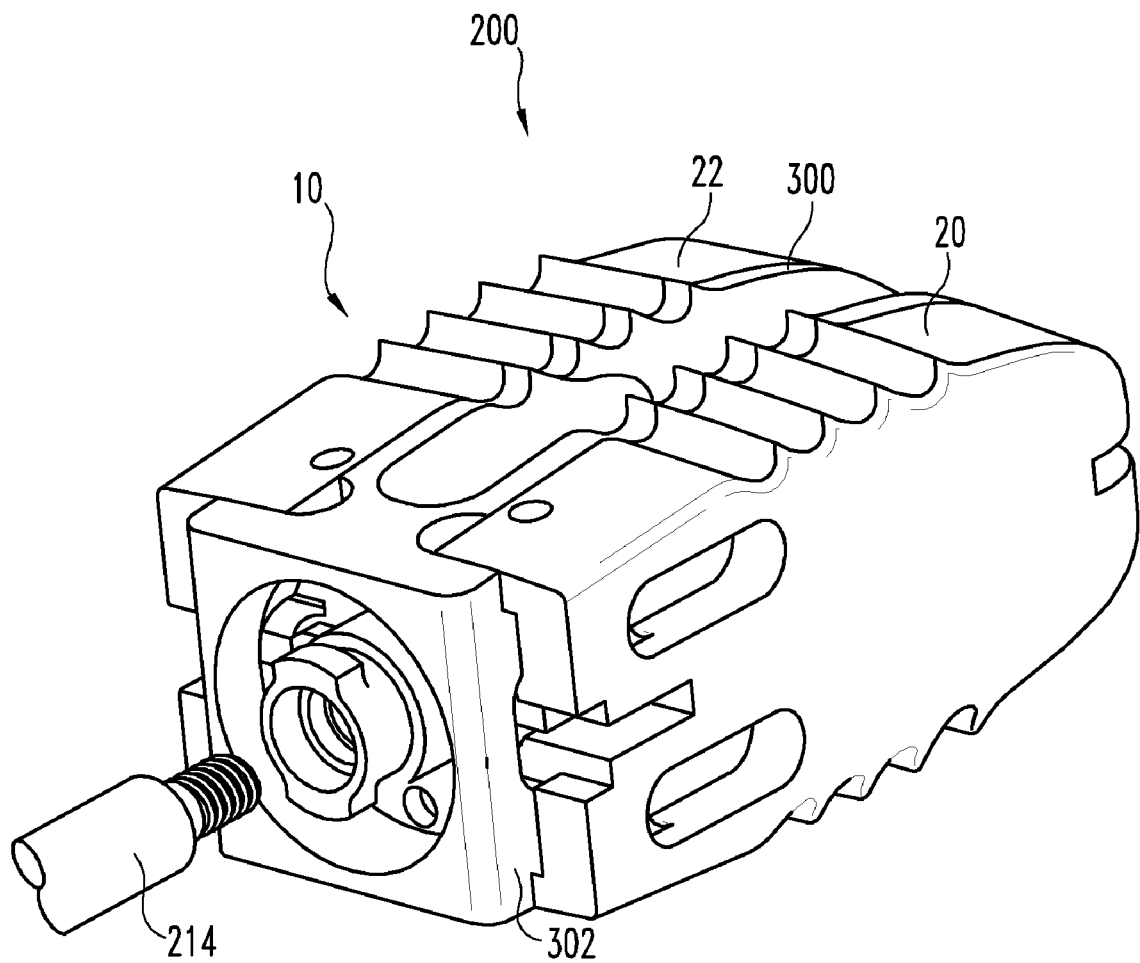
Figure 15F:
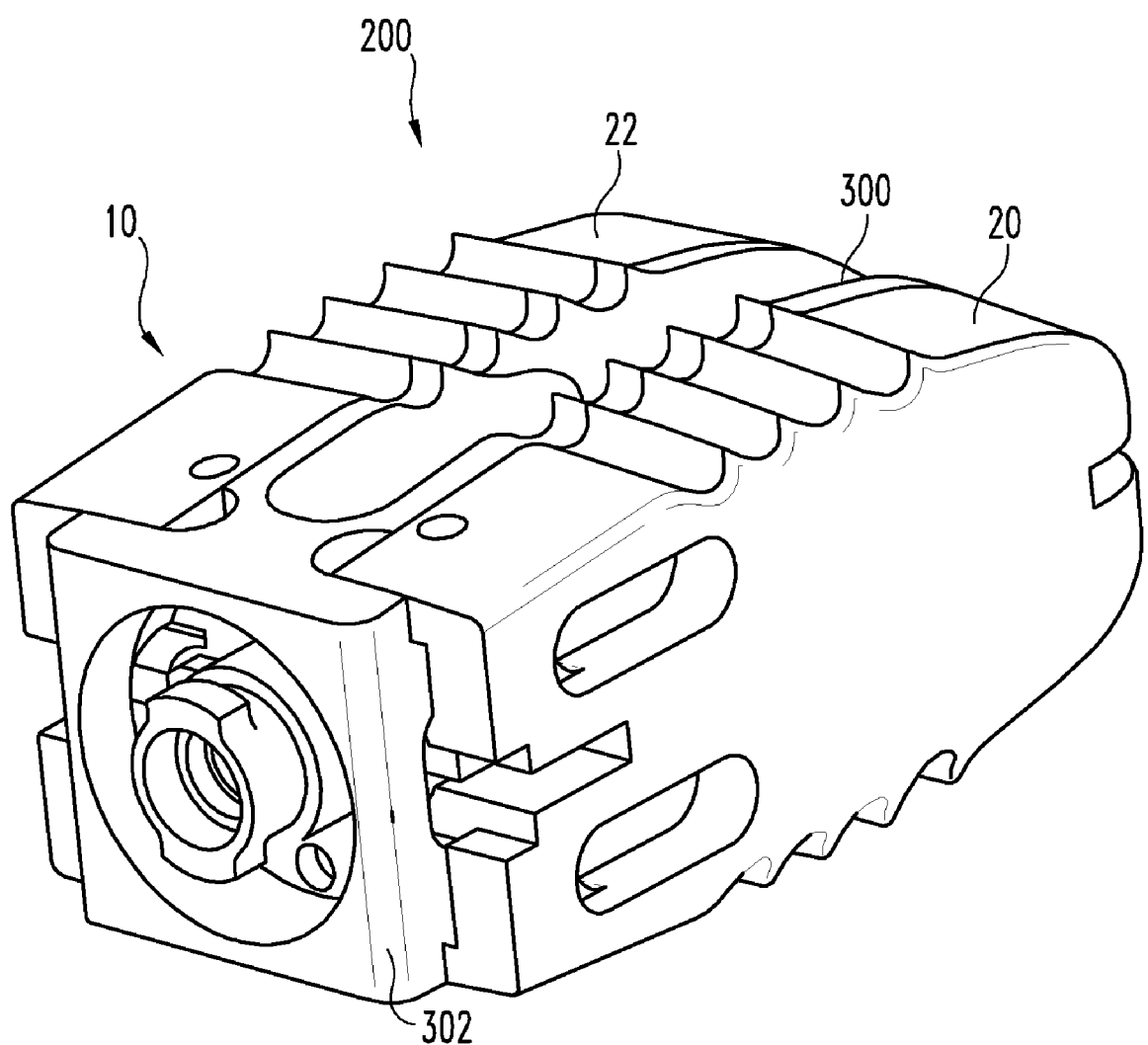

As illustrated in FIG. 15d, the second instrument 350 may then be rotated about its horizontal axis approximately 90° thereby disconnecting the second instrument 350 from the bone graft member 300. Rotating the second instrument 350 about its horizontal axis causes a female connector or receptacle 351 of the second instrument 350 to disengage the detents 326 thereby allowing the second instrument 350 to be disconnected from the bone graft member 300 and slid out of the patient. As illustrated in FIG. 15e, the switching stick 214 can then be disconnected from the connector 91 of the rear bracket 90 and removed from the patient. Bone growth material can then be injected into and around the implant 10 to help the fusion process.

In one form of the present invention, prior to insertion between the endplates of the adjacent vertebral members $V_S$, $V_I$, the implant 10 has a width of approximately 10-12 millimeters in the unexpanded or retracted state. Once the implant 10 is inserted into the patient, the implant 10 is expanded to a width of approximately 16-18 millimeters. As such, the implant 10 disclosed herein is capable of providing a much wider footprint thereby providing better fusion of adjacent vertebral members $V_S$, $V_I$. Further, because the implant 10 is expanded after insertion, the implant 10 will not migrate out of the channel utilized to insert the implant 10.

Figure 16:
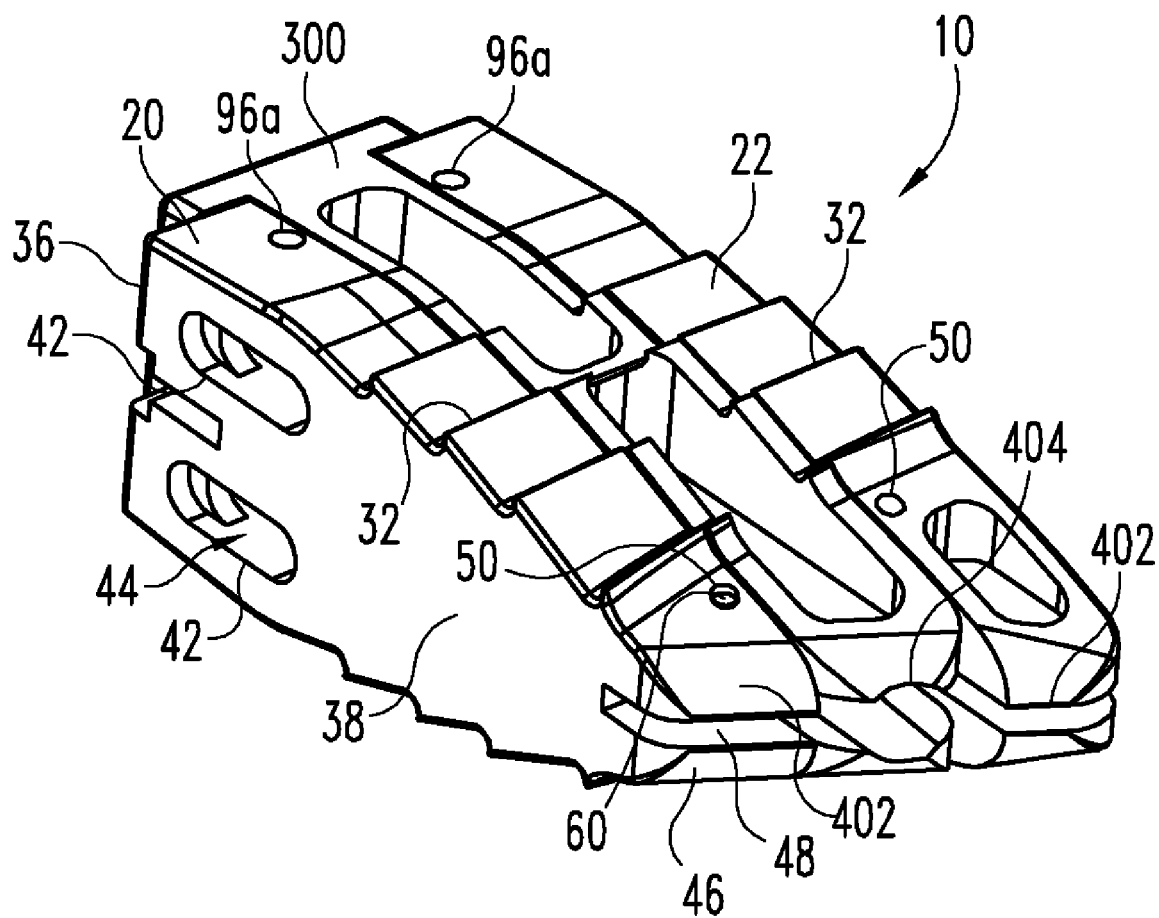
FIG. 16 illustrates another representative implant having a bone graft member inserted between the first and second bodies of the implant.
Figure 17:
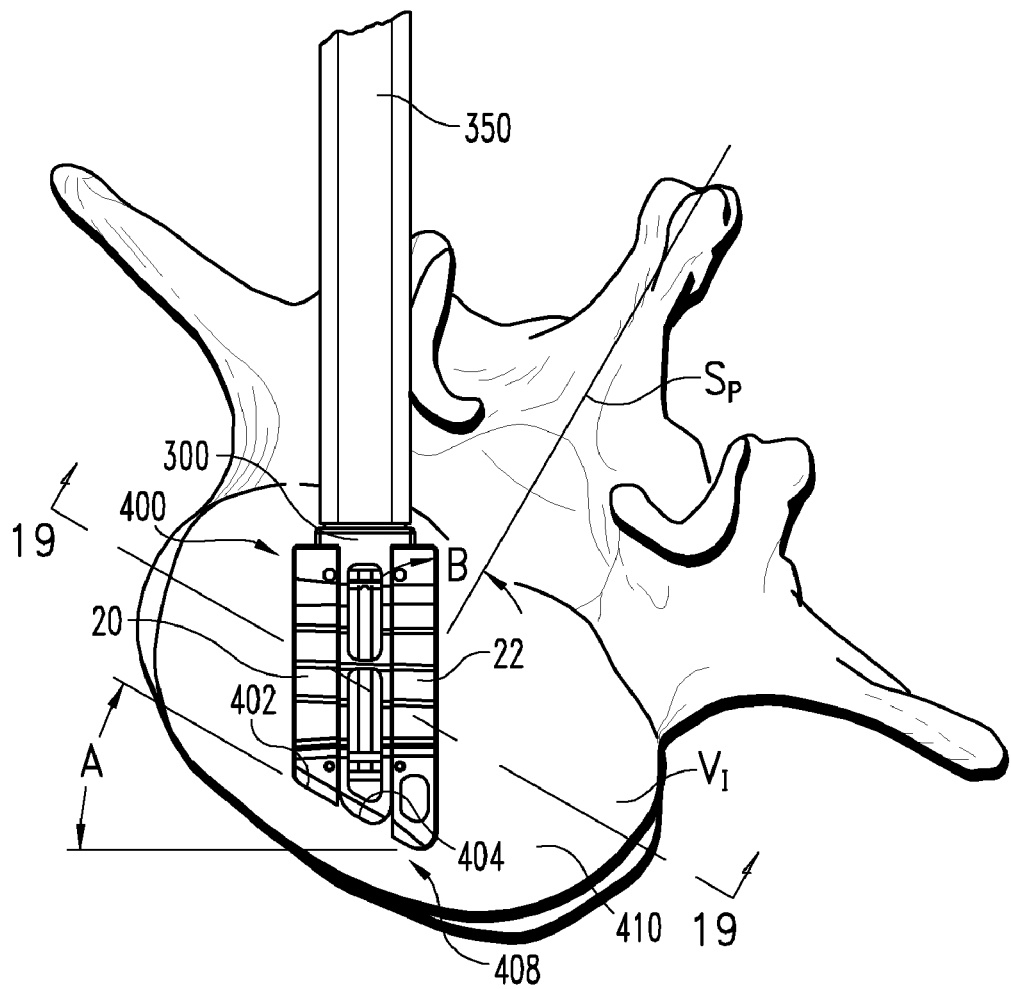
FIG. 17 illustrates the implant illustrated in FIG. 16 inserted from an oblique approach.
Figure 18:
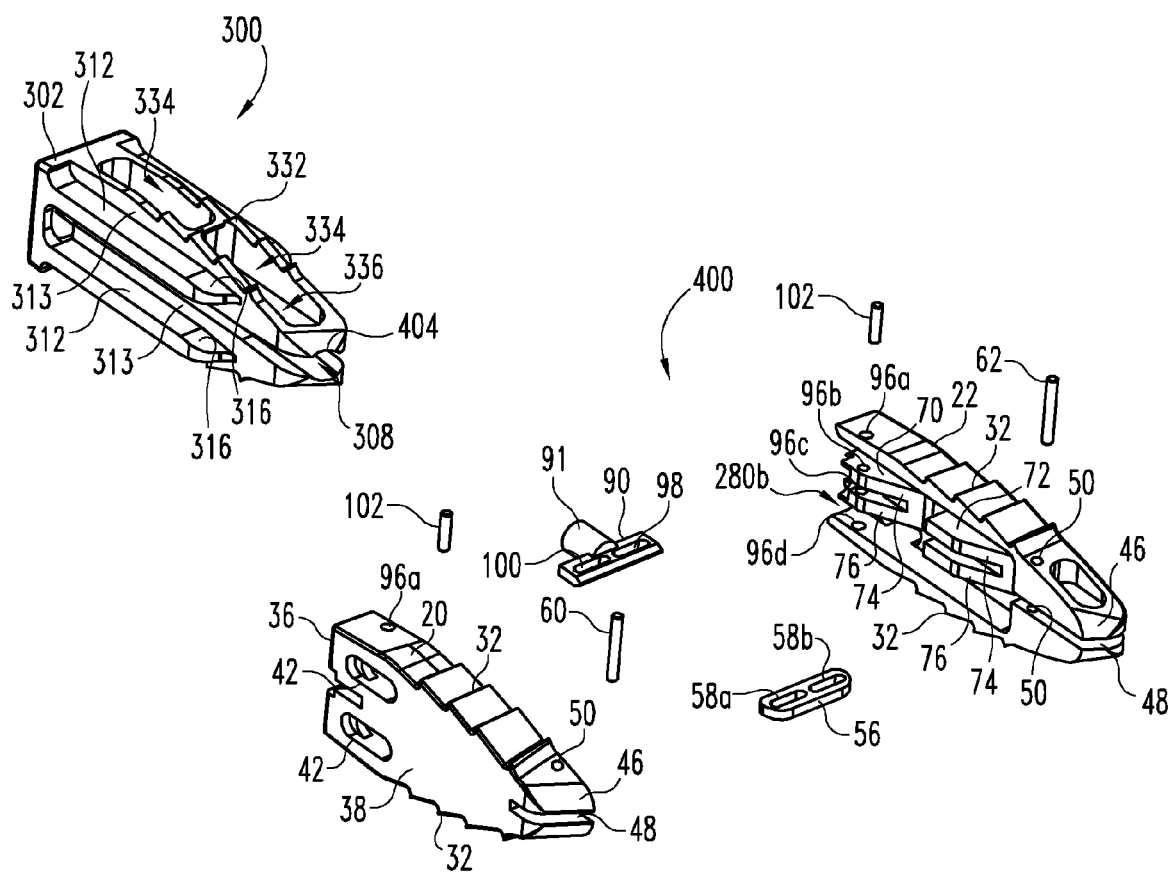
FIG. 18 is an assembly view of the implant illustrated in FIG. 16.

Referring to FIGS. 16-18, another representative implant 400 is illustrated wherein like numeral references refer to common features as discussed above with the previous form. For the sake of brevity, only the differences between the two respective implants 10 will be discussed below. All other features of the respective implants are similar and do not warrant a detailed discussion. In this form, the first and second body members 20, 22 have different lengths. In particular, the first body member 20 is shorter than the second body member 22. In addition, as best illustrated in FIG. 17, a front or leading end 402 of the implant 400 is angled at angle A, which can range between 25-40°. Further, the bone graft member 300 includes a front or leading end 404 that is also angled at angle A. The angle A tapers from the second body member 22 inwardly towards the first body member 20. In addition, a leading end 404 of the bone graft member 300 tapers inwardly at angle A towards the first body member 20. As illustrated in FIG. 17, in this form the implant 400 is preferentially inserted between adjacent vertebral members $V_S$, $V_I$ in an oblique orientation or approach.

Figure 19:
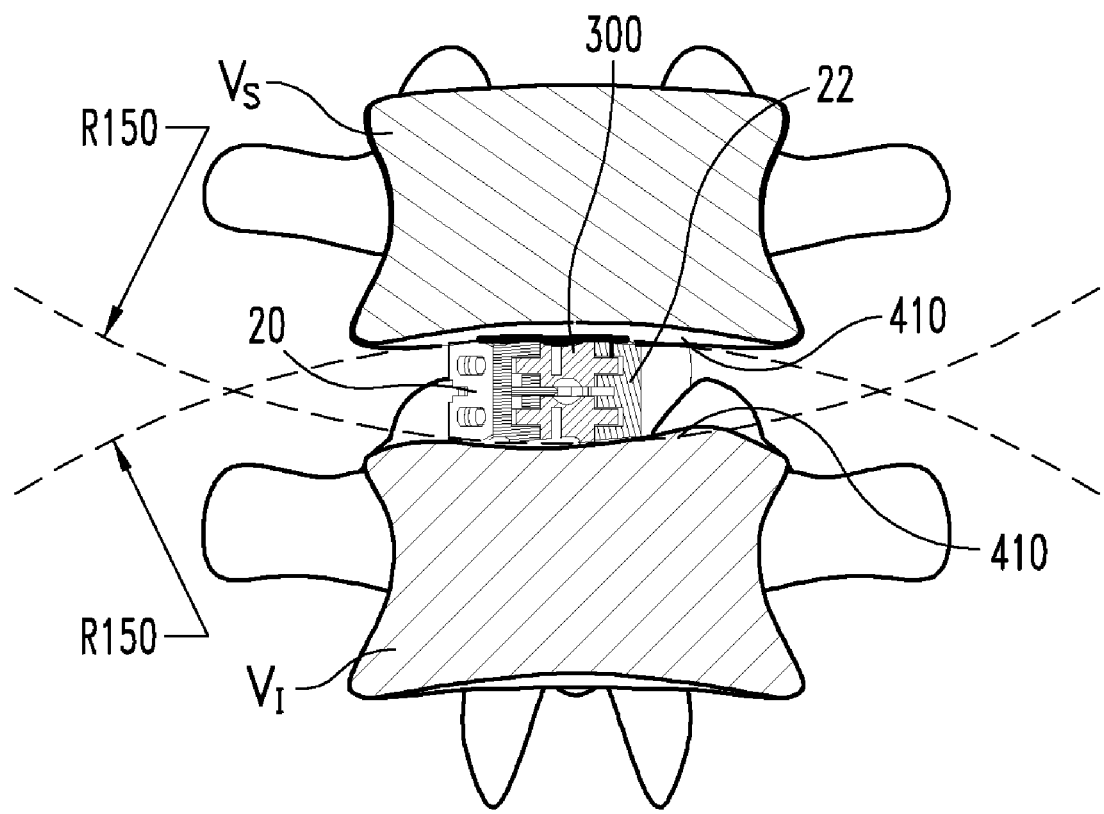
FIG. 19 is a coronal cross-sectional view of the implant illustrated in FIG. 17 along line 19-19 inserted between adjacent vertebral members.
Figure 20:
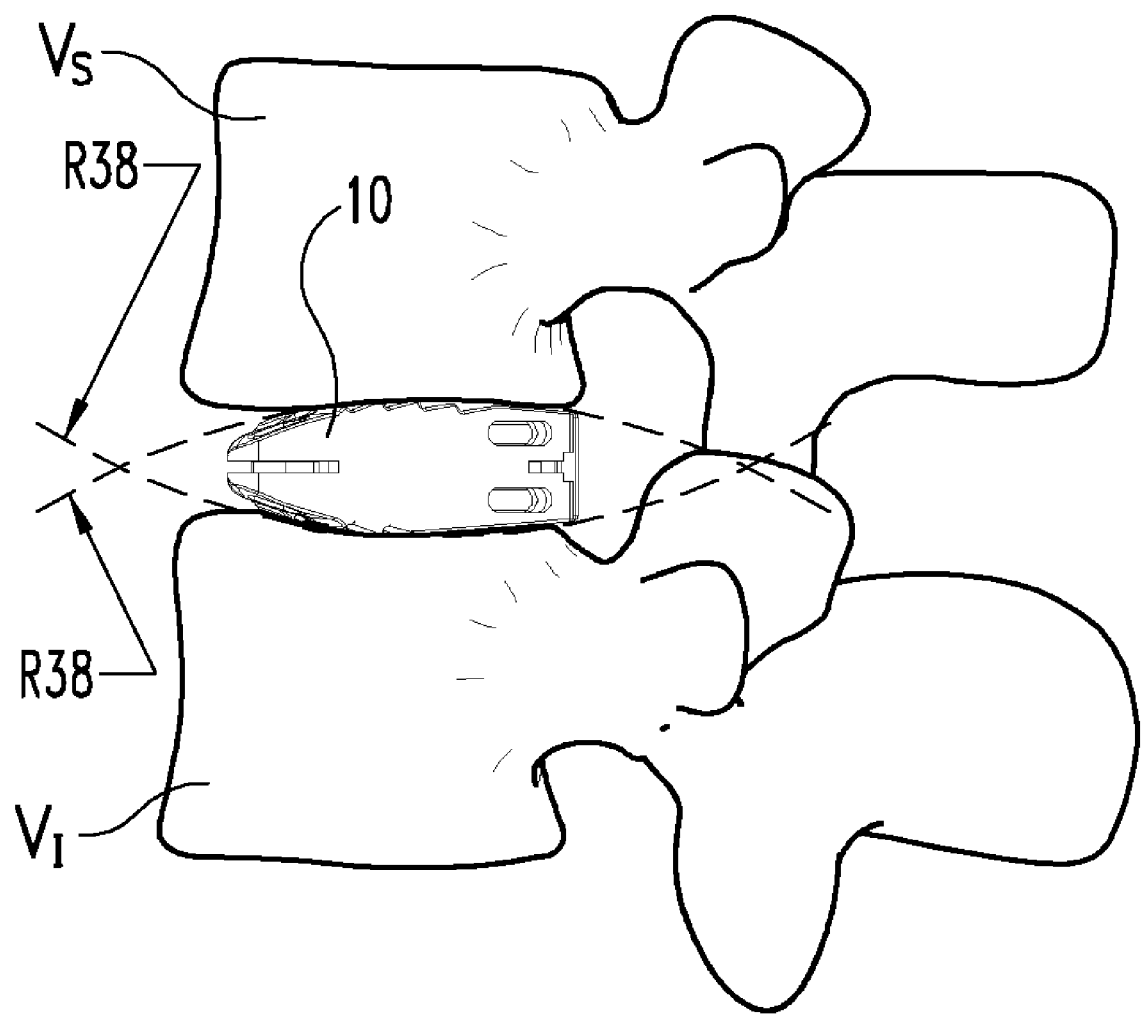
FIG. 20 is a lateral view of the implant illustrated in FIG. 16 inserted between adjacent vertebral members.

Referring to FIGS. 19-20, vertebral body endplates 410 generally have concave surfaces. The concavities typically have a different radius of curvature in the coronal plane (see FIG. 19) than in the sagittal plane (FIG. 20). The disparity between the coronal and sagittal concavities makes it difficult to optimize the implant 10 to endplate 410 interface. In this form, the implant 400 and bone graft member 300 incorporate two different convexities relative to the final anatomic position between adjacent vertebral members $V_S$, $V_I$. In the oblique orientation illustrated in FIG. 17, the implant 400 is positioned at angle B relative to the sagittal plane $S_P$ of the vertebra $V_I$. Angle B can range from 25-40°, but in the form illustrated in FIG. 17 is approximately 30°.

As set forth above, in one form the implant 400 is asymmetrical to optimize the footprint area. In particular, the medial or second body member 22 is longer than the first body member 20 so that the implant 400 sits deeper into the disc space 14. In particular, as illustrated in FIG. 17, the anterior or leading end 402 of the second body member 22 is configured to rest or be positioned at an anterior margin 408 of the vertebral endplate 410. In other forms, the first and second body members 20, 22 as well as the bone graft member 300 can all be the same or different lengths.

Referring to FIG. 19, the implant 400 and bone graft member 300 are illustrated in an oblique orientation with the coronal plane of the adjacent vertebral members $V_S$, $V_I$. In one form the upper surfaces of the first and second body members 20, 22 and the bone graft member 300 can be formed to have a coronal cross-sectional convexity having a radius of approximately 150 millimeters (labeled R150), but this radius could vary between the range of approximately 70-250 millimeters. In addition, the lower surfaces of the first and second body members 20, 22 and the bone graft member 300 can be formed to have a coronal cross-sectional convexity having a radius of approximately 150 millimeters (labeled R150), but this radius could also vary between the range of approximately 70-250 millimeters. The radiuses are chosen so that the implant 400 and bone graft member 300 provide the maximum footprint possible in connection with contacting the endplates 410 of the vertebral members $V_S$, $V_I$ in the sagittal plane.

Referring to FIG. 20, the implant 400 and bone graft member 300 are illustrated in an oblique orientation with the sagittal plane of the adjacent vertebral members $V_S$, $V_I$. In this form, the upper and lower surfaces of the implant 400 and bone graft member 300 are configured to have a sagittal plane convexity radius of approximately 38 millimeters (labeled R38), but this radius can also vary between the range of 10-200 millimeters.

Figure 21A:
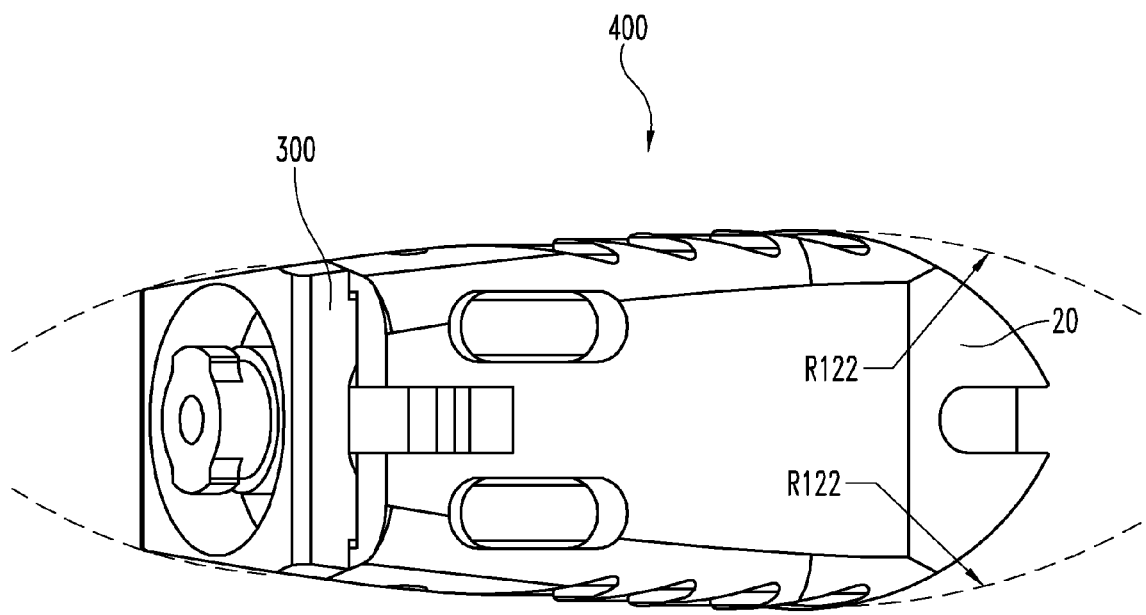
FIG. 21a illustrates is a lateral plane view of the implant illustrated in FIG. 16 showing upper and lower surfaces of the implant having a lateral convexity.

Referring to FIG. 21a, which depicts a lateral plane view of the implant 400, another variant of this form could be a lordotic angle that is designed into the implant 400 such that a desired lordotic angle is generated 25-40° off of the long axis of the implant 400 so that the lordotic angle is in the sagittal plane when the implant 400 is placed in the disc space 14 in the oblique orientation (i.e. −25-40° off of the sagittal plane as illustrated in FIG. 17). In one form, the lordotic angle is formed by the upper and lower surfaces of the first and second body members 20, 22 and bone graft member 300 having a lateral convexity radius of approximately 122 millimeters (labeled R122). However, in other forms the lateral convexity radius can range between 70-250 millimeters. Adjusting the lateral convexity radius changes the lordotic angle created by the implant 400. For example, the lateral convexity radius can be adjusted to create lordotic angles ranging from approximately 3-12°.

Figure 21B:
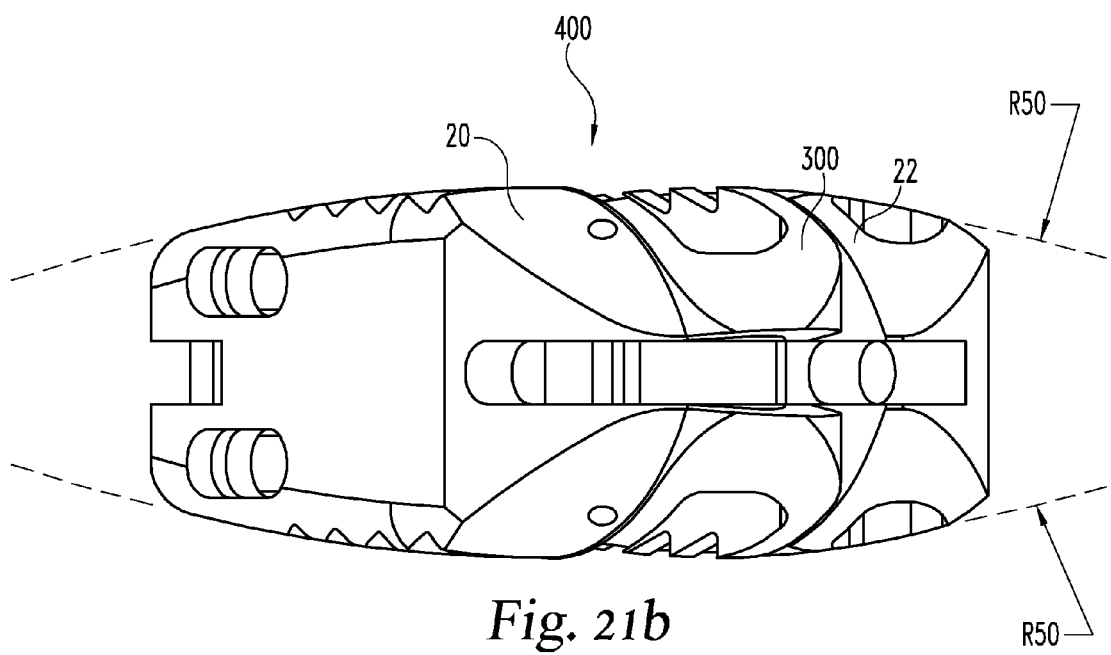
FIG. 21b illustrates a coronal plane view of the implant illustrated in FIG. 16 showing upper and lower surfaces of the implant having a coronal convexity.

Referring to FIG. 21b, which depicts a coronal plane view of the implant 400 oriented in an oblique manner (i.e. −25-45° off of the sagittal plane as illustrated in FIG. 17), another variant of this form is to design the implant 400 to have a coronal convexity to correct lateral angulation of the vertebral members $V_S$, $V_I$. In this form, the upper and lower surfaces of the first and second body members 20, 22 and bone graft member 300 have a predetermined coronal convexity radius of approximately 50 millimeters (labeled R50). However, in other forms the coronal convexity radius could be in the range of 10-200 millimeters depending on the desired level of lateral angulation correction. Another form combines the previously discussed forms and has both the bi-convex orientation for the endplates 410 and the lordotic angle rotated 25-40° off of the long axis of the implant 400.

Figure 22A:
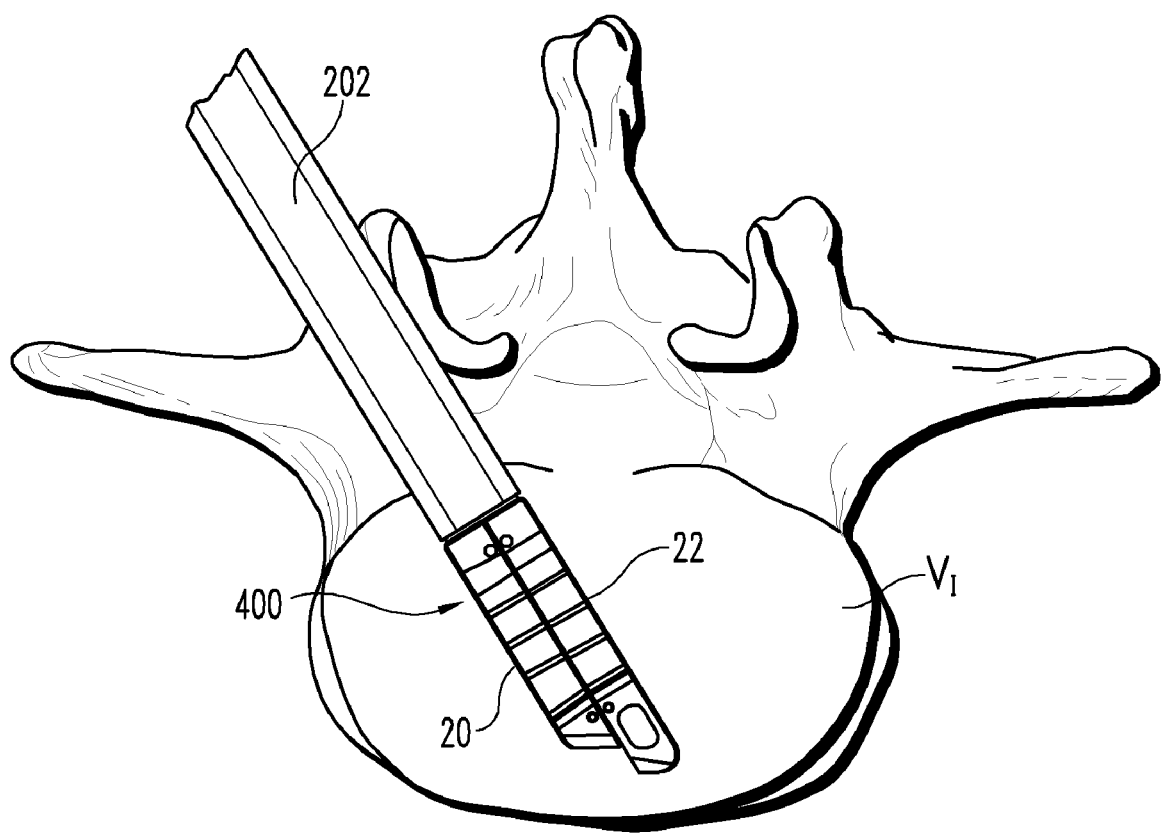
FIGS. 22a-h illustrate the steps of the implant illustrated in FIG. 16 being inserted between adjacent vertebral members.
Figure 22B:
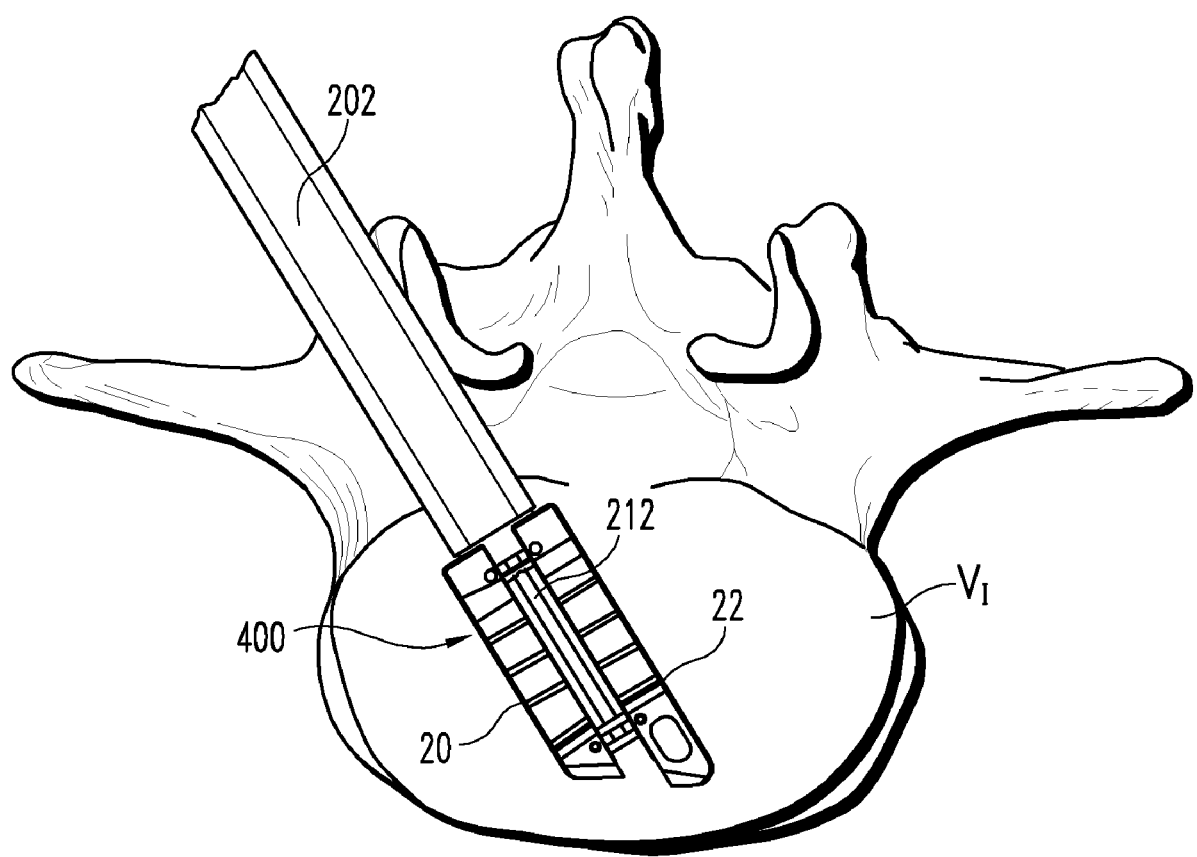
Figure 22C:
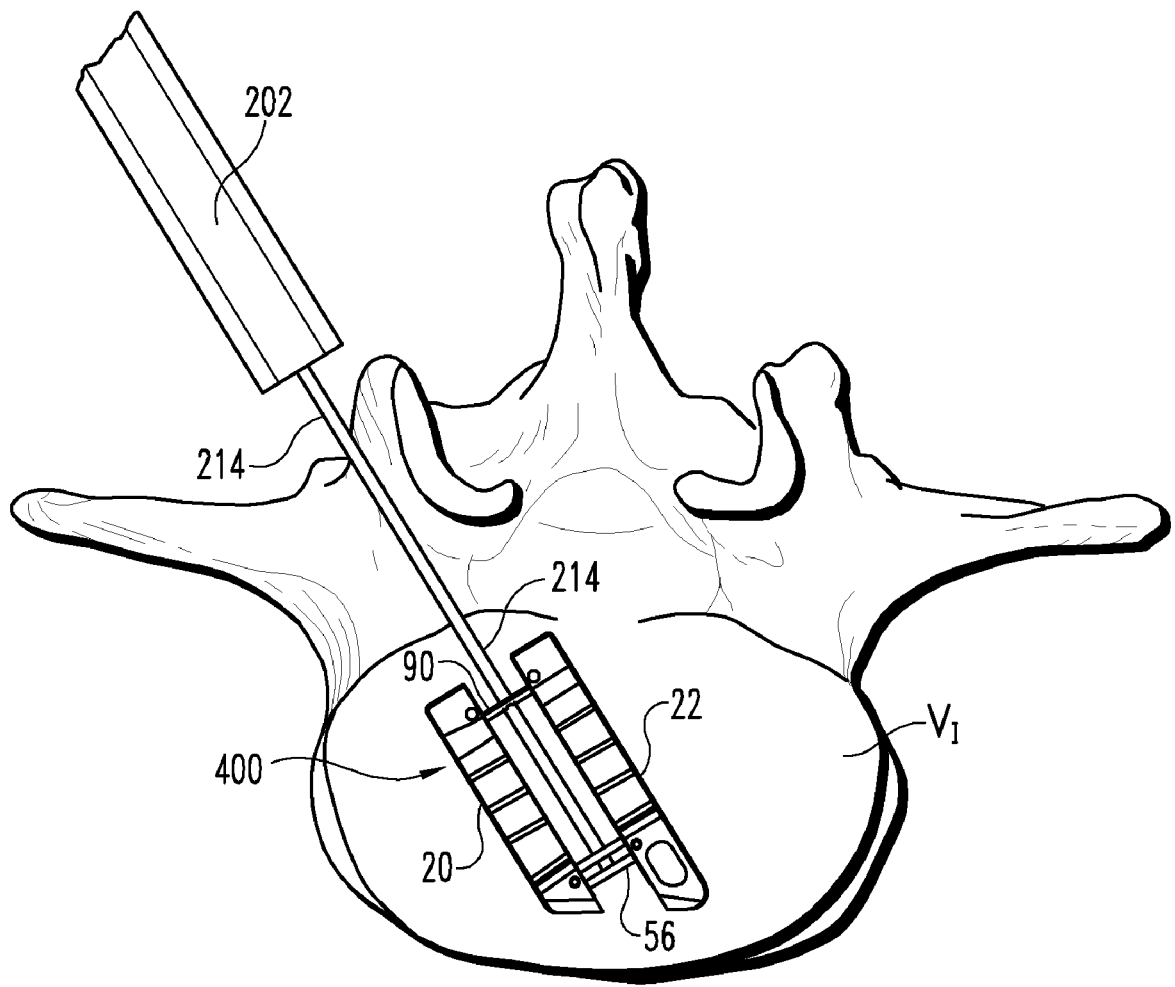

Referring to FIG. 22a, in this illustration the implant 400 has already been connected with the first instrument 202. As such, the expansion component 212 has already been encapsulated within the interior cavity defined by the first and second body members 20, 22. As depicted, the first instrument 202 is used to insert the unexpanded implant 400, from an oblique approach, between adjacent vertebral members $V_S$, $V_I$ ($V_S$ is not shown for clarity purposes). As previously discussed, at this point the implant 400 is in an unexpanded state to minimize the size of the path or channel that the implant 400 is inserted through. At this point, the dial 208 on the first instrument 202 is rotated thereby causing the expansion component 212 to retract or withdraw out of the implant 400 and possibly into at least a portion of the first instrument 202. See FIG. 22b. After the expansion component 212 is fully retracted, the first instrument 202, which is now housing the expansion component 212 in this form, is removed from the patient as illustrated in FIG. 22c. Since the expansion component 212 travels on the switching stick 214, the expansion component 212 and first instrument 202 are pulled off of the switching stick 214 and it is left connected to the implant 400 for insertion of the bone graft member 300.

Figure 22D:
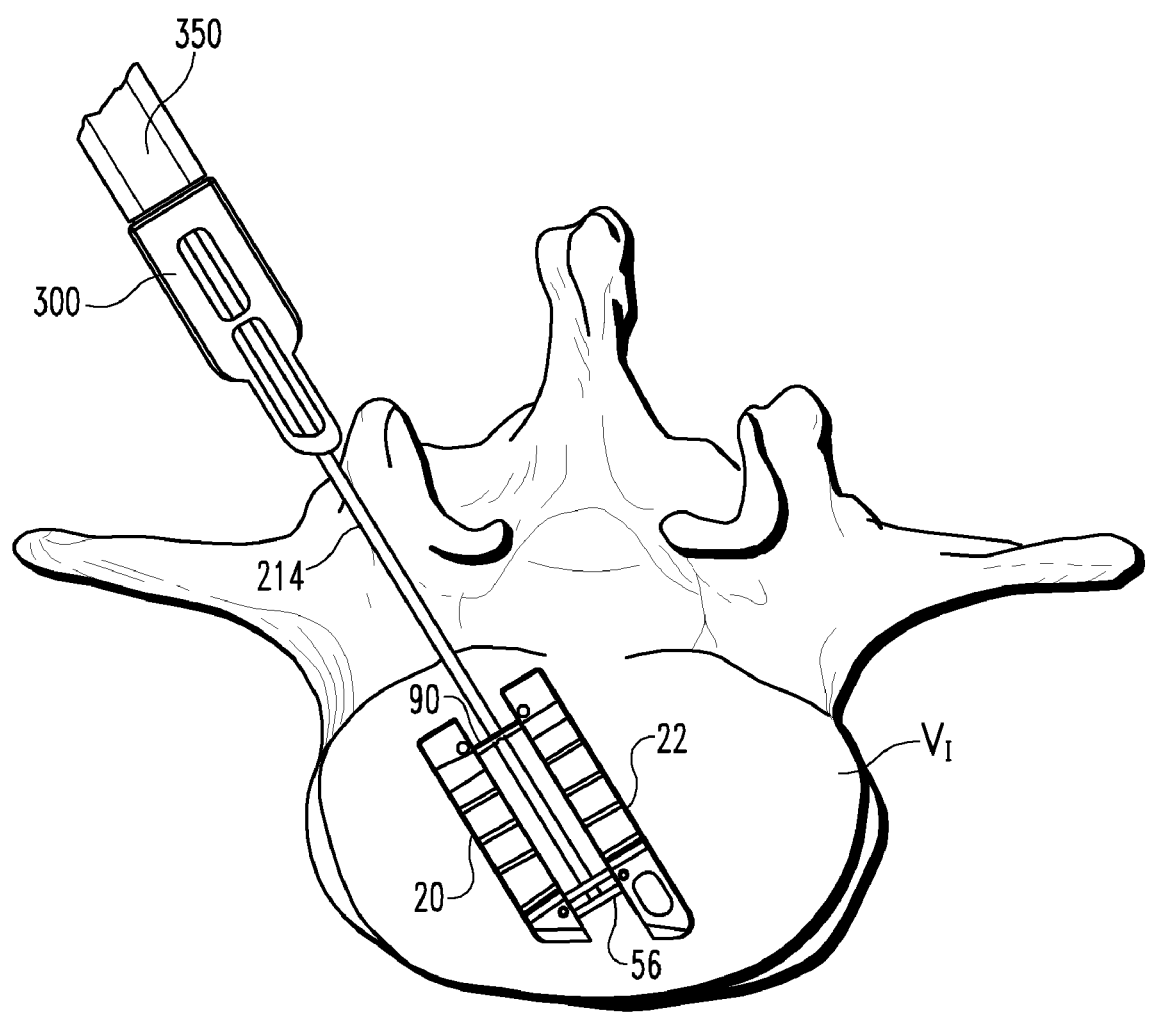
Figure 22E:
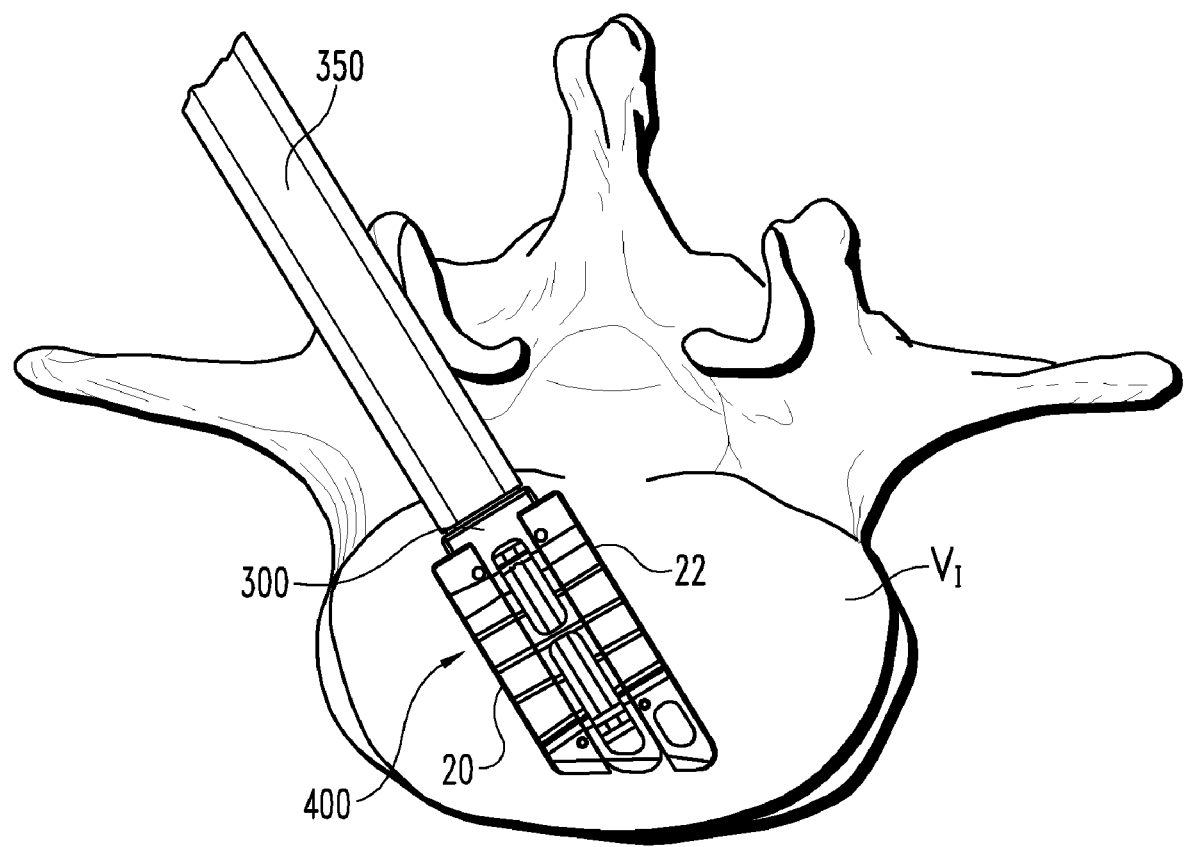
Figure 22F:
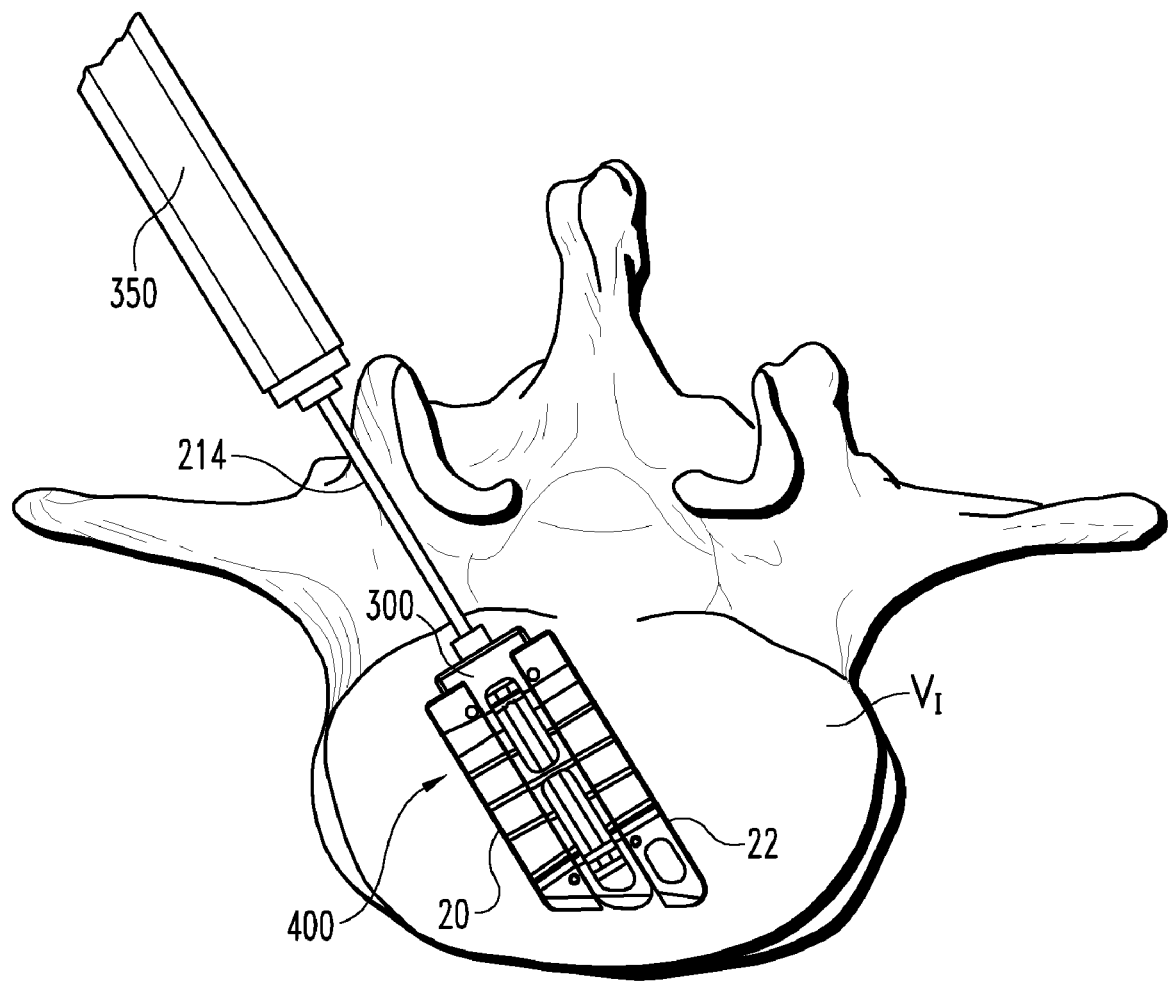

As illustrated in FIGS. 22d and 22e, the bone graft member 300 is inserted onto the switching stick 214 and the second instrument 350 is used to insert the bone graft member 300 into the implant 400. As previously set forth, an end of the bone graft member 300 includes an aperture 330 into which the switching stick 214 is inserted. This allows the bone graft member 300 to travel down the switching stick 214 and into the implant 400. Referring to FIG. 22f, the second instrument 350 is then disconnected from the bone graft member 300 and removed from the patient. In one form, the second instrument 350 is disconnected from the bone graft member 300 by rotating the second instrument 350 about its horizontal axis about 90° thereby unlocking or disconnecting the second instrument 350 from the connector 328 of the bone graft member 300.

Figure 22G:
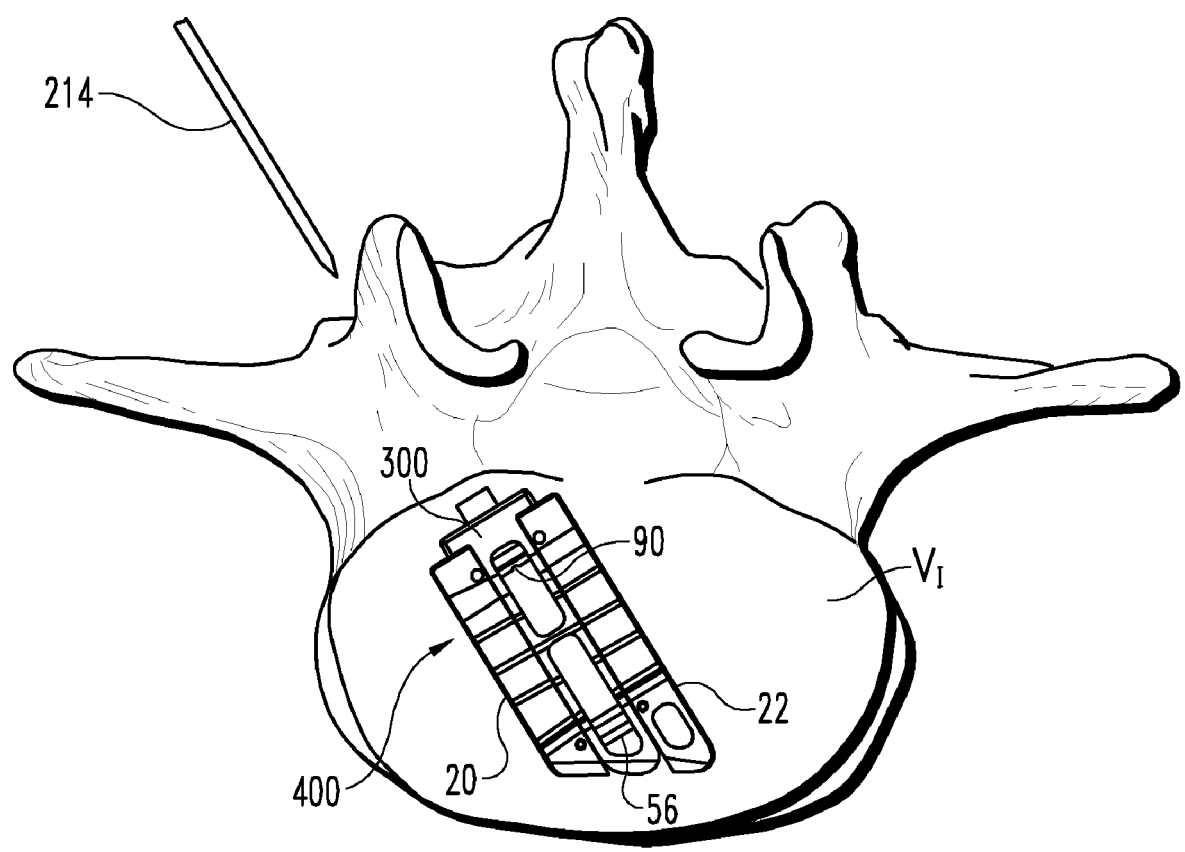
Figure 22H:
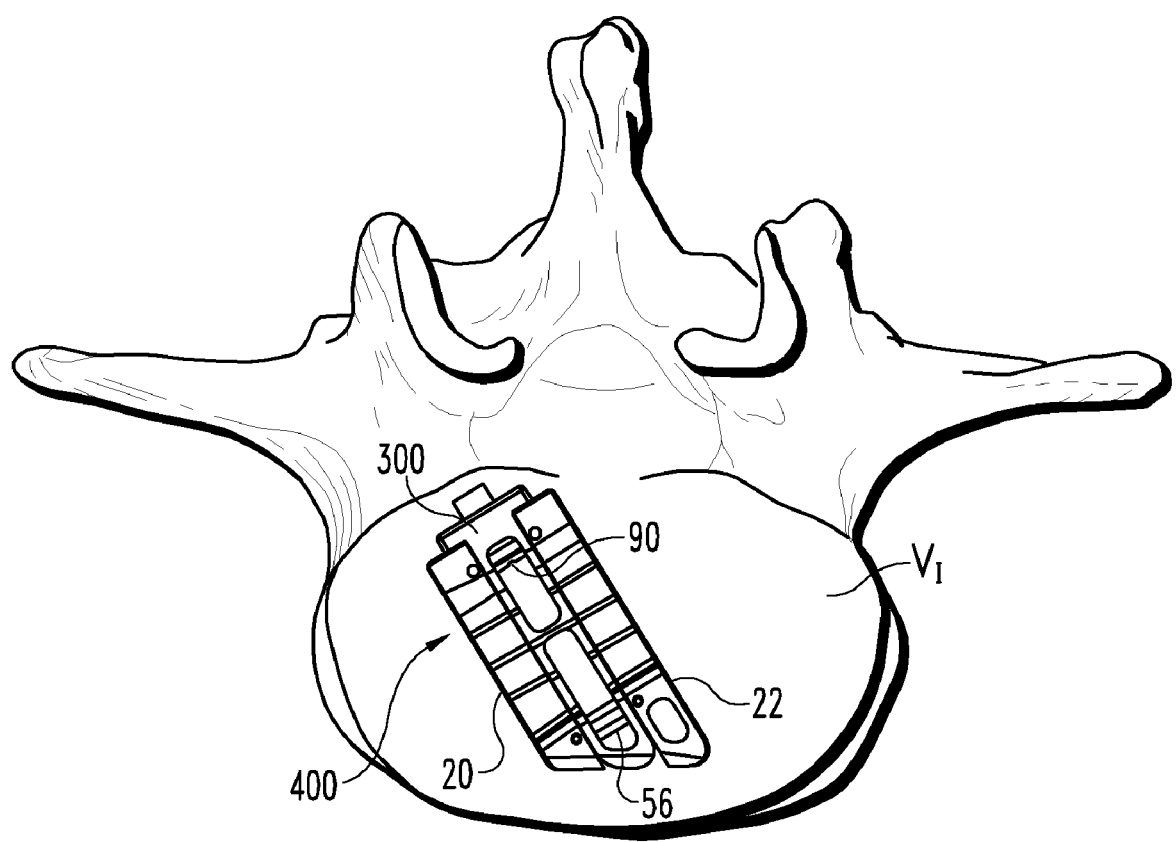

Referring to FIG. 22g, at this point the switching stick 214 is disconnected from the implant 400 and removed from the patient. As such, the implant 400 is left between the adjacent vertebral members $V_S$, $V_I$ in the expanded state as illustrated in FIG. 22h. Although not previously discussed, a plurality of bone grafts 412 is illustrated placed in the elongated passages 334 of the bone graft member 300. In one form, the bone grafts 412 are placed in the elongated passages 334 prior to insertion of the bone graft member 300 into the implant 400. The bone grafts 412 help facilitate the fusion process. In addition, bone growth material may be injected into the implant 400 as well as around the implant 400 to facilitate the fusion process.

Figure 23A:
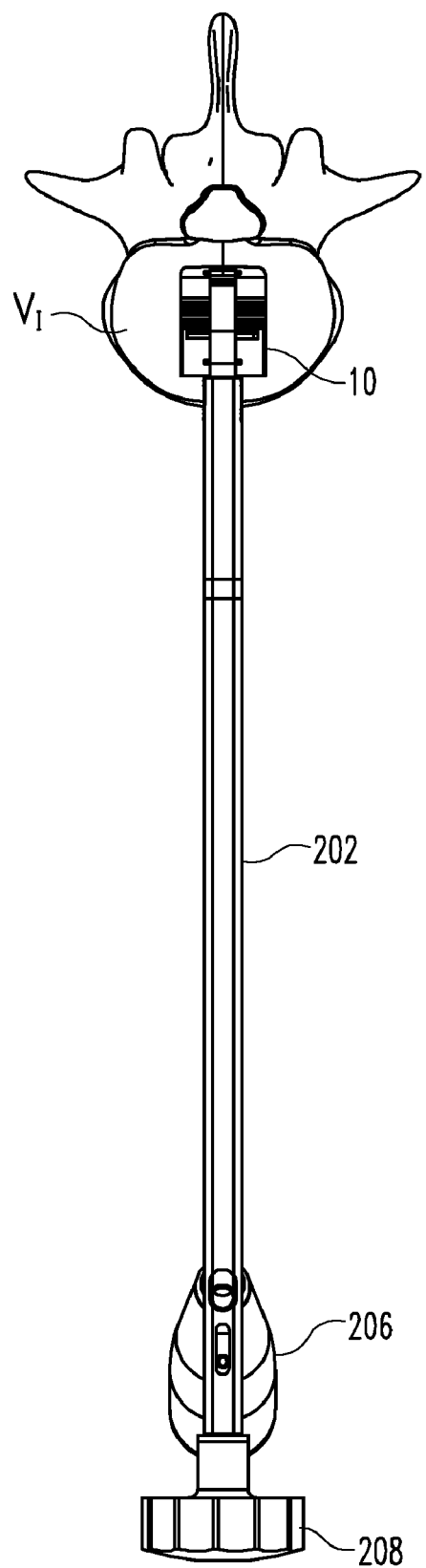
FIG. 23a illustrates a representative implant being inserted from an anterior approach.
Figure 23B:
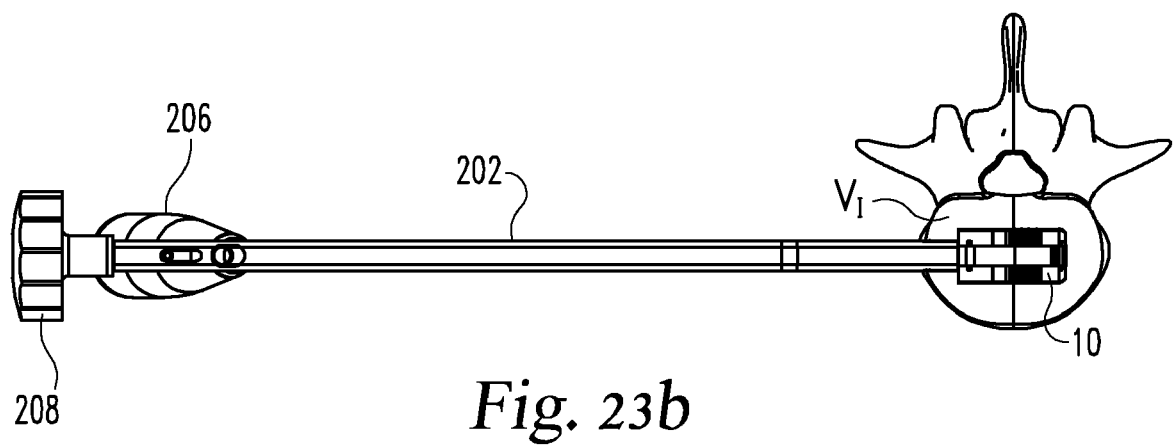
FIG. 23b illustrates a representative implant being inserted from a lateral approach.
Figure 23C:
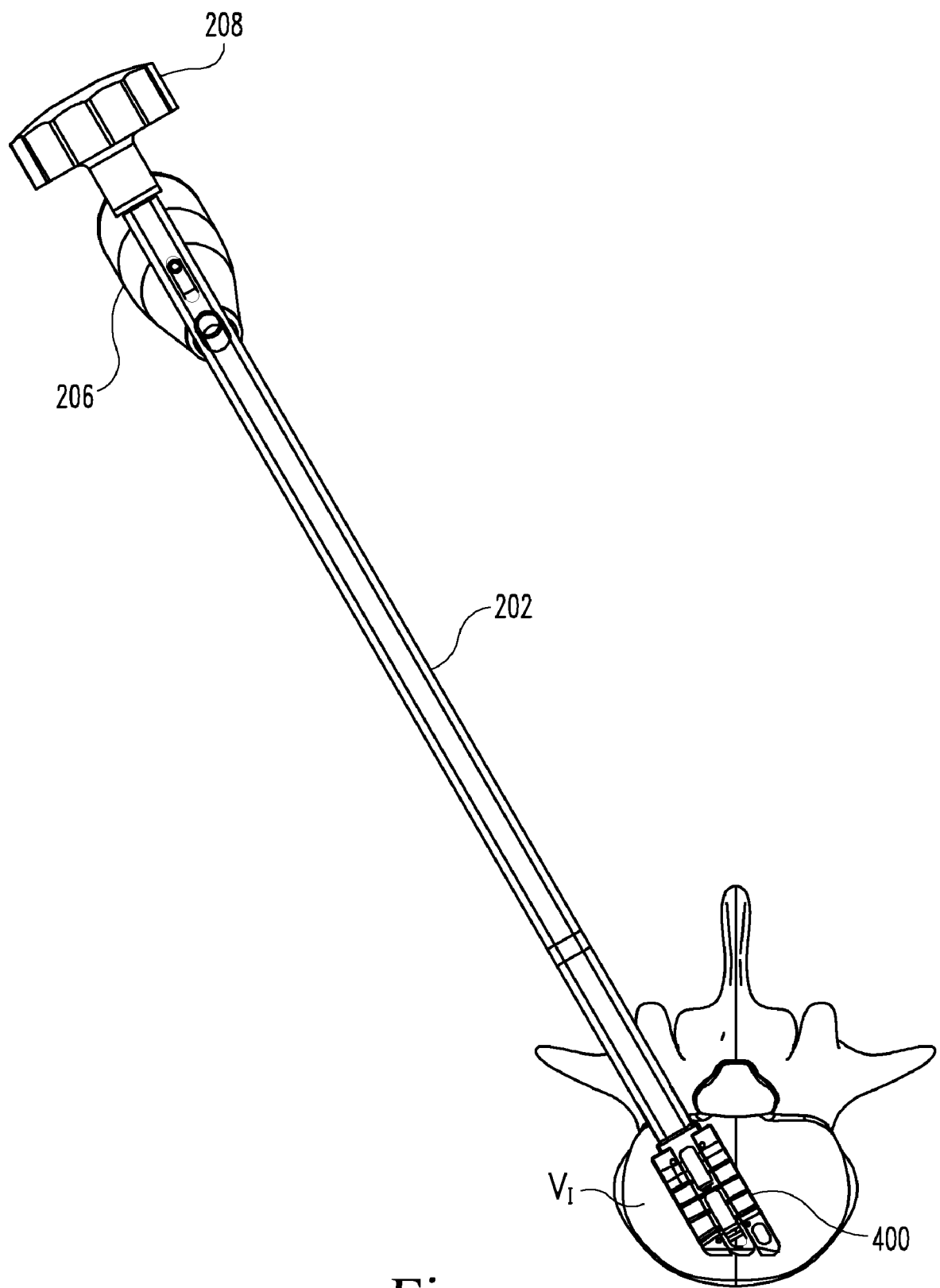
FIG. 23c illustrates a representative implant being inserted from an oblique approach.

Referring to FIG. 23a, as set forth above the implants 10, 400 disclosed herein are capable of being inserted from an anterior approach. In this type of approach, the disc space 14 is typically fused by approaching the spine through the abdomen instead of through the lower back. Referring to FIG. 23b, the implants 10, 400 disclosed herein are also capable of being inserted through a direct lateral or trans-psoas approach. This approach is different from other approaches in that to approach the spine, the surgeon makes a small incision in the skin of the patient's side. Then, using minimally invasive surgical techniques, the surgeon creates a narrow passageway through the underlying soft tissue and the psoas muscle—gently separating the fibers of the psoas muscle rather than cutting through it—directly to the adjacent vertebral members $V_S$, $V_I$ to be treated. Referring to FIG. 23c, as previously set forth, the implants 10, 400 disclosed herein are also capable of being inserted through an oblique approach. In the oblique orientation illustrated in FIG. 23c, the implant 400 is positioned at an angle relative to the sagittal plane of the vertebra $V_I$. The angle can range from 25-40°, but in the form illustrated in FIG. 23c is approximately 30°.

Figure 24A:
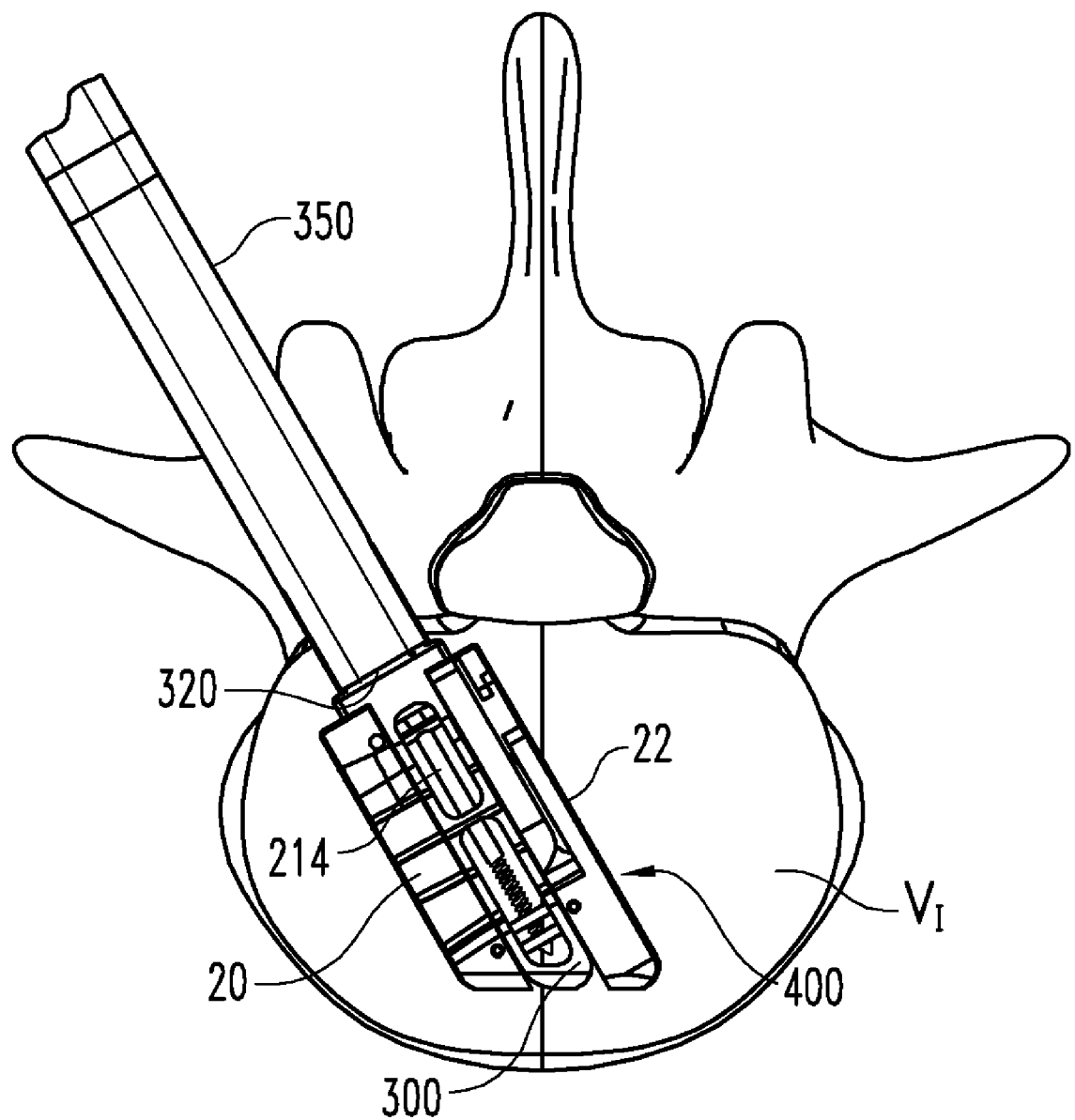
FIG. 24a-k illustrate an exemplary method and instrument utilized to remove the implants disclosed herein from the patient.
Figure 24B:
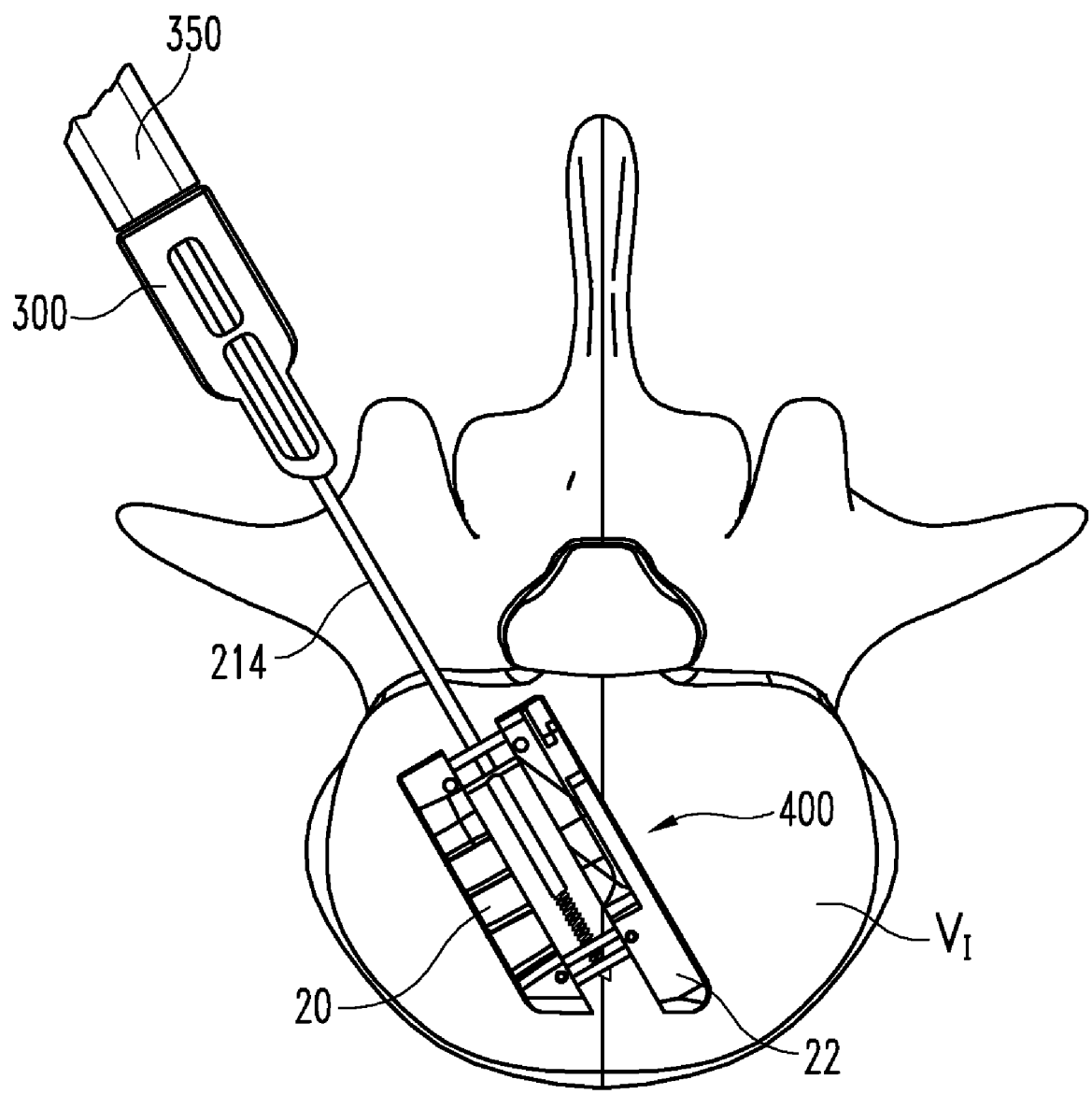

Referring to FIG. 24a, a representative method of removing the implants 10, 400 disclosed herein from between adjacent vertebral members $V_S$, $V_I$ will be discussed. In one form, the switching stick 214 is reconnected with the implant 400. In other forms, the switching stick 214 does not need to be reconnected to the implant 400. Once the switching stick 214 is reconnected with the implant 400, the second instrument 350 is reconnected with the connector 320 of the bone graft member 300. In order to reconnect the second instrument 350, the second instrument 350 is introduced into the patient to the connector 320 in a rotated state such that the female receptacle 351 (see FIG. 15a) engages the connector 320 (see FIG. 14a) of the bone graft member 300. The second instrument 350 is then rotated about the connector 320 causing the female connector 351 of the second instrument 350 to engage the detents 326 of the connector 320 thereby securing the second instrument 350 to the bone graft member 300. As illustrated in FIG. 24b, the bone graft member 300 can then be withdrawn from the adjacent vertebral members $V_S$, $V_I$ thereby leaving the implant 400 positioned between the adjacent vertebral members $V_S$, $V_I$ in an expanded state.

Figure 24C:
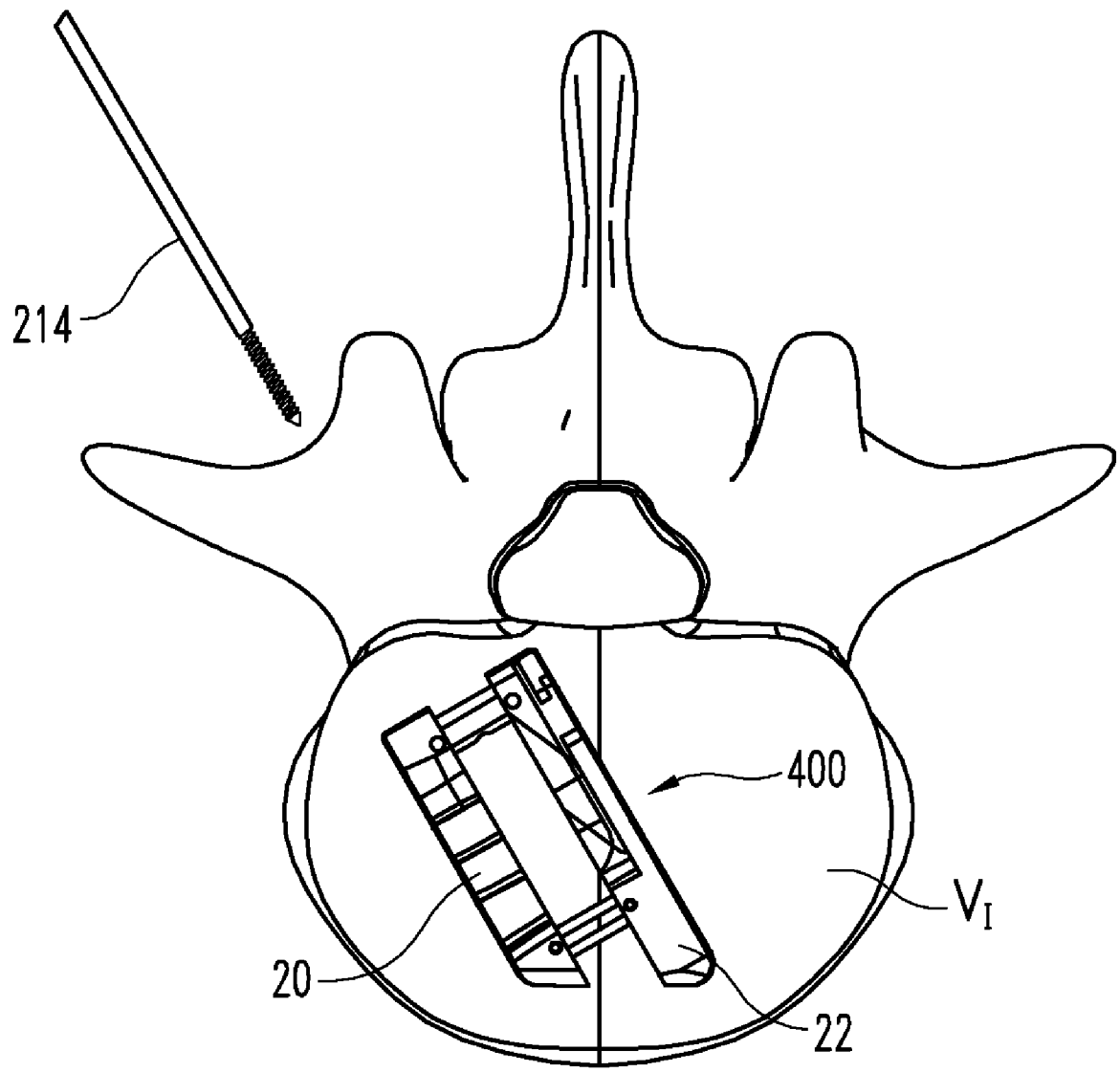
Figure 24D:
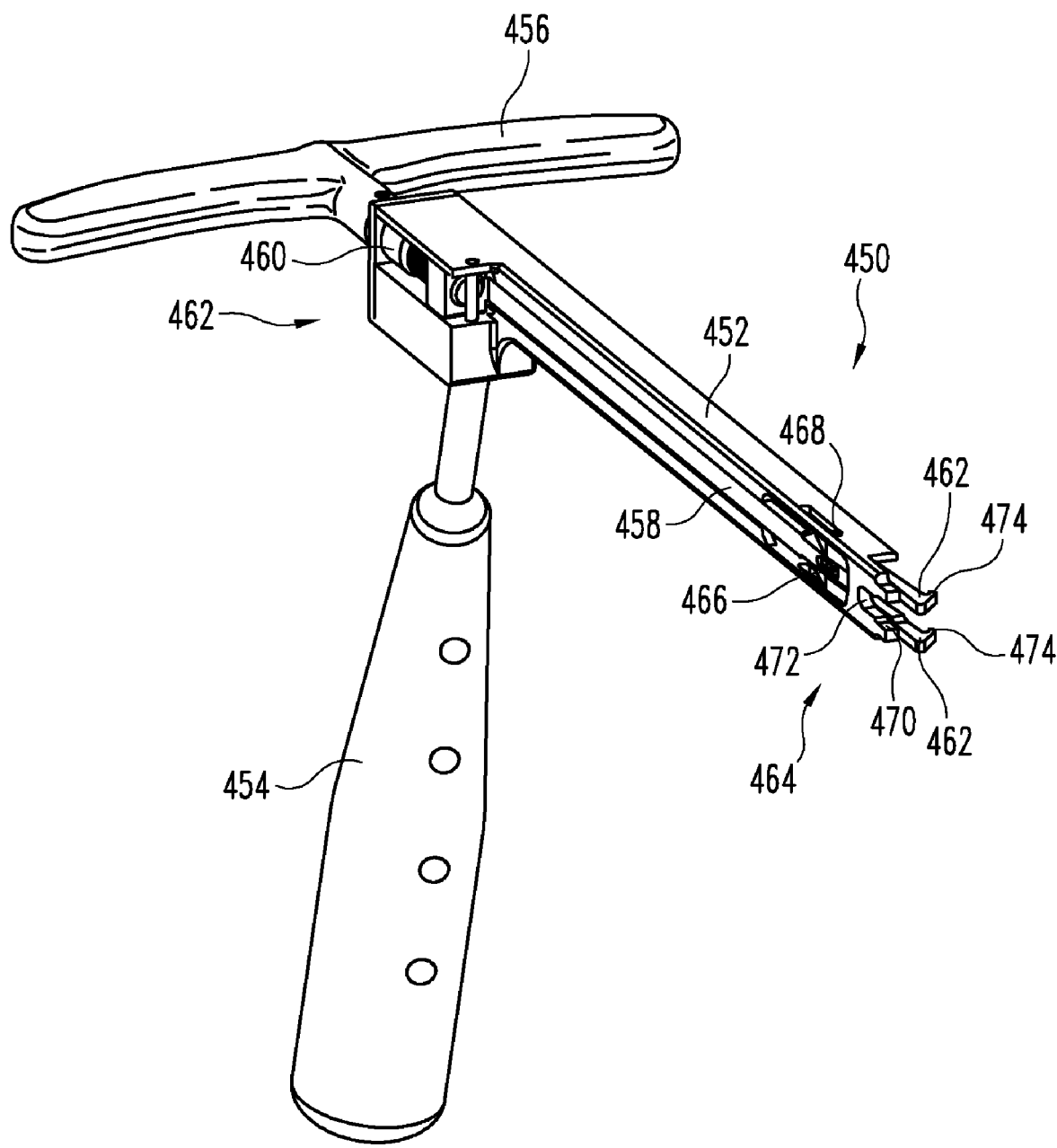

As illustrated in FIG. 24c, the switching stick 214 can then be disconnected from the implant 400 and removed from the patient leaving the implant 400 between the adjacent vertebral members $V_S$, $V_I$ in the expanded state. Referring to FIG. 24d, an implant removal instrument 450 is disclosed that is used to remove the implant 400 from the adjacent vertebral members $V_S$, $V_I$. The removal instrument 450 includes a body 452, a grip portion 454, and a handle 456. As illustrated, the grip portion 454 is connected with the body 452 and the handle 456 is also connected with the body 452. The body 452 houses a shaft 458 that is connected with a retractor component or gear 460 housed at a proximal end 462 of the removal instrument 450. The retractor component 460 is also operatively connected with the handle 456. As the handle 456 is turned, it causes the shaft 458 to move back and forth within the body 452 depending on the direction in which the handle 456 is rotated.

Figure 24E:
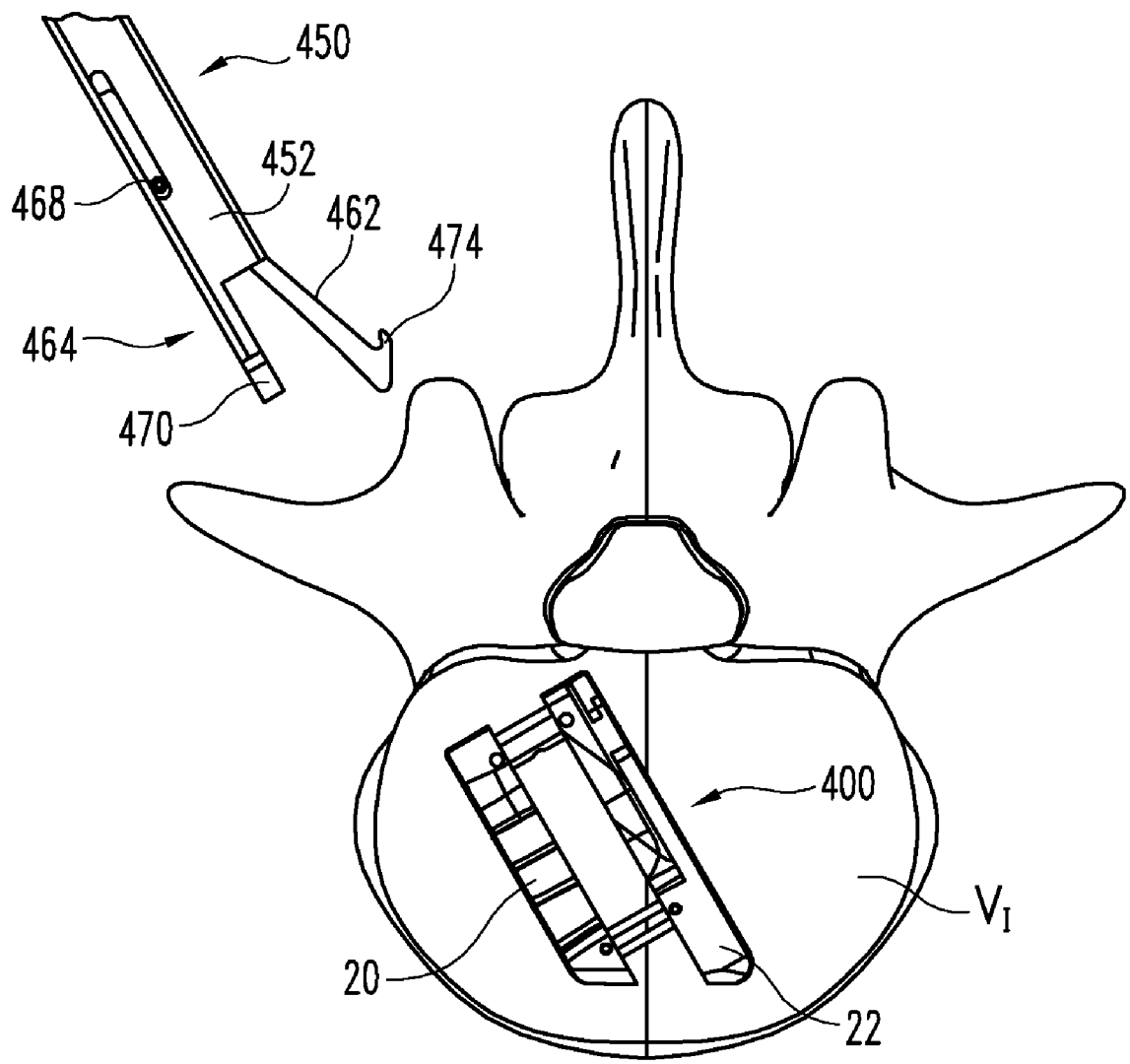
Figure 24F:
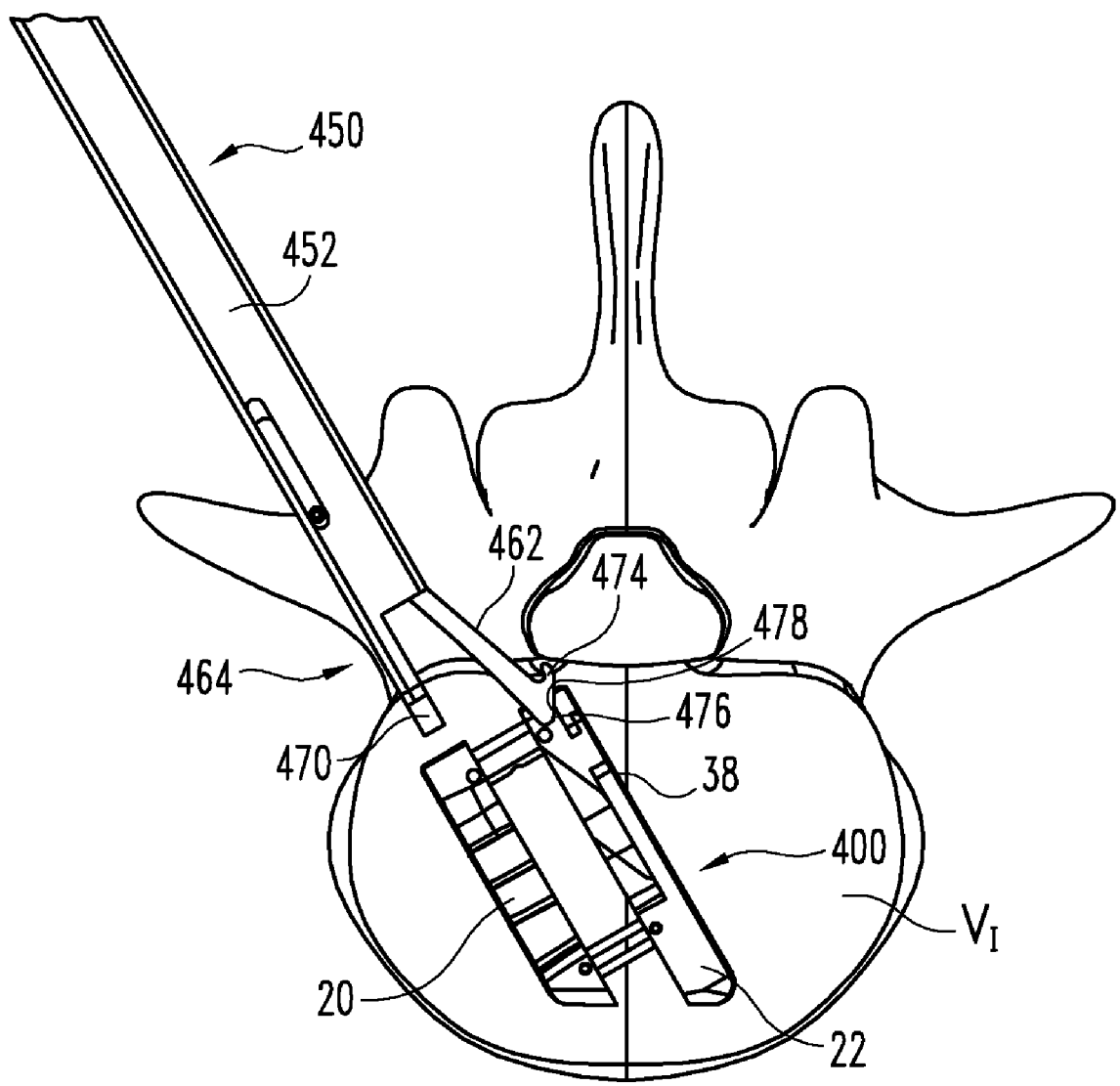

At a proximal end 464 of the removal instrument 450, a pair of opposing retention or gripping members 462 are connected with an end 466 of the shaft 458. The opposing gripping members 462 can be connected with the end 466 of the shaft 458 using any conventional type of connector, but in the illustrated form are connected to the shaft 458 with a pin 468. As further illustrated, the proximal end 464 of the body 452 includes a pair of opposing extension members 470 separated by a gap 472. Referring collectively to FIGS. 24d and 24e, a distal end of the gripping members 462 includes a hook portion 474 that, as discussed in greater detail below, is used to grip or secure the removal instrument 450 to the implant 400. As illustrated in FIGS. 24e and 24f, the removal instrument 450 is inserted into the patient and positioned in alignment with the implant 400.

Referring to FIG. 24f, as the removal instrument 450 approaches the implant 400, a sloped end surface 476 of the opposing gripping members 462 passes into the upper and lower passages 280a, 280b (see e.g.—FIG. 2) defined by the second body member 22. In FIGS. 24f-24k, a portion of the upper bone engaging surface 28 of the second body member 22 has been removed to better illustrate how the removal instrument 450 engages the implant 400 to remove the implant 400 from the patient. The opposing extension members 470 also pass into the upper and lower passages 280a, 280b (see e.g.—FIG. 2) defined by the first body member 20. As illustrated, the sloped end surface 476 makes contact with an inside surface 478 of the sidewall 38 of the second body member 22. This contact causes the opposing gripping members 462 to move inwardly toward the opposing extension members 470 of the body 452 of the removal instrument 450.

Figure 24G:
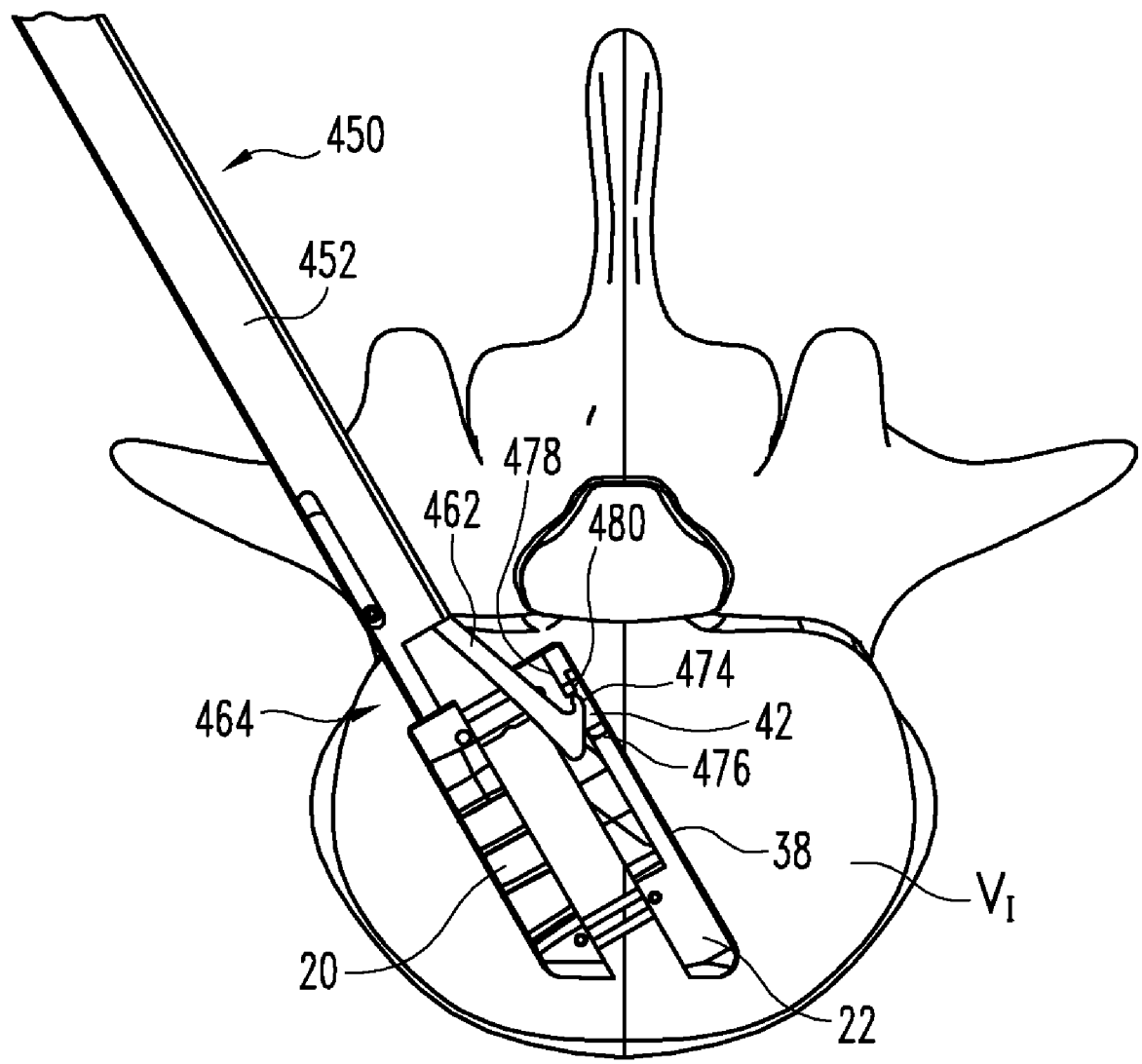
Figure 24H:
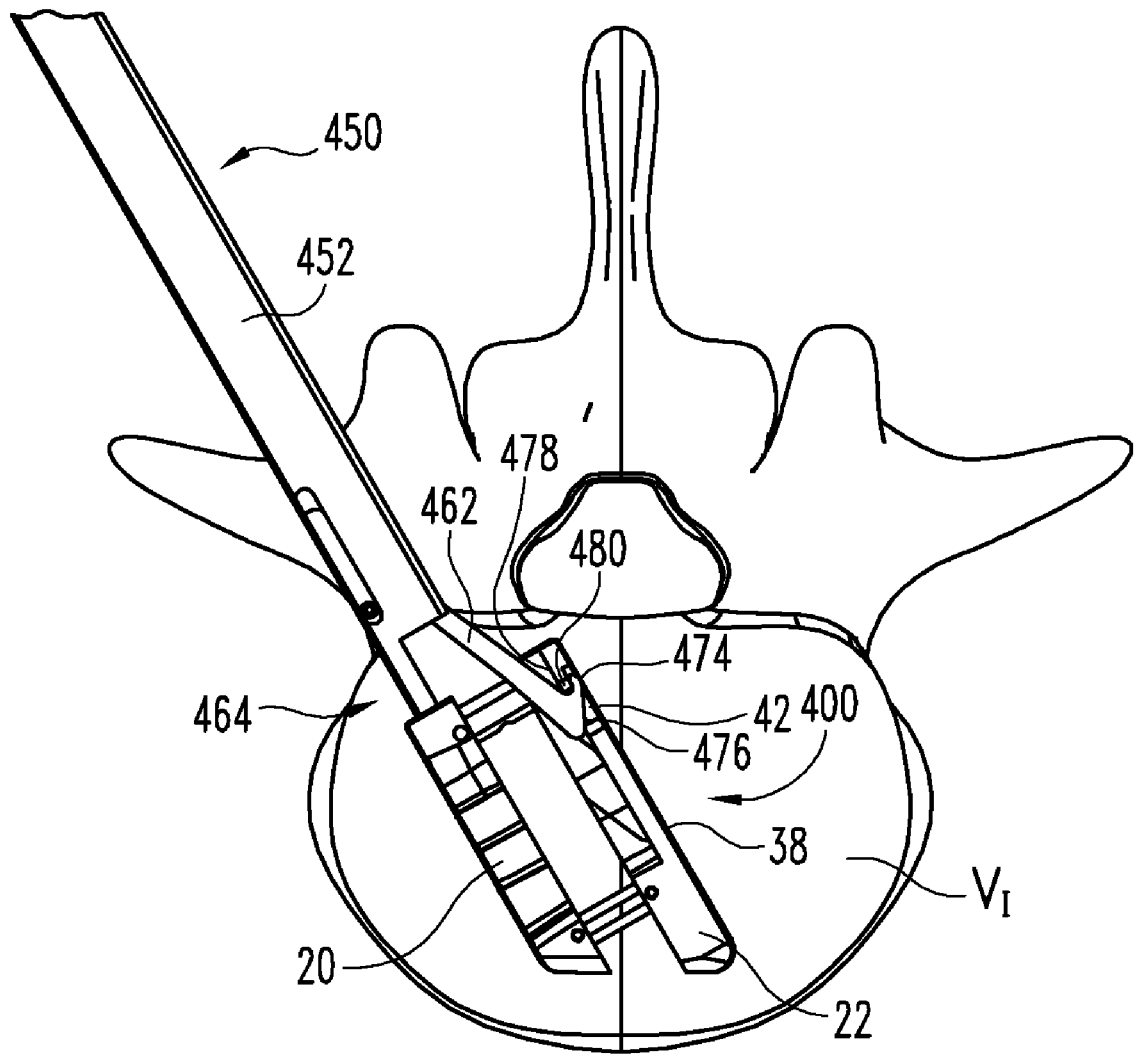

Referring to FIGS. 24g and 24h, the opposing gripping members 462 are inserted into the upper and lower passages 280a, 280b until the hook portion 474 of the opposing gripping members 462 engages a ledge or protrusion 480 defined in the slots 42 of the sidewall 38 of the implant 400. The inward force exerted on the sloped end surface 476 of the opposing gripping members 462 by the inside surface 478 of the sidewall 38 causes the opposing gripping members 462 to spring or move outwardly into the slot 42 once the hook portion 474 of the retention members 462 reaches the end of the ledge 480. As illustrated in FIG. 24h, once positioned in the slot 42, the hook portion 474 of the gripping members 462 engages or hooks the ledge 480 in the slot 42 thereby securing the removal instrument 450 to the implant 400.

Figure 24I:
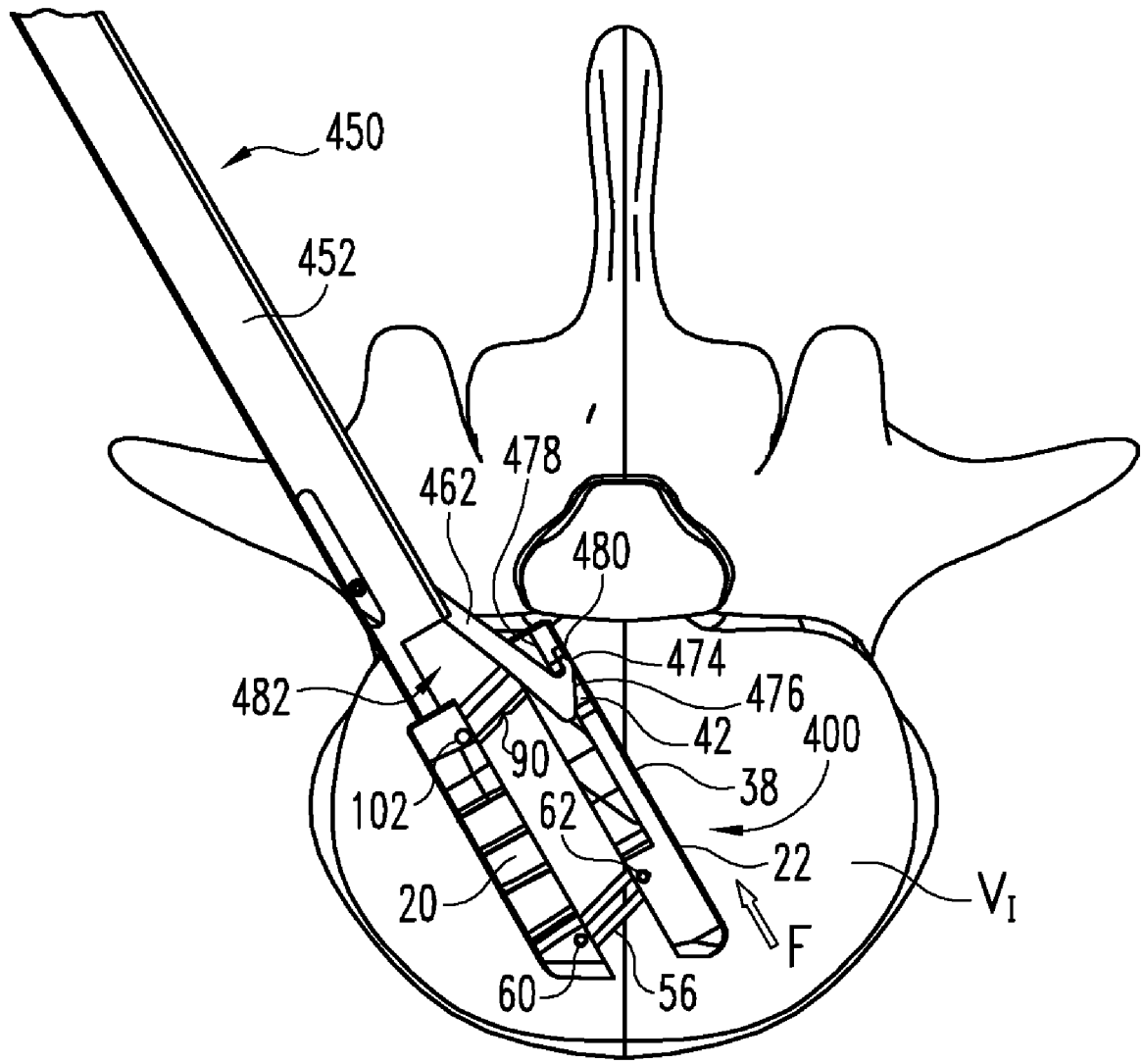
Figure 24J:
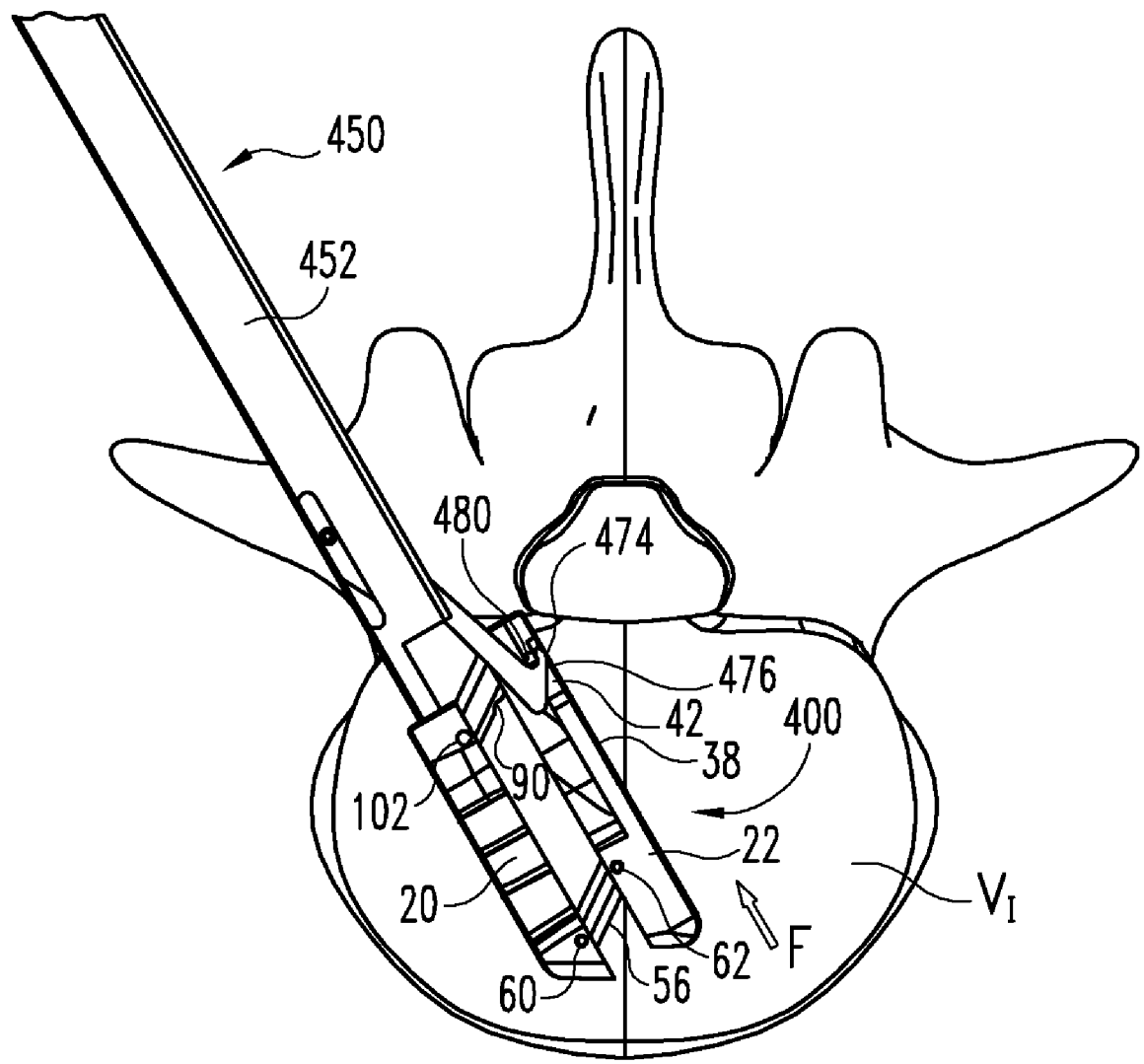
Figure 24K:
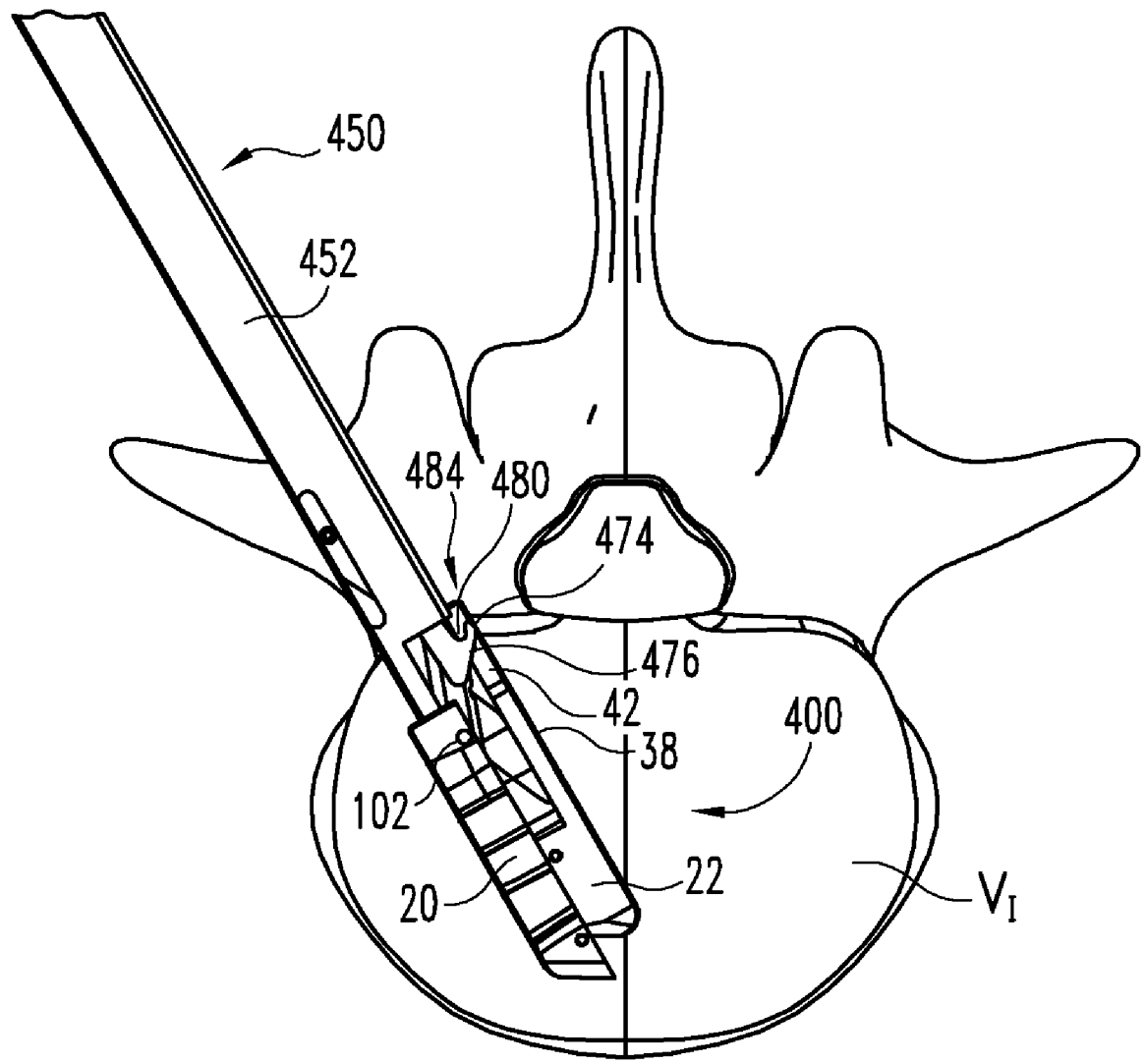

Referring to FIGS. 24i-24k, at this point the handle 456 of the removal instrument 450 is rotated thereby causing the shaft 458 to begin to retract or move the opposing gripping members 462 inwardly into the body 452 of the removal instrument 450. This movement causes a retraction force F to be exerted on the second body member 22. The second body member 22 then begins to move toward the body 452 of the removal instrument 450. In particular, the second body member 22 begins to pivot and move backwardly about the front and rear brackets 56, 92 and the first body member 20 remains stationary. The second body member 22 retracts toward the body 452 of the removal instrument 450 until the implant 400 reaches an unexpanded state. In this form, the proximal end 464 of the body 452 of the removal instrument 450 includes an open cavity 482 that is sized and configured to receive a rear portion of the second body member 22 (see e.g.—FIG. 24k) when retracted and oriented in the unexpanded state.

As illustrated in FIG. 24k, an end portion 484 of the second body member 22 is positioned in the open cavity 482 of the removal instrument 450. An end portion 486 of the first body member 20 is oriented downwardly from the end portion 484 of the second body member 22. Thus, the first body member 20 extends beyond the second body member 22. As illustrated, this allows the implant 400 disclosed herein to be removed in an unexpanded state thereby minimizing the channel that is required to remove the implant 400 from the patient. In essence, the channel does not have to be any wider than the channel needed to insert the implant 400. Once fully oriented in the unexpanded state, the implant 400 can then be removed from the patient. Although implant 400 was discussed herein during the removal process, it should be appreciated that implant 10 and implant 400 are both configured to be removed in the same manner. As such, the discussion of the implant removal process disclosed herein should be construed as applying equally to all forms of the present invention.

Materials for the implants, bone graft members, brackets, and pins disclosed herein can be chosen from any suitable biocompatible material, such as titanium, titanium alloys, cobalt-chromium, cobalt-chromium alloys, or other suitable metal or non-metal material. Of course, it is understood that the relative size of the components can be modified for the particular vertebra(e) to be instrumented and for the particular location or structure of the vertebrae to which the anchor assembly will be engaged.

Although various embodiments have been described as having particular features and/or combinations of components, other embodiments are possible having a combination of any features and/or components from any of embodiments as discussed above. As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof. Furthermore, the terms "proximal" and "distal" refer to the direction closer to and away from, respectively, an operator (e.g., surgeon, physician, nurse, technician, etc.) who would insert the medical implant and/or instruments into the patient. For example, the portion of a medical instrument first inserted inside the patient's body would be the distal portion, while the opposite portion of the medical device (e.g., the portion of the medical device closest to the operator) would be the proximal portion.

While the invention has been illustrated and described in detail in the drawings and foregoing description, the same is to be considered as illustrative and not restrictive in character, it being understood that all changes and modifications that come within the spirit of the invention are desired to be protected.

What is claimed is:

1. An implant for a spinal column, comprising:
   an elongated body positionable in a spinal disc space, said body comprising a first body member and a second body member, said first and second body members each including an upper and lower bone engaging surface, said first body member being longer than said second body member;
   at least one bracket connected with said first and second body members, said at least one bracket being operable to allow said first and second body members to move between an expanded state and an unexpanded state; and
   an expansion component sized and configured to be removably positioned within an interior cavity defined by said first and second body members when in said unexpanded state, said expansion component being operable to cause said first and second body members to laterally expand away from one another to said expanded state as said expansion component is retracted out of said first and second body members.

2. The implant for a spinal column of claim 1, wherein a front end of said first body member tapers inwardly from a sidewall of said first body member at a predetermined angle and a second front end of said second body member tapers outwardly from a second sidewall of said second body member at said same predetermined angle toward said first body member.

3. The implant for a spinal column of claim 1, wherein said upper and lower surfaces of said first and second body members have a predetermined coronal plane cross-section convexity radius.

4. The implant for a spinal column of claim 1, wherein said upper and lower surfaces of said first and second body members have a predetermined sagittal plane convexity radius.

5. The implant for a spinal column of claim 1, wherein said upper and lower surfaces of said first and second body members are configured to define a lordotic angle in a sagittal plane when installed in said spinal disc space in an oblique orientation.

6. The implant for a spinal column of claim 1, wherein said upper and lower surfaces of said first and second body members are configured to define a coronal convexity when installed in said spinal disc space in an oblique orientation.

7. The implant for a spinal column of claim 1, further comprising a bone graft member configured to be inserted into said interior cavity defined by said first and second body members when positioned in said expanded state after said expansion component has been removed from said first and second body members.

8. The implant for a spinal column of claim 7, wherein said upper and lower surfaces of said first and second body members and an upper and lower surface of said bone graft member have a predetermined coronal plane cross-section convexity radius and a predetermined sagittal plane convexity radius.

9. The implant for a spinal column of claim 7, wherein said upper and lower surfaces of said first and second body members and an upper and lower surface of said bone graft member are configured to define a lordotic angle in a sagittal plane when installed in said spinal disc space in an oblique orientation.

10. The implant for a spinal column of claim 7, wherein said upper and lower surfaces of said first and second body members and an upper and lower surface of said bone graft member are configured to have a coronal convexity when installed in said spinal disc space in an oblique orientation.

11. The implant for a spinal column of claim 7, wherein said upper and lower surfaces of said first and second body members and an upper and lower surface of said bone graft member are configured to define a lordotic angle in a sagittal plane when installed in said spinal disc space in an oblique orientation, and wherein said upper and lower surfaces of said first and second body members and said upper and lower surface of said bone graft member are configured to have a coronal convexity when installed in said disc space in said oblique orientation.

12. The implant for a spinal column of claim 1, wherein said upper and lower surfaces of said first and second body members have a predetermined coronal plane cross-section convexity radius and a predetermined sagittal plane convexity radius.

13. An implant for a spinal column, comprising:
an elongated body positionable in a spinal disc space, said body comprising a first body member and a second body member, said first and second body members each including at least one wedge extending into an interior cavity defined by said first and second body members, at least a portion of each of said first and second body members having an upper and lower bone engaging surface that has a predetermined coronal plane cross-section convexity radius;
at least one bracket connected with said first and second body members configured to allow said first and second body members to travel between an expanded state and an unexpanded state;
an expansion component including an upper expansion member and a lower expansion member each having at least one inverted wedge, wherein said expansion component is configured to be positioned in said interior cavity such that a portion of said inverted wedges is in alignment with a portion of said at least one wedge when said first and second body members are positioned in said unexpanded state, wherein as said expansion component is withdrawn from said interior cavity said inverted wedges exert a lateral force on said at least one wedge thereby causing said first and second body members to be positioned in said expanded state.

14. The implant for a spinal column of claim 13, wherein said first and second body members have a predetermined sagittal plane convexity radius.

15. The implant for a spinal column of claim 13, further comprising a bone graft member configured to be inserted into said interior cavity defined by said first and second body members when positioned in said expanded state after said expansion component has been removed from said first and second body members.

16. The implant for a spinal column of claim 15, wherein at least a portion of an upper and lower surface of said bone graft member includes said predetermined coronal plane cross-section convexity radius.

17. The implant for a spinal column of claim 16, wherein at least a portion of said upper and lower surface of said bone graft member includes a predetermined sagittal plan convexity radius.

18. An implant for a spinal column, comprising:
an elongated body positionable in a spinal disc space, said body comprising a first body member and a second body member, said first and second body members each including at least one wedge extending into an interior cavity defined by said first and second body members, at least a portion of each of said first and second body members having an upper and lower bone engaging surface that is configured to define a lordotic angle in a sagittal plane when positioned in said spinal disc space in an oblique orientation;
at least one bracket connected with said first and second body members configured to allow said first and second body members to travel between an expanded state and an unexpanded state;
an expansion component including an upper expansion member and a lower expansion member each having at least one inverted wedge, wherein said expansion component is configured to be positioned in said interior cavity such that a portion of said inverted wedges is in alignment with a portion of said at least one wedge when said first and second body members are positioned in said unexpanded state, wherein as said expansion component is withdrawn from said interior cavity said inverted wedges exert a lateral force on said at least one wedge thereby causing said first and second body members to be positioned in said expanded state.

19. The implant for a spinal column of claim 18, wherein at least a portion of said upper and lower surfaces of said first and second body members are configured to define a coronal convexity when installed in said spinal disc space in said oblique orientation.

20. The implant for a spinal column of claim 18, further comprising a bone graft member configured to be inserted into said interior cavity defined by said first and second body members when positioned in said expanded state after said expansion component has been removed from said first and second body members, wherein at least a portion of said bone graft member includes an upper and lower bone engaging surface that is configured to define a lordotic angle in a sagittal plane when installed in said spinal disc space in said oblique orientation, and wherein at least a portion of said upper and lower surfaces of said bone graft member are configured to define a coronal convexity when installed in said spinal disc space in said oblique orientation.

* * * * *